United States Patent [19]

Hudkins et al.

[11] Patent Number: 5,705,511

[45] Date of Patent: *Jan. 6, 1998

[54] FUSED PYRROLOCARBAZOLES

[75] Inventors: Robert L. Hudkins, Chester Springs, Pa.; Ernest Knight, Jr., Wilmington, Del.

[73] Assignee: Cephalon, Inc., West Chester, Pa.

[*] Notice: The term of this patent shall not extend beyond the expiration date of Pat. No. 5,475,110.

[21] Appl. No.: 526,798

[22] Filed: Sep. 11, 1995

Related U.S. Application Data

[63] Continuation-in-part of Ser. No. 452,335, May 26, 1995, Pat. No. 5,594,009, which is a continuation-in-part of Ser. No. 427,160, Apr. 24, 1995, Pat. No. 5,591,855, which is a continuation-in-part of Ser. No. 323,755, Oct. 14, 1994, Pat. No. 5,475,110.

[51] Int. Cl.$^6$ .................... A61K 31/40; C07D 487/06
[52] U.S. Cl. .................... 514/338; 514/410; 546/256; 546/276.7; 548/417
[58] Field of Search .................... 548/417; 546/256, 546/276.7; 514/410, 338

[56] References Cited

U.S. PATENT DOCUMENTS

| | | |
|---|---|---|
| 4,552,842 | 11/1985 | Nettleton, Jr. et al. . |
| 4,912,107 | 3/1990 | Kleinschroth et al. . |
| 4,923,986 | 5/1990 | Murakata et al. . |
| 5,057,614 | 10/1991 | Davis et al. . |
| 5,185,260 | 2/1993 | Crissman et al. . |
| 5,405,864 | 4/1995 | Broka . |

FOREIGN PATENT DOCUMENTS

| | | |
|---|---|---|
| 0 370 236 | 5/1990 | European Pat. Off. . |
| 0 384 349 | 8/1990 | European Pat. Off. . |
| 0 545 195 A1 | 6/1993 | European Pat. Off. . |
| 0 558 962 A1 | 9/1993 | European Pat. Off. ....... A61K 31/00 |
| PCT/US/ 9512761 | 3/1995 | WIPO . |

OTHER PUBLICATIONS

Bergman et al, "Coupling of Indoleacetic Acid Trianion or Methyl Indoleacetic Acid Dianion. A Biomimetic Approach to Indolocarbazole Alkaloids," *Tetrahedron Letters*, vol. 28, No. 38, pp. 4441–4444 (1987).

Bit et al., "Inhibitors of Protein Kinase C. 3. Potent and Highly Selective Bisindolylmaleimides by Conformational Restriction," *J. Med. Chem.* 36:21–29 (1993).

Bozyczko–Coyne et al., "A rapid fluoremetric assay to measure neuronal survival in vitro," *Journal of Neuroscience Methods* 50:205–216 (1993).

Brenner et al., "Synthesis of Arcyriarubin B and Related Bisindolylmaleimides," *Tetrahedron* 44:2887–2892 (1988).

Buu–Hoï et al., "Carcinogenic Nitrogen Compounds," *J. Chem. Soc.* (1956) 1515–1518.

Davis et al., "Potent selective inhibitors of protein kinase C," *FEBS Letters*, vol. 259, No. 1, pp. 61–63 (1989).

Davis et al., "A Convenient Synthesis of Bisindolyl–and Indolylaryl–Maleic Anhydrides," *Tetrahedron Letters*, vol. 31, No. 16, pp. 2353–2356 (1990).

Davis et al., "A Mild Conversion of Maleic Anhydrides into Maleimides," *Tetrahedron Letters*, vol. 31, No. 36, pp. 5201–5204 (1990).

Davis et al., "Inhibitors of Protein Kinase C. 1. 1 2,3–Bisarylamaleimides," *J. Med. Chem.* 35:177–184 (1992).

Davis et al., "Inhibitors of Protein Kinase C. 2. Substituted Bisindolylmaleimides with Improved Potency and Selectivity," *J. Med. Chem.* 35:994–1001 (1992).

Davis et al., "The Design of Inhibitors of Protein Kinase C; The Solution Conformation of Staurosporine," *J. Chem. Soc., Chem. Commun.* pp. 182–184 (1991).

Fraser, "Expression of Eucaryotic Genes in Insect Cell Cultures," *In Vitro Cellular & Developmental Biology* (1989) 25:225–235.

Gallant et al., "A Stereoselective Synthesis of Indol–β–N–glycosides: An Application to the Synthesis of Rebeccamycin," *J. Org. Chem.* 58:343–349 (1993).

Hallböök, et al., Evolutionary Studies of the Nerve Growth Factor Family Reveal a Novel Member Abundantly Expressed in Xenopus Ovary, *Neuron*, (1991) 6:845–858.

Hara et al., Staurosporine, a Novel Protein Kinase C Inhibitor, Prevents Postischemic Neuronal Damage in the Gerbil and Rat, *Journal of Cerebral Blood Flow and Metabolism* (1990) 10:646–653.

(List continued on next page.)

*Primary Examiner*—Johann Richter
*Assistant Examiner*—Laura L. Stockton
*Attorney, Agent, or Firm*—Fish & Richardson P.C.

[57] ABSTRACT

Disclosed herein are compounds referred to as "fused pyrrolocarbazoles" which possess a variety of functional pharmacological activities including effect on the function and/or survival of trophic factor responsive cells; inhibition of enzymatic activity; inhibition of inflammation-associated responses; inhibition of cell growth associated with hyperproliferative states; and inhibition of developmentally programmed motoneuron death. The disclosed compounds are represented by the following general formula:

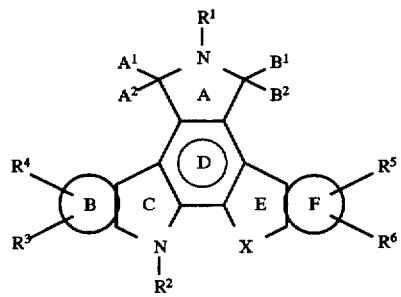

Methodologies for the synthetic production of fused pyrrolocarbazoles are also disclosed, as well as exemplary uses of the compounds.

69 Claims, 9 Drawing Sheets

OTHER PUBLICATIONS

Hendricks et al., "2–Aryl–Indolyl Maleimides–Novel and Potent Inhibitors of Protein Kinase C," *Biorganic & Medicinal Chemistry Letters*, vol. 5, No. 1, pp. 67–72 (1995).

Hughes et al., "Synthesis of Arcyriaflavin B," *Tetrahedron Letters*, vol. 24, No. 13, pp. 1441–1444 (1983).

Hughes et al., "Synthesis of the Indol[2,3-a]carbazole Natural Products Staurosporinone and Arcyriaflavin B," *J. Chem. Soc. Perkin Trans. 1* pp. 2475–2480 (1990).

Kamiya Biomedical Co., Product List (1993) Thousand Oaks, Calif.

Kaneko et al., "Two Synthetic Approaches to Rebeccamycin," *Tetrahedron Letters*, vol. 26, No. 34, pp. 4015–4018 (1985).

Kikkawa et al., Calcium–activated, Phospholipid–dependent Protein Kinase from Rat Brain, *The Journal of Biological Chemistry* (1982) 257:13341–13348.

Link et al., "The First Synthesis of a Fully Functionalized Core Structure of Staurosporine: Sequential Indolyl Glycosidation by Endo and Exo Glycals," *J. Am. Chem. Soc.* 115:3782–3783 (1993).

Magnus et al., "Indole–2,3–Quinodimethanes," *Tetrahedron*, vol. 40, No. 14, pp. 2795–2797 (1984).

Meyer et al., "Production and Characterization of Recombinant Mouse Brain–Derived Neurotrophic Factor and Rat Neurotrophin–3 Expressed in Insect Cells," *Journal of Neurochemistry* (1994) 62:825–833.

Moody et al., "Synthesis of the Staurosporine Aglycon," *J. Org. Chem.* 57:2105–2114 (1992).

Muid et al., "A novel conformationally restricted protein kinase C inhibitor Ro 31–8425, inhibits human neutrophil . . . post–receptor stimuli," *FEBS* vol. 293, No. 1,2 pp. 169–172 (1991).

Mulqueen et al., "Oral, anti–inflammatory activity of a potent, selective, protein kinase C inhibitor," *Agents Action*, 37:85–89 (1992).

Nabeshima et al., "Staurosporine, a protein kinase inhibitor, attenuates basal forebrain–lesion–induced amnesia and cholinergic neuronal deficit", *Neuroscience Letters* (1990) 122:13–16.

Pflug et al., *J. Cell Biochem. Suppl.* 18D Abstract Y215 (1994).

Phelps et al., "Generation Patterns of Four Groups of Cholinergic Neurons in Rat Cervical Spinal Cord: A Combined Tritiated . . . Study", *The Journal of Comparative Neurology* (1988) 273:459–472.

Sarstedt et al., "Reaction with Indole Derivatives, ILVIII," *Heterocycles*, vol. 20, No. 3, pp.469–476 (1983).

Smith et al., "Trophic Effects of Skeletal Muscle Extracts on Ventral Spinal Cord Neurons in Vitro: Separation . . . Proteins with Cholinergic Activity", *The Journal of Cell Biology* (1995) 101:1608–1621.

Toullec et al., "The Bisindolylmaleimide GF 109203X Is a Potent and Selective Inhibitor of Protein Kinase C.," *J. Biol. Chem.* vol. 266, No. 24, pp. 15771–15781 (1991).

FUSED PYRROLOCARBAZOLES

This application is a continuation-in-part of U.S. Ser. No. 08/452,335, filed on May 26, 1995, now U.S. Pat. No. 5,594,009, which is a continuation-in-part of U.S. Ser. No. 08/427,160, filed on Apr. 24, 1995, now U.S. Pat. No. 5,591,855 which is a continuation-in-part of U.S. Ser. No. 08/323,755, filed on Oct. 14, 1994, now U.S. Pat. No. 5,475,110.

BACKGROUND OF THE INVENTION

Publications cited throughout this disclosure are incorporated herein by reference.

The microbial-derived material referred to as "K-252a" is a unique compound which has gained significant attention over the past several years due to the variety of functional activities which it possesses. K-252a is an indolocarbazole alkaloid that was originally isolated from a Nocordiosis sp. culture (Kase, H. et al. 39 *J. Antibiotics* 1059, 1986). K-252a is an inhibitor of several enzymes, including protein kinase C ("PKC") and trk tyrosine kinase. The reported functional activities of K-252a are numerous and diverse: tumor inhibition (U.S. Pat. Nos. 4,877,776 and 5,063,330; European Publication 238,011 in the name of Nomato); anti-insecticidal activity (U.S. Pat. No. 4,735,939); inhibition of inflammation (U.S. Pat. No. 4,816,450); treatment of diseases associated with neuronal cells (WIPO Publication WO 94/02488, published Feb. 3, 1994 in the names of Cephalon, Inc. and Kyowa Hakko Kogyo Co., Ltd.).

The reported indolocarbazoles share several common attributes: in particular, each comprises three five-membered rings which all include a nitrogen moiety; staurosporine (derived from Streptomyces sp.) and K-252a (derived from Nocordiosis sp.) each further comprise a sugar moiety linked via two N-glycosidic bonds. Both K-252a and staurosporine have been extensively studied with respect to their utility as therapeutic agents. The indolocarbazoles are generally lypophilic which allows for their comparative ease in crossing biological membranes, and, unlike proteinaceous materials, they manifest a longer in vivo half life.

While K-252a possesses such varied and useful activities, a drawback to the compound is that because it is of microbial origin, it must be derived from culture media via a fermentation process; the literature indicates that K-252a has never been chemically synthesized. Accordingly, compounds which possess the desired functional activities of K-252a but which can be readily derived using chemical synthesis techniques would offer several unique and distinct advantages over the types of carbazole compounds currently available to the art.

SUMMARY OF THE INVENTION

Disclosed herein are synthetic, organic small molecule compounds which are biologically active and which we refer to as "fused pyrrolocarbazoles." By "synthetic" we mean that the disclosed molecules are chemically synthesized de novo; the indolocarbazole K-252a is a "natural" compound in that it must be initially derived via a fermentation process, followed by isolation and purification.

Unlike the indolocarbazoles, our novel fused pyrrolocarbazoles comprise a unique "E" ring which does not include nitrogen at the 12- position (the alphabetical ring designations set forth in Porter, B. and Ross C. 57 *J. Org. Chem.* 2105, 1992, are utilized for reference purposes). Additionally, the fused pyrrolocarbazoles do not include a sugar moiety linked via two N-glycoside bonds. Because our compounds do not include such a sugar moiety, synthetic production can be readily achieved. Beneficially and surprisingly, our unique compounds, which are not of microbial origin, can be readily synthesized and possess a variety of diverse and selective biological activities which allows for a broad range of applications heretofore only observed with certain indolocarbazoles.

Fused pyrrolocarbazoles as disclosed herein are represented by the following general formula:

FORMULA G:

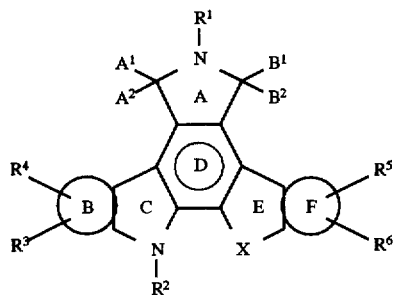

Constituent members are disclosed in detail, infra. As previously noted, in the E ring, constituent "X" is not nitrogen.

Preferred fused pyrrolocarbazoles are represented by the following formula:

FORMULA I:

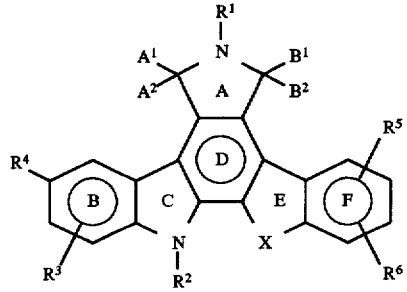

Constituent members are disclosed in detail, infra.

More preferred fused pyrrolocarbazoles are represented by the following formulae:

FORMULA Ia:

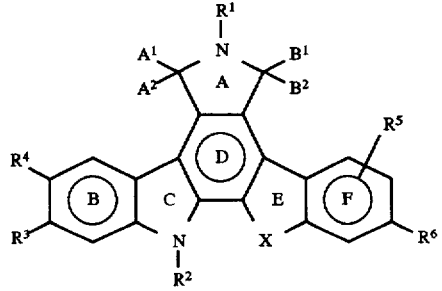

FORMULA Ib:

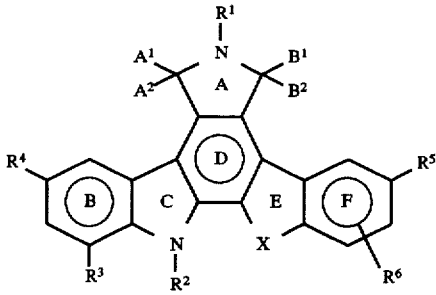

Constituent members are disclosed in detail, infra.

Preferred fused pyrrolocarbazole species are those represented by Formulae I, Ia and Ib in Table I, which is presented infra.

Preferred methodologies for the routes of synthetic preparation are also disclosed herein, including methodologies for the preparation of regiospecific fused pyrrolocarbazole, lactam isomer, and for halogenating a fused pyrrolocarbazole.

We have discovered that our fused pyrrolocarbazoles may be used in a variety of ways, including: enhancing the function and/or survival of cells of neuronal lineage, either singularly or in combination with neurotrophic factor(s) and/or indolocarbozoles; enhancing trophic factor-induced activity; inhibition of protein kinase C ("PKC") activity; inhibition of trk tyrosine kinase activity; inhibition of proliferation of a prostate cancer cell-line; inhibition of the cellular pathways involved in the intimation process; and enhancement of the survival of neuronal cells at risk of dying. Because of these varied activities, the disclosed compounds find utility in a variety of settings, including research and therapeutic environments.

These and other features and advantages of the fused pyrrolocarbazoles will be disclosed in the following pages of the patent disclosure.

DETAILED DESCRIPTION OF PREFERRED EMBODIMENTS

We first describe the drawings.

I. Drawings FIG. 1 is a graph showing that fused pyrrolocarbazoles enhance NT-3 induced ChAT activity of rat basal forebrain cultures.

II. FUSED PYRROLOCARBAZOLES

Figure 1:
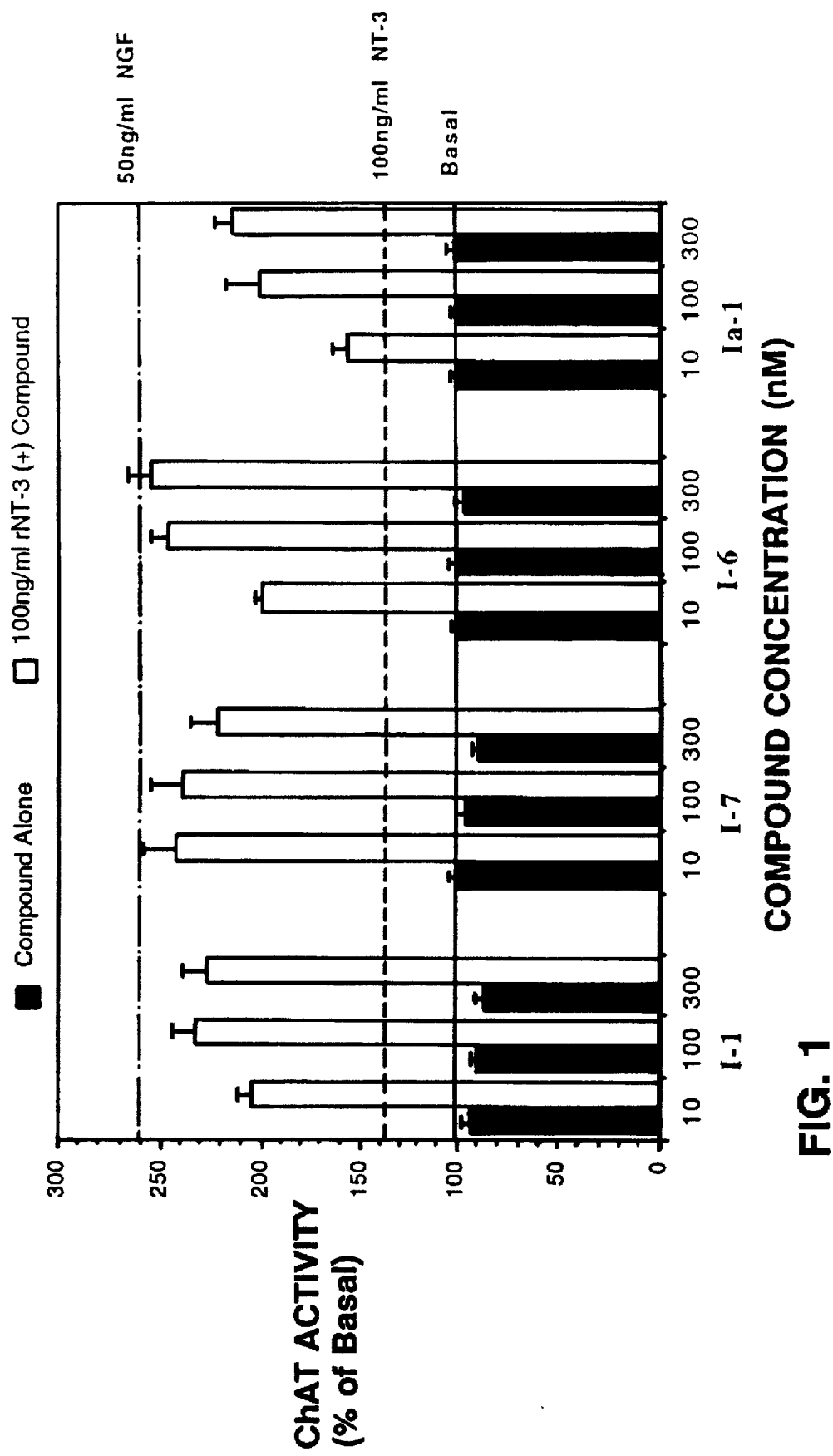

Featured herein are fused pyrrolocarbazoles represented by the following Formulae:

A. FORMULA G

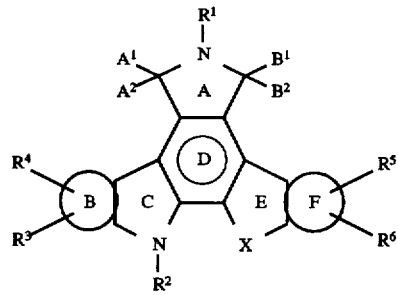

wherein:
a) $E^1$ and $E^2$, independently, each together with the carbon atoms to which they are attached, form either
  1) an unsaturated 6-membered carbocyclic aromatic ring in which from one to three carbon atom(s) may be replaced by nitrogen atom(s); or
  2) an unsaturated 5-membered carbocyclic aromatic ring in which either
    i) one carbon atom is replaced with an oxygen, nitrogen, or sulfur atom; or
    ii) two carbon atoms are replaced with a sulfur and nitrogen atom, or an oxygen and nitrogen atom;
b) $A^1$ and $A^2$ together represent O, and $B^1$ and $B^2$ together represent O;
c) $R^1$ is H, alkyl of 1–4 carbons (inclusive), aryl, arylalkyl, heteroaryl, and heteroarylalkyl; $COR^9$, where $R^9$ is alkyl of 1–4 carbons (inclusive), or aryl, preferably phenyl or naphthyl; —$OR^{10}$, where $R^{10}$ is H or alkyl of 1–4 carbons (inclusive); —$CONH_2$, —$NR^7R^8$, —$(CH_2)_nNR^7R^8$, where n is an integer of 1–4 (inclusive); or —$O(CH_2)_nNR^7R^8$; and either
  1) $R^7$ and $R^8$ independently are H or alkyl of 1–4 carbons (inclusive); or
  2) $R^7$ and $R^8$ are combined together to form a linking group of the general formula —$(CH_2)_2$—$X^1$—$(CH_2)_2$—, where $X^1$ is O, S or $CH_2$;
d) $R^2$ is H, —$SO_2R^9$; —$CO_2R^9$, —$COR^9$, alkyl of 1–8 carbons (inclusive), preferably an alkyl of 1–4 carbons (inclusive), alkenyl of 1–8 carbons (inclusive), preferably an alkenyl of 1-4 carbons (inclusive), or alkynyl of 1-8 carbons (inclusive), preferably an alkynyl of 1-4 carbons (inclusive); or a monosaccharide of 5-7 carbons (inclusive) where each hydroxyl group of the monosaccharide independently is either unsubstituted or is replaced by H, alkyl of 1-4 carbons (inclusive), alkylcarbonyloxy of 2-5 carbons (inclusive) or alkoxy of 1-4 carbons (inclusive); and either 1) each alkyl of 1-8 carbons (inclusive), alkenyl of 1-8 carbons (inclusive), or alkynyl of 1-8 carbons (inclusive) is unsubstituted; or
2) each alkyl of 1-8 carbons (inclusive), alkenyl of 1-8 carbons (inclusive), or alkynyl of 1-8 carbons (inclusive) independently is substituted with 1-3 aryl of 6-10 carbons (inclusive), preferably phenyl or naphthyl; heteroaryl; F, Cl, Br, I, —CN, —NO$_2$, OH, —OR$^9$, —O(CH$_2$)$_n$NR$^7$R$^8$, —OCOR$^9$, —OCONHR$^9$, O-tetrahydropyranyl, NH$_2$, —NR$^7$R$^8$, —NR$^{10}$COR$^9$; —NR$^{10}$CO$_2$R$^9$, —NR$^{10}$CONR$^7$R$^8$, —NHC(=NH)NH$_2$, —NR$^{10}$SO$_2$R$^9$, —S(O)$_y$R$^{11}$, where R$^{11}$ is H or alkyl of 1-4 carbons, aryl of 6-10 carbons, preferably phenyl or naphthyl, or heteroaryl and y is 1 or 2; —SR$^{11}$, —CO$_2$R$^9$, —CONR$^7$R$^8$, —CHO, COR$^9$, —CH$_2$OR$^7$, —CH=NNR$^{11}$R$^{12}$, —CH=NOR$^{11}$, —CH=NR$^9$, —CH=NNHCH(N=NH)NH$_2$, —SO$_2$NR$^{12}$R$^{13}$, —PO(OR$^{11}$)$_2$, or OR$^{14}$ where R$^{14}$ is the residue of an amino acid after the hydroxyl group of the carboxyl group is removed; and either i) R$^{12}$ and R$^{13}$ independently are H, alkyl of 1-4 carbons (inclusive), aryl of 6-10 carbons, preferably phenyl or naphthyl, or heteroaryl; or
 ii) R$^{12}$ and R$^{13}$ are combined together to form a linking group, preferably —(CH$_2$)$_2$—X$^1$—(CH$_2$)$_2$;

e) each R$^3$, R$^4$, R$^5$ and R$^6$, independently is H, aryl, preferably an aryl of 6-10 carbons (inclusive), more preferably phenyl or naphthyl; heteroaryl; F, Cl, Br, I, —CN, CF$_3$, —NO$_2$, OH, —OR$^9$, —O(CH$_2$)$_n$NR$^7$R$^8$, —OCOR$^9$, —OCONHR$^9$, NH$_2$, —CH$_2$OH, —CH$_2$OR$^{14}$, —NR$^7$R$^8$, —NR$^{10}$COR$^9$, —NR$^{10}$CONR$^7$R$^8$, —SR$^{11}$, —S(O)$_y$R$^{11}$, where y is 1 or 2; —CO$_2$R$^9$, —COR$^9$, —CONR$^7$R$^8$, —CHO, —CH=NOR$^{11}$, —CH=NR$^9$, —CH=NNR$^{11}$R$^{12}$, —(CH$_2$)$_n$SR$^9$, where n is an integer of 1-4 (inclusive), —(CH$_2$)$_n$S(O)$_y$R$^9$, —CH$_2$SR$^{15}$ where R$^{15}$ is alkyl of 1-4 carbons (inclusive); —CH$_2$S(O)$_y$R$^{14}$, —(CH$_2$)$_n$NR$^7$R$^8$, —(CH$_2$)$_n$NHR$^{14}$, alkyl of 1-8 carbons (inclusive), preferably alkyl of 1-4 carbons (inclusive); alkenyl of 1-8 carbons (inclusive), preferably alkenyl of 1-4 carbons (inclusive); alkynyl of 1-8 carbons (inclusive), preferably alkynyl of 1-4 carbons (inclusive); and either 1) each alkyl of 1-8 carbons (inclusive), alkenyl of 1-8 carbons (inclusive) or alkynyl of 1-8 carbons (inclusive) is unsubstituted; or
2) each alkyl of 1-8 carbons (inclusive), alkenyl of 1-8 carbons (inclusive) or alkynyl of 1-8 carbons (inclusive) is substituted as described in d)2), above;

f) X is either
1) an unsubstituted alkylene of 1-3 carbons (inclusive); or
2) X is an alkylene of 1-3 carbons (inclusive) substituted with one R$^2$ group, preferably OR$^{10}$, —SR$^{10}$, R$^{15}$, where R$^{15}$ is an alkyl of 1-4 carbons (inclusive); phenyl, naphthyl, arylalkyl of 7-14 carbons (inclusive), preferably benzyl; or 3) X is —CH=CH—, —CH(OH)—CH(OH)—, —O—,

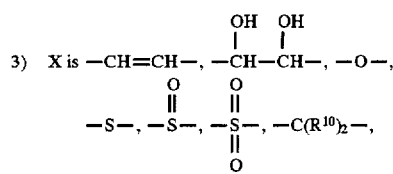

—C(=O)—, —C(=NOR$^{11}$)—, —C(OR$^{11}$)(R$^{11}$)—, —C(=O)CH(R$^{15}$)—, —CH(R$^{15}$)C(=O)—, —C(=NOR$^{11}$)CH(R$^{15}$)—, —CH(R$^{15}$)C(=NOR$^{11}$)—, —CH$_2$Z—, —Z—CH$_2$—, —CH$_2$ZCH$_2$—, where Z is

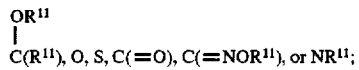

g) A$^1$ and A$^2$ together are each independently H, H; H, —OR$^{11}$; H, —SR$^{11}$; H, —N(R$^{11}$)$_2$; or together represent =S or =NR$^{11}$; B$^1$ and B$^2$ together represent O; and each R$^1$, R$^2$, R$^3$, R$^4$, R$^5$, R$^6$ and X are as defined in c), d), e), and f), above; or h) A$^1$ and A$^2$ together represent O, and B$^1$ and B$^2$ together are each independently H, H; H, —OR$^{11}$, H, —SR$^{11}$, H, —N(R$^{11}$)$_2$, or together represent =S or =NR$^{11}$; and each R$^1$, R$^2$, R$^3$, R$^4$, R$^5$, R$^6$ and X are as defined in c), d), e), and f), above.

B. Formula I

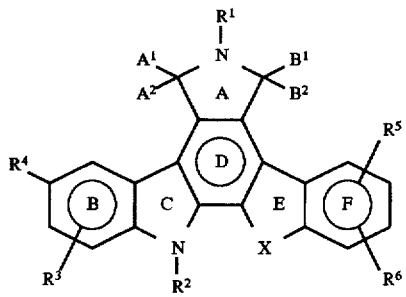

wherein:
a) A$^1$ and A$^2$ together represent O, and B$^1$ and B$^2$ together represent O;
b) R$^1$ is H, alkyl of 1-4 carbons (inclusive), aryl, arylalkyl, heteroaryl, and heteroarylalkyl; COR$^9$, where R$^9$ is alkyl of 1-4 carbons (inclusive), or aryl, preferably phenyl or naphthyl; —OR$^{10}$, where R$^{10}$ is H or alkyl of 1-4 carbons (inclusive); —CONH$_2$, —NR$^7$R$^8$, —(CH$_2$)$_n$NR$^7$R$^8$, where n is an integer of 1-4 (inclusive); or —O(CH$_2$)$_n$NR$^7$R$^8$; and either 1) R$^7$ and R$^8$ independently are H or alkyl of 1-4 carbons (inclusive); or
2) R$^7$ and R$^8$ are combined together to form a linking group of the general formula —(CH$_2$)$_2$—X$^1$—(CH$_2$)$_2$—, where X$^1$ is O, S or CH$_2$;

c) R$^2$ is H, —SO$_2$R$^9$; —CO$_2$R$^9$, —COR$^9$, alkyl of 1-8 carbons (inclusive), preferably an alkyl of 1-4 carbons (inclusive), alkenyl of 1-8 carbons (inclusive), preferably an alkenyl of 1-4 carbons (inclusive), or alkynyl of 1-8 carbons (inclusive), preferably an alkynyl of 1-4 carbons (inclusive); or a monosaccharide of 5-7 carbons (inclusive) where each hydroxyl group of the monosaccharide independently is either

7 or is replaced by H, alkyl of 1–4 carbons (inclusive), alkylcarbonyloxy of 2–5 carbons (inclusive) or alkoxy of 1–4 carbons (inclusive); and either
  1) each alkyl of 1–8 carbons (inclusive), alkenyl of 1–8 carbons (inclusive), or alkynyl of 1–8 carbons (inclusive) is unsubstituted; or
  2) each alkyl of 1–8 carbons (inclusive), alkenyl of 1–8 carbons (inclusive), or alkynyl of 1–8 carbons (inclusive) independently is substituted with 1–3 aryl of 6–10 carbons (inclusive), preferably phenyl or naphthyl; heteroaryl, F, Cl, Br, I, —CN, —NO$_2$, OH, —OR$^9$, —O(CH$_2$)$_n$NR$^7$R$^8$, —OCOR$^9$, —OCONHR$^9$, O-tetrahydropyranyl, NH$_2$, —NR$^7$R$^8$, —NR$^{10}$COR$^9$; —NR$^{10}$CO$_2$R$^9$, —NR$^{10}$CONR$^7$R$^8$, —NHC(=NH)NH$_2$, —NR$^{10}$SO$_2$R$^9$, —S(O)$_y$R$^{11}$, where R$^{11}$ is H or alkyl of 1–4 carbons, aryl of 6–10 carbons, preferably phenyl or naphthyl, or heteroaryl and y is 1 or 2; —SR$^{11}$, CO$_2$R$^9$, —CONR$^7$R$^8$, —CHO, COR$^9$, —CH$_2$OR$^7$, —CH=NNR$^{11}$R$^{12}$, —CH=NOR$^{11}$, —CH=NR$^9$, —CH=NNHCH(N=NH)NH$_2$, —SO$_2$NR$^{12}$R$^{13}$, —PO(OR$^{11}$)$_2$, or OR$^{14}$ where R$^{14}$ is the residue of an amino acid after the hydroxyl group of the carboxyl group is removed; and either
    i) R$^{12}$ and R$^{13}$ independently are H, alkyl of 1–4 carbons (inclusive), aryl of 6–10 carbons, preferably phenyl or naphthyl, or heteroaryl; or
    ii) R$^{12}$ and R$^{13}$ are combined together to form a linking group, preferably —(CH$_2$)$_2$—X$^1$—(CH$_2$)$_2$;
d) each R$^3$, R$^4$, R$^5$ and R$^6$, independently is H, aryl, preferably an aryl of 6–10 carbons (inclusive), more preferably phenyl or naphthyl; heteroaryl; F, Cl, Br, I, —CN, CF$_3$, —NO$_2$, OH, —OR$^9$, —O(CH$_2$)$_n$NR$^7$R$^8$, —OCOR$^9$, —OCONHR$^9$, NH$_2$, —CH$_2$OH, —CH$_2$OR$^{14}$, —NR$^7$R$^8$, —NR$^{10}$COR$^9$, —NR$^{10}$CONR$^7$R$^8$, —SR$^{11}$, —S(O)$_y$R$^{11}$ where y is 1 or 2; —CO$_2$R$^9$, —COR$^9$, —CONR$^7$R$^8$, —CHO, —CH=NOR$^{11}$, —CH=NR$^9$, —CH=NNR$^{11}$R$^{12}$, —(CH$_2$)$_n$SR$^9$, where n is an integer of 1–4 (inclusive), —(CH$_2$)$_n$S(O)$_y$R$^9$, —CH$_2$SR$^{15}$ where R$^{15}$ is alkyl of 1–4 carbons (inclusive); —CH$_2$S(O)$_y$R$^{14}$, —(CH$_2$)$_n$NR$^7$R$^8$, —(CH$_2$)$_n$NHR$^{14}$, alkyl of 1–8 carbons (inclusive), preferably alkyl of 1–4 carbons (inclusive); alkenyl of 1–8 carbons (inclusive), preferably alkenyl of 1–4 carbons (inclusive); alkynyl of 1–8 carbons (inclusive), preferably alkynyl of 1–4 carbons (inclusive); and either
  1) each alkyl of 1–8 carbons (inclusive), alkenyl of 1–8 carbons (inclusive) or alkynyl of 1–8 carbons (inclusive) is unsubstituted; or
  2) each alkyl of 1–8 carbons (inclusive), alkenyl of 1–8 carbons (inclusive) or alkynyl of 1–8 carbons (inclusive) is substituted as described in c)2), above;
e) X is either
  1) an unsubstituted alkylene of 1–3 carbons (inclusive); or
  2) X is an alkylene of 1–3 carbons (inclusive) substituted with one R$^2$ group, preferably OR$^{10}$, —SR$^{10}$, R$^{15}$, where R$^{15}$ is an alkyl of 1–4 carbons (inclusive); phenyl, naphthyl, arylalkyl of 7–14 carbons (inclusive), preferably benzyl; or
  3) X is —CH=CH—, —CH(OH)—CH(OH)—, —O—, —S—, —S(=O)—, —S(=O)$_2$—, —C(=O)—, —C(=NOR$^{11}$)—, —C(OR$^{11}$)(R$^{11}$)—, —C(=O)CH(R$^{15}$)—, —CH(R$^{15}$)C(=O)—, —C(R$^{10}$)$_2$—, —C(=NOR$^{11}$)CH(R$^{15}$)—, —CH

8

(R$^{15}$)C(=NOR$^{11}$)—, —CH$_2$Z—, —Z—CH$_2$—, —CH$_2$ZCH$_2$—, where Z is C(R$^{11}$)(OR$^{11}$), O, S, C(=O), C(=NOR$^{11}$), or NR$^{11}$;

or f) A$^1$ and A$^2$ together are each independently H, H; H, —OR$^{11}$; H, —SR$^{11}$; H, —N(R$^{11}$)$_2$; or together represent =S or =NR$^{11}$; B$^1$ and B$^2$ together represent O; and each R$^1$, R$^2$, R$^3$, R$^4$, R$^5$, R$^6$ and X are as defined in b), c), d), and e), above;

or g) A$^1$ and A$^2$ together represent O, and B$^1$ and B$^2$ together are each independently H, H; H, —OR$^{11}$, H, —SR$^{11}$, H, —N(R$^{11}$)$_2$, or together represent =S or =NR$^{11}$; and each R$^1$, R$^2$, R$^3$, R$^4$, R$^5$, R$^6$ and X are as defined in b), c), d), and e), above.

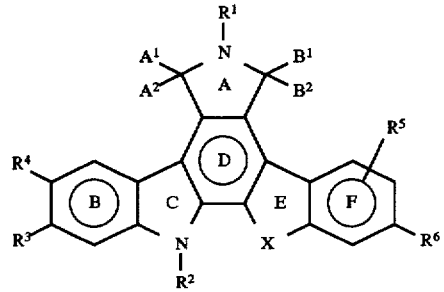

Formula Ia

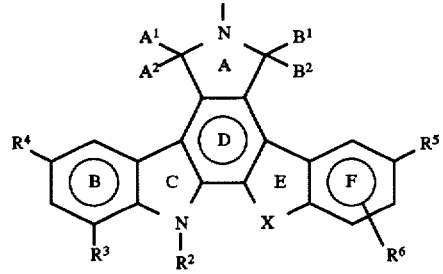

Formula Ib wherein:
a) A$^1$ and A$^2$ together represent O, and B$^1$ and B$^2$ together represent O;
b) R$^1$ is H;
c) R$^2$ is H, allyl, hydroxyethyl, or alkyl of 1–4 carbons (inclusive), preferably methyl;
d) each R$^3$, R$^4$, R$^5$, and R$^6$, independently is H, F, Cl, Br, I, alkyl of 1–4 carbons (inclusive), preferably methyl, alkoxyl of 1–4 carbons (inclusive), preferably methoxyl, heteroarylalkenyl, preferably pyridylvinyl, heteroarylalkyl, preferably pyridylethyl, cyanoethyl, cyanovinyl, aryl of 6–10 carbons, preferably phenyl, alkynyl, arylalkenyl, preferably styryl, alkoxycarbonylalkenyl, preferably ethoxycarbonylvinyl, or haloalkenyl;
e) X is either
  1) an unsubstituted alkylene of 1–3 carbons (inclusive), preferably —CH$_2$—, or —CH$_2$CH$_2$—; or
  2) X is an alkylene of 1–3 carbons (inclusive) preferably —CH$_2$—, or —CH$_2$CH$_2$—, wherein each alkylene of 1–3 carbons (inclusive) is substituted with one R$^2$ group, preferably —OR$^{11}$, —SR$^{11}$, R$^{15}$; phenyl, naphthyl, arylalkyl of 7–11 carbons (inclusive), preferably benzyl; or
  3) X is —CH=CH—, —CH(OH)CH(OH)—, —O—, —S—, —S(=O)—, —S(=O)$_2$—, —C(=O)—, —C(=NOR$^{11}$)—, —C(OR$^{11}$)(R$^{11}$)—, —C(=O)

$CH(R^{15})$—, —$CH(R^{15})C(=O)$—, —$C(R^{10})_2$—, —$C(=NOR^{11})CH(R^{15})$—, —$CH(R^{15})C(=NOR^{11})$—, —$CH_2Z$—, —$Z$—$CH_2$—, —$CH_2ZCH_2$—, where Z is $C(R^{11})(OR^{11})$, O, S, C(=O), C(=NOR^{11}), or $NR^{11}$;

f) $A^1$ and $A^2$, together are each independently H,H or H,OH and $B^1$ and $B^2$ together represent O; and each $R^1$, $R^2$, $R^3$, $R^4$, $R^5$, $R^6$ and X are as defined in b), c), d), and e), above;

or g) $A^1$ and $A^2$ together represent O, and $B^1$ and $B^2$ together are each independently H,H or H,OH; and each $R^1$, $R^2$, $R^3$, $R^4$, $R^5$, $R^6$ and X are as defined in b), c), d), and e), above.

As used herein with reference to the definition of $R^{14}$, the term "amino acid" denotes a molecule containing both an amino acid group and a carboxyl group. It includes an "α-amino acid" which has its usual meaning as a carboxylic acid which bears an amino functionality on the carbon adjacent to the carboxyl group. α-Amino acids can be naturally occurring or non-naturally occurring. Amino acids also include "dipeptides" which are defined herein as two amino acids which are joined in a peptide linkage Thus constituents of dipeptides are not limited to α-amino acids, and can be any molecule containing both an amino group and a carboxyl group. Preferred are α-amino acids, dipeptides such as lysyl-β-alanine, and aminoalkanoic acids of 2–8 carbons, e.g., 3-dimethylaminobutyric acid.

Preferred embodiments of the fused pyrrolocarbazoles are those represented by Formulae I, Ia and Ib in Table I, where the following substitutions are made (Roman numerals indicate the Formula representation):

TABLE I

| Compound[1] | $A^1A^{2(2)}$ | $B^1B^{2(3)}$ | $R^2$ | $R^3$ | $R^4$ | X |
|---|---|---|---|---|---|---|
| I-1 | O | O | H | H | H | CH₂ |
| I-2 | H,H | O | H | H | H | CH₂ |
| I-3 | O | H,H | H | H | H | CH₂ |
| I-4 | O | O | CH₃ | H | H | CH₂ |
| I-5[4] | — | — | CH₃ | H | H | CH₂ |
| I-6 | O | O | H | H | Br | CH₂ |
| I-7 | O | O | H | H | F | CH₂ |
| I-8[5] | — | — | H | H | F | CH₂ |
| Ia-1 | O | O | H | Cl | H | CH₂ |
| Ia-2[6] | — | — | H | Cl | H | CH₂ |
| I-9 | H,H | O | H | H | Br | CH₂ |
| Ib-1 | O | O | H | CH₃ | H | CH₂ |
| I-10 | O | O | H | H | Cl | CH₂ |
| I-11 | O | H,H | H | H | Br | CH₂ |
| I-12 | H,H | O | H | H | F | CH₂ |
| I-13 | H,H | O | H | H | OCH₃ | CH₂ |
| Ia-3[7] | O | O | H | H | H | CH₂ |
| Ib-2[8] | O | O | H | H | H | CH₂ |
| I-14 | O | O | H | H | H | CH₂CH₂ |
| I-15 | O | O | H | H | H | CH=CH |
| I-16 | O | H,H | H | H | H | CH₂CH₂ |
| I-17 | H,H | O | H | H | H | CH₂CH₂ |
| I-18 | O | H,H | H | Br | H | CH₂CH₂ |
| I-19 | H,H | O | H | Br | H | CH₂CH₂ |
| I-20 | O | O | H | H | H | S |
| I-21 | O | O | H | H | H | O |
| I-22 | O | H,H | H | H | F | CH₂CH₂ |
| I-23 | O | H,H | H | H | F | CH₂ |
| I-24 | H,H | O | H | H | HC=CHC₆H₅ | CH₂ |
| I-25 | H,H | O | H | H | HC=CHCO₂C₂H₅ | CH₂ |
| I-26 | H,H | O | CH₂CH=CH₂ | H | H | CH₂ |
| I-27 | H,H | O | H | H | C₆H₅ | CH₂ |
| I-28 | O | O | H | H | H | CO |
| I-29 | H,H | O | CH₂CH₂OH | H | H | CH₂ |
| I-30 | O | H,OH | H | H | H | CO |
| I-31 | H,OH | O | H | H | H | CO |
| I-32[12] | H,H | O | H | H | HC=CH-2-pyr | CH₂ |
| Ia-4[9] | O | O | H | H | H | CH₂CH₂ |
| I-33 | H,H | O | H | H | HC=CH-4-pyr | CH₂ |
| I-34 | H,H | O | H | H | H₂CCH₂-2-pyr | CH₂ |
| I-35 | H,H | O | H | H | HC=CHCN | CH₂ |
| I-36 | H,H | O | H | H | C≡CH | CH₂ |
| I-37 | O | O | H | H | (CH₂)₄CH₃ | CH₂ |
| Ia-5[7] | O | O | H | H | H | CH₂CH₂ |
| Ia-6[10] | O | O | H | H | H | CH₂CH₂ |
| Ia-7[11] | O | O | H | H | H | CH₂CH₂ |
| I-38 | H,OH | O | H | H | H | CH=CH |
| I-39 | H,H | O | H | H | HC=CH-2-phthalimide | CH₂ |
| I-40 | H,H | O | | | Iodo | CH₂ |
| I-41 | O | H,H | H | H | HC=CH-2-pyr | CH₂ |
| I-42 | O | H,H | H | H | H | S |
| I-43 | H,H | O | H | H | H | S |
| I-44 | H,H | O | H | H | CH=CHI | CH₂ |

[1]$R^1$, $R^5$, and $R^6$ are each H except where noted.

TABLE I-continued

| Compound[1] | A¹A²[2] | B¹B²[3] | R² | R³ | R⁴ | X |
|---|---|---|---|---|---|---|

[2]A¹ and A² are H,H; H,OH; or both are combined together to represent oxygen, where indicated.
[3]B¹ and B² are H,H; H,OH; or both are combined together to represent oxygen, where indicated.
[4]Compound I-5 is a mixture of compounds in a 5/1 molar ratio where A¹A² = H,H; B¹B² = O/A¹A² = O; B¹B² = H,H.
[5]Compound I-8 is a mixture of compounds in a 2/1 molar ratio where A¹A² = H,H; B¹B² = O/A¹A² = O; B¹B² = H,H.
[6]Compound II-12 is a mixture of compounds in a 4/1 molar ratio where A¹A² = H,H; B¹B² = O/A¹A² = O; B¹B² = H,H.
[7]R⁶ = Br.
[8]R⁵ = Br.
[9]R⁶ = F
[10]R⁶ = 2-pyridylvinyl
[11]R⁶ = 2-pyridylethyl
[12]2-pyr = 2-pyridyl Particularly preferred compounds of Table I include compounds I-1, I-2, I-3, I-4, I-6, I-7, I-9, I-11, I-12, I-14, I-15, I-16, I-17, I-22, I-23, I-26, I-29, I-32, I-34, I-39, I-42 and I-43, with compounds I-34 and I-32 being most preferred.

Pharmaceutically acceptable salts of the fused pyrrolocarbazoles also fall within the scope of the compounds as disclosed herein. The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable ammonium salts are ammonium salt and tetramethylammonium salt. Examples of pharmaceutically acceptable organic amine addition salts are salts with morpholine and piperidine. Examples of pharmaceutically acceptable amino acid addition salts are salts with lysine, glycine, and phenylalanine.

Compounds provided herein can be formulated into pharmaceutical compositions by admixture with pharmaceutically acceptable nontoxic excipients and carriers. As noted above, such compositions may be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, trans-dermal patches.

The composition may conveniently be administered in unit dosage form and may be prepared by any of the methods well known in the pharmaceutical art, for example, as described in Remington's Pharmaceutical Sciences (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for transdermal patches are preferably lipophilic emulsions.

The materials of this invention can be employed as the sole active agent in a pharmaceutical or can be used in combination with other active ingredients, e.g., other growth factors which could facilitate neuronal survival or axonal regeneration in diseases or disorders.

The concentrations of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in an aqueous physiological buffer solution containing about 0.1 to 10% w/v compound for parenteral administration. Typical dose ranges are from about 1 µg/kg to about 1 g/kg of body weight per day; a preferred dose range is from about 0.01 mg/kg to 100 mg/kg of body weight per day. The preferred dosage of drug to be administered is likely to depend on such variables as the type and extent of progression of the disease or disorder, the overall health status of the particular patient, the relative biological efficacy of the compound selected, and formulation of the compound excipient, and its route of administration.

III. Fused Pyrrolocarbazole Utilities

Our fused pyrrolocarbazoles have evidenced a panapoly of important functional pharmacological activities which find utility in a variety of settings, including both research and therapeutic arenas. For ease of presentation, and in order not to limit the range of utilities for which these compounds can be characterized, we generally describe the activities of the fused pyrrolocarbazoles as follows:

A. Effect on the function and/or survival of trophic factor responsive cells
B. Inhibition of enzymatic activity
C. Inhibition of inflammation-associated responses
D. Inhibition of cell growth associated with hyperproliferative states
E. Inhibition of developmentally programmed motoneuron death Effect on the function and/or survival of trophic factor responsive cells, e.g., cells of a neuronal lineage, can be established using any of the following assays: (1) cultured spinal cord choline acetyltransferase ("ChAT") assay; (2) cultured dorsal root ganglion ("DRG") neurite extension assay; (3) cultured basal forebrain neuron ("BFN") ChAT activity assay. Inhibition of enzymatic activity can be determined using PKC inhibition and trk tyrosine kinase inhibition assays. Inhibition of inflammation-associated response can be established using an indoleamine 2,3-dioxygenase ("IDO") mRNA assay. Inhibition of cell growth associated with hyperproliferative states can be determined by measuring the growth of cell lines of interest, such as an AT2 line in the case of prostate cancer. Inhibition of developmentally programmed motoneuron death can be assessed in ovo using embryonic chick somatic motoneurons, which cells undergo naturally occurring death between embryonic days 6 and 10, and analyzing inhibition of such naturally occurring cell death as mediated by the compounds disclosed herein.

As used herein, the term "effect" when used to modify the terms "function" and "survival" means a positive or negative alteration or change. An effect which is positive can be referred to herein as an "enhancement" or "enhancing" and an effect which is negative can be referred to herein as "inhibition" or "inhibiting."

As used herein, the terms "enhance" or "enhancing" when used to modify the terms "function" or "survival" means that the presence of a fused pyrrolocarbazole has a positive effect on the function and/or survival of a trophic factor responsive cell compared with a cell in the absence of the fused pyrrolocarbazole. For example, and not by way of limitation, with respect to the survival of, e.g., a cholinergic neuron, the fused pyrrolocarbazole would evidence enhancement of survival of a cholinergic neuronal population at risk of dying (due to, e.g., injury, a disease condition, a degenerative condition or natural progression) when compared to a cholinergic neuronal population not presented with such fused pyrrolocarbazole, if the treated population has a comparatively greater period of functionality than the non-treated population. As a further example, and again not by way of limitation, with respect to the function of, e.g., a sensory neuron, the fused pyrrolocarbazole would evidence enhancement of the function (e.g. neurite extension) of a sensory neuronal population when compared to a sensory neuronal population not presented with such fused pyrrolocarbazole, if the neurite extension of the treated population is comparatively greater than the neurite extension of the non-treated population.

As used herein, "inhibit" and "inhibition" mean that a specified response of a designated material (e.g., enzymatic activity) is comparatively decreased in the presence of a fused pyrrolocarbazole.

As used herein the term "neuron," "cell of neuronal lineage" and "neuronal cell" includes, but is not limited to, a heterogeneous population of neuronal types having singular or multiple transmitters and/or singular or multiple functions; preferably, these are cholinergic and sensory neurons. As used herein, the phrase "cholinergic neuron" means neurons of the Central Nervous System (CNS) and Peripheral Nervous System (PNS) whose neurotransmitter is acetylcholine; exemplary are basal forebrain and spinal cord neurons. As used herein, the phrase "sensory neuron" includes neurons responsive to environmental cues (e.g., temperature, movement) from, e.g., skin, muscle and joints; exemplary is a neuron from the DRG.

As used herein a "trophic factor" is a molecule that directly or indirectly affects the survival or function of a trophic factor responsive cell. Exemplary trophic factors include Ciliary Neurotrophic Factor (CNTF), basic Fibroblast Growth Factor (bFGF), insulin and insulin-like growth factors (e.g., IGF-I, IGF-II, IGF-III), interferons, interleukins, cytokines, and the neurotrophins, including Nerve Growth Factor (NGF), Neurotrophin-3 (NT-3), Neurotrophin-4/5 (NT-4/5) and Brain Derived Neurotrophic Factor (BDNF).

A "trophic factor-responsive cell," as defined herein, is a cell which includes a receptor to which a trophic factor can specifically bind; examples include neurons (e.g., cholinergic and sensory neurons) and non-neuronal cells (e.g., monocytes and neoplastic cells).

As used herein, "trophic factor activity" and "trophic factor induced activity" are defined as any response which directly or indirectly results from the binding of a trophic factor (e.g., NGF) to a cell comprising a trophic factor receptor (e.g., neuron comprising of a trk). In the case of, e.g., NGF binding with trk, an exemplary response would include autophosphorylation of trk tyrosine residues leading to increased ChAT activity which results in enhanced neuron survival, and/or function.

As used herein, the term "trk" refers to the family of high affinity neurotrophin receptors presently comprising trk A, trk B and trk C, and other membrane associated proteins to which a neurotrophin can bind.

As used in the phrases "trophic factor activity" and "trophic factor-induced activity," the term "trophic factor" includes both endogenous and exogenous trophic factors, where "endogenous" refers to a trophic factor normally present and "exogenous" refers to a trophic factor added to a system. As defined, "trophic factor induced activity" includes activity induced by (1) endogenous trophic factors; (2) exogenous trophic factors; and (3) a combination of endogenous and exogenous trophic factors.

As used herein the phrase "hyperproliferative state" in reference to the term "cells" means cells whose unregulated and/or abnormal growth can lead to the development of an unwanted condition, for example, a cancerous condition or a psoriatic condition.

As used herein, "cancer" and "cancerous" refer to any malignant proliferation of cells in a mammal. Examples include prostate, benign prostate hyperplasia, ovarian, breast and other recognized cancers. As used herein the term "psoriasis" and "psoriatic condition" refer to disorders involving keratinocyte hyperproliferation, inflammatory cell infiltration and cytokine alteration.

As used herein, the phrase "at risk of dying" in conjunction with a biological material, e.g., a cell such as a neuron, means a state or condition which negatively impacts the biological material such that the material has an increased likelihood of dying due to such state or condition. For example, in Example III (E)(1) we demonstrate that compounds disclosed herein can "rescue" or enhance the survival of motoneurons which are naturally at risk of dying in an in ovo model of programmed cell death. Similarly, for example, a neuron may be at risk of dying due to the natural aging process which occasions the death of a neuron, or due to an injury, such as a trauma to the head, which may be such that neurons and/or glia, for example, impacted by such trauma may be at risk of dying. Further, for example, a neuron may be at risk of dying due to a disease state or condition, as in the case of neurons at risk of dying as occasioned by the disease ALS. Thus, by enhancing the survival of a cell at risk of dying by use of a compound of the claimed invention is meant that such compound decreases or prevents the risk of the death of the cell.

As used herein the term "contacting" means directly or indirectly causing placement together of moieties, such that the moieties directly or indirectly come into physical association with each other, whereby a desired outcome is achieved. Thus, as used herein, one can "contact" a target cell with a compound as disclosed herein even though the compound and cell do not necessarily physically join together (as, for example, is the case where a ligand and a receptor physically join together), as long as the desired outcome is achieved (e.g., enhancement of the survival of the cell). Contacting thus includes acts such as placing moieties together in a container (e.g., adding a compound as disclosed herein to a container comprising cells for in vitro studies) as well as administration of the compound to a target entity (e.g., injecting a compound as disclosed herein into a laboratory animal for in vivo testing, or into a human for therapy or treatment purposes).

A. Effect on the function and/or survival of trophic factor responsive cells

The disclosed fused pyrrolocarbazoles can be used to enhance the function and/or survival of cells of neuronal lineage. In this context, the fused pyrrolocarbazoles can be utilized individually or with other fused pyrrolocarbazoles, or in combination with other beneficial molecules such as indolocarbazoles which also evidence the ability to effect the function and/or survival of a designated cell. In situations where the fused pyrrolocarbazole is intended to enhance, e.g., neurotrophin activity, exogenous neurotrophins may be utilized in conjunction with the fused pyrrocarbazole.

A variety of neurological disorders are characterized by neuronal cells which are dying, injured, functionally comprised, undergoing axonal degeneration, at risk of dying, etc. These disorders include, but are not limited to: Alzheimer's; motor neuron disorders (e.g. amyotrophic lateral sclerosis); Parkinson's; cerebrovascular disorders (e.g., stroke, ischaemia); Huntington's; AIDS dementia; epilepsy; multiple sclerosis; peripheral neuropathies (e.g., those affecting DRG neurons in chemotherapy-associated peripheral neuropathy) including diabetic neuropathy; disorders induced by excitatory amino acids; disorders associated with concussive or penetrating injuries of the brain or spinal cord.

As set forth in the Examples of this section of the disclosure, the ability of a fused pyrrolocarbazole to enhance the function and/or survival of cells of a neuronal lineage can be determined by employing any of the following assays:

1. Spinal Cord ChAT Activity Assay
2. Basal Forebrain ChAT Activity Assay
3. DRG Neurite Outgrowth Assay
4. Enhancement of Neurotrophin Activity Assay ChAT catalyzes the synthesis of the neurotransmitter acetylcholine and is considered an enzymatic marker for a functional cholinergic neuron. A functional neuron is also capable of survival. Neuron survival is assayed by quantitation of the specific uptake and enzymatic conversion of a dye (e.g., calcein AM) by living neurons. Neurotrophins activate the kinase activity of a trk, for example, trkA, in cells such as sensory or cholinergic neurons. Enhancement of a neurotrophin such as NT-3 can be determined by comparing the functional activity of the neurotrophin with or without the fused pyrrolocarbazole present.

Because of their varied utilities, the fused pyrrolocarbazoles disclosed herein find utility in a variety of settings. The compounds can be used in the development of in vitro models of neuronal cell survival, function, identification, or for the screening of other synthetic compounds which have activities similar to that of the fused pyrrolocarbazoles. The compounds can be utilized in a research environment to investigate, define and determine molecular targets associated with functional responses. For example, by radiolabelling a fused pyrrolocarbazole associated with a specific cellular function (e.g., mitogenesis), the target entity to which the fused pyrrolocarbazole binds can be identified, isolated, and purified for characterization. In yet another example, a fused pyrrolocarbazole can be used as a screening tool to discover agents which have marginal trophic factor-like activity, but when combined with at least one disclosed fused pyrrolocarbazole, are capable of enhancing the trophic factor-induced activity of a trophic factor-responsive cell.

Degeneration, death or non-functioning of neurons is a feature of many human neurological disorders, including, but not limited to, Alzheimer's; motor neuron disorders (e.g., ALS); Parkinson's; cerebrovascular disorders (e.g., stroke, ischaemia); Huntington's; AIDS dementia; epilepsy; multiple sclerosis; concussive or penetrating injuries of the brain or spinal cord; peripheral neuropathies (e.g., those affecting DRG in chemotherapy-associated peripheral neuropathy); and disorders induced by excitatory amino acids. Because the disclosed fused pyrrolocarbazoles are useful in enhancing trophic factor-induced activities of trophic factor responsive cells (e.g., cholinergic and sensory neurons), the disclosed compounds beneficially lend themselves to a pharmacological activity utility as therapeutic agents. Thus, because the disclosed compounds have evidenced utility in, e.g., enhancement of ChAT activity or DRG neuron survival, the utility of the compounds in the treatment of disorders associated with, e.g., decreased ChAT activity or the death of DRG neurons, is within the scope of this invention.

EXAMPLE III(A)(1)

Enhancement of Spinal Cord ChAT Activity

As noted, ChAT is a specific biochemical marker for functional cholinergic neurons. Cholinergic neurons represent the major cholinergic input into the hippocampal formation, olfactory nucleus, interpeduncular nucleus, cortex, amygdala, and parts of the thalamus. In the spinal cord, the motor neurons are cholinergic neurons which contain ChAT (Phelps et al., *J. Comp. Neurol.* 273:459–472 (1988)). ChAT activity has been used to study the effects of neurotrophins (e.g., NGF or NT-3) on the survival and/or function of cholinergic neurons. The ChAT assay also serves as an indication of the regulation of ChAT levels within cholinergic neurons.

Fused pyrrolocarbazoles increased ChAT activity in the dissociated rat embryonic spinal cord culture assay (Table II). For example, Compound I-13 increased ChAT activity 217% over control cultures (not treated with the fused pyrrolocarbazole) after allowing a 2–3 hour plating period for cells to attach to control tissue culture wells. In these assays, a fused pyrrolocarbazole was directly added to a dissociated spinal cord culture. Compounds of the invention increased spinal cord ChAT activity in a concentration-dependent manner. Compounds which increased ChAT activity at least 120% of the control activity were considered active. Increased ChAT activity was observed after a single application of a fused pyrrolocarbazole. The fused pyrrolocarbazole was added on the same day the dissociated spinal cord cell culture was initiated. Increased ChAT activity was detectable 48 hours later.

TABLE II

Effect of Fused Pyrrolocarbazoles on Spinal Cord ChAT Activity

| Compound # | % of Control, untreated cultures |
| --- | --- |
| I-4 | 124 |
| I-5 | 137 |

TABLE II-continued

Effect of Fused Pyrrolocarbazoles on Spinal Cord ChAT Activity

| Compound # | % of Control, untreated cultures |
|---|---|
| I-1 | 148 |
| I-6 | 209 |
| I-7 | 164 |
| I-8 | 200 |
| I-2 | 160 |
| Ia-1 | 139 |
| Ia-2 | 161 |
| I-9 | 185 |
| Ib-1 | 138 |
| I-3 | 174 |
| I-10 | 189 |
| I-11 | 188 |
| Ia-3 | 138 |
| Ib-2 | 153 |
| I-12 | 173 |
| I-14 | 153 |
| I-13 | 217 |
| I-15 | 182 |
| I-20 | 130 |
| I-16 | 142 |
| I-17 | 197 |
| I-18 | 133 |
| I-22 | 143 |
| I-19 | 203 |
| I-21 | 122 |
| I-24 | 236 |
| I-25 | 168 |
| I-26 | 167 |
| I-23 | 208 |
| I-29 | 154 |
| I-28 | <120 |
| I-27 | 120 |
| I-32 | 288 |
| I-30,31 | 132 |
| Ia-4 | <120 |
| I-33 | 144 |
| I-34 | 254 |
| I-35 | 121 |
| I-36 | 167 |
| I-37 | <120 |
| Ia-5 | 132 |
| Ia-6 | 139 |
| Ia-7 | <120 |
| I-38 | 208 |
| I-39 | 268 |
| I-40 | 150 |
| I-41 | 122 |
| I-42 | 177 |
| I-43 | 138 |
| I-44 | 127 |

Methods: Fetal rat spinal cord cells were dissociated, and experiments were performed as described (Smith et al., *J. Cell Biology* 101:1608–1621 (1985); Glicksman et al., *J. Neurochem.* 61:210–221 (1993)). Dissociated cells were prepared from spinal cords dissected from rats (embryonic day 14–15) by standard trypsin dissociation techniques (Smith et al., *J. Cell Biology* 10:1608–1621 (1985)). Cells were plated at $6\times10^5$ cells/cm$^2$ on poly-1-ornithine coated plastic tissue culture wells in serum-free N2 medium supplemented with 0.05% bovine serum albumin (BSA) (Bottenstein et al., *PNAS USA* 76:514–517 (1979)). Cultures were incubated at 37° C. in a humidified atmosphere of 5% $CO_2$/95% air for 48 hours. ChAT activity was measured after 2 days in vitro using a modification of the Fonnum procedure (Fonnum, *J. Neurochem.* 24:407–409 (1975)) according to McManaman et al. and Glicksman et al. (McManaman et al., *Developmental Biology* 125:311–320 (1988); Glicksman et al., *J. Neurochem.* 61:210–221 (1993)).

EXAMPLE III(A)(2)

Basal Forebrain ChAT Activity Assay

Fused pyrrolocarbazoles were tested for the ability to increase ChAT activity of basal forebrain cultures. Fused pyrrolocarbazoles were found to increase ChAT activity in basal forebrain cultures (Table III; "N.T."="not tested"). Control cultures did not receive a fused pyrrolocarbazole.

TABLE III

Fused Pyrrolocarbazoles Promote ChAT Activity in Basal Forebrain

| | ChAT Activity (% of Control) | | | |
|---|---|---|---|---|
| Compound | 100 nM | 250 nM | 500 nM | 1000 nM |
| I-1 | inactive | inactive | inactive | NT |
| I-2 | inactive | 137 | 137 | inactive |
| I-3 | inactive | inactive | 130 | NT |
| I-12 | 279 | 389 | NT | NT |
| I-24 | inactive | 151 | NT | NT |
| I-36 | 122 | 131 | 123 | inactive |
| I-29 | 140 | 189 | 194 | 210 |
| I-34 | inactive | 192 | inactive | inactive |

Methods: The basal forebrain was dissected from rat embryos (day 17 or 18 embryos) and the cells were dissociated with a neutral protease (Dispase™, Collaborative Research). Neurons were plated at a density of $5\times10^4$ cells/well ($1.5\times10^5$ cells/cm$^2$) in poly-1-ornithine and laminin coated plates. Cells were cultured in serum-free N2 medium containing 0.05% BSA at 37° C. in a humidified atmosphere, 5% $CO_2$/95% air. ChAT activity was assessed 5 days after plating by using the ChAT assay as described in Example III(A)(1).

EXAMPLE III(A)(3)

DRG Neurite Outgrowth Assay

Fused pyrrolocarbazoles promoted nerve fiber (i.e., neurite) outgrowth in explant (i.e., primary) cultures of chick dorsal root ganglion neurons. Dorsal root ganglion (i.e., DRG) nerve fiber outgrowth was increased when a fused pyrrolocarbazole was added to cultures at a concentration of 200 nM (Table IV). Control cultures consisted of: 1) no added NGF or fused pyrrolocarbazole ("Control"), or 2) 50 ng/ml NGF, a neurotrophin known to promote neurite extension in DRG cultures ("NGF").

TABLE IV

Fused Pyrrolocarbazoles Promote DRG Neurite Outgrowth

| Compound | Concentration 200 nM |
|---|---|
| Control | few sparse neurites visible |
| NGF | dense outgrowth of neurites that reaches the edges of the well |
| I-1 | modest number of neurites |
| I-2 | modest to dense outgrowth of neurites |
| I-3 | dense outgrowth of neurites but not quite reaching the edges of the well |

Methods: Dorsal root ganglia were dissected from chick embryos (embryonic day 9) and individual ganglia were plated on poly-1-ornithine and laminin coated plates. A fused pyrrolocarbazole or 50 ng/ml NGF was each added to independent cultures after allowing a 1–2 hour cell attachment period. Explants were cultured for 48 hours in serum-free N2 medium supplemented with 0.05% BSA (Bottenstein et al., PNAS USA 76:514–517 (1979)). Cultures were maintained at 37° C. in a humidified atmosphere, 5% $CO_2$/95% air. Nerve fiber outgrowth was assessed by the density and length of neurites. It should be apparent to those skilled in the art that neurite extension assays are semi-quantitative and involve a visual comparison between control and experimental neuronal cell cultures (Alberts et al., *Molecular Biology of the Cell*, 2ed. Garland Publishing, Inc., New York (1989).

EXAMPLE III(A)(4)

Enhancement of Neurotrophin Activity Assay

Fused pyrrolocarbazoles were tested for the ability to enhance the activity of the neurotrophin NT-3 in basal forebrain cultures. ChAT activity was assayed as a measure of cholinergic neuron function and survival. The concentration of NT-3 (100 ng/ml) used in these experiments increased ChAT activity over control cultures (untreated with NT-3 or a fused pyrrolocarbazole) by 40%. Compounds I-1, I-6, I-7, and Ia-1 each enhanced ChAT activity in the presence of a 100 ng/ml concentration of NT-3. When these compounds were each added alone to basal forebrain neurons in the absence of NT-3, there was no effect on ChAT activity. The increase in ChAT activity was greater than that elicited by NT-3 alone, as indicated in the bar-graph presented in FIG. 1.

Methods. Basal forebrain cultures were prepared from embryonic rats (embryonic day 17) and dissociated with the neutral protease Dispase™. Cells were plated at a density of $4 \times 10^5$ cells/cm$^2$ on poly-1-ornithine coated plastic tissue culture plates in a mixture of DMEM and F12 media (50/50 v/v GIBCO) supplemented with 5% horse serum and 0.5% fetal bovine serum. Cells were incubated at 37° C. in a humidified atmosphere of 5% $CO_2$/95% air for 5 days. ChAT activity was measured as described in

EXAMPLE III(A)(1).

Recombinant rat NT-3 was produced by using a recombinant baculovirus expression vector under the control of the polyhedron virus promoter (Fraser, In Vitro *Cell. and Dev. Biol.* 25:225–235 (1989)). The plasmid pXM-NT3 (Hallbook et al., Neuron 6:845–858 (1991), which contained the rat NT-3 cDNA clone, was provided by Dr. Ira Black (University of Medicine and Dentistry of New Jersey, Piscataway, N.J.). NT-3 cDNA was subcloned into the transfer vector pVL1392 (In Vitrogen Corp., San Diego, Calif.) for recombinant virus production. Recombinant baculovirus was produced as described in Meyer et al. (Meyer at al., *J. Neurochem* 62:825–833 (1994)).

EXAMPLE III(A)(5)

DRG Neuron Survival Assay

Fused pyrrolocarbazoles promoted dorsal root ganglion (DRG) neuronal survival in cultures of chick DRG neurons. Cell survival was measured by uptake of calcein AM, an analog of the viable dye, fluorescein diacetate. Calcein is taken up by viable cells and cleaved intracellularly to fluorescent salts which are retained by intact membranes of viable cells. Microscopic counts of viable neurons correlate directly with relative fluorscence values obtained with the fluorimetric viability assay. This method thus provides a reliable and quantitive measurement of cell survival in the total cell population of a given culture (Bozyczko-Coyne et al., *J. Neur. Meth.* 50:205–216, 1993).

Dorsal root ganglion neuronal survival was enhanced by fused pyrrolocarbazoles with activity being observed at 100–500 nM (Table V). All of these analogs were also active in increasing spinal cord ChAT activity (See Example III (A)(1), Table II). Microscopic examination of the dorsal root ganglion neurons stimulated with the six active compounds indicated enhanced nerve fiber outgrowth as well.

TABLE V

Fused Pyrrolocarbazoles Promote Survival of DRG Neurons

| Compound | Neuronal Survival (% of Control) | | |
|---|---|---|---|
| | 100 nM | 250 nM | 500 nM |
| I-12 | 126 | 165 | 178 |
| I-34 | 159 | 203 | 207 |
| I-24 | 154 | 167 | 163 |
| I-15 | inactive | 132 | inactive |
| I-32 | 173 | 164 | 151 |
| I-23 | inactive | 128 | 135 |

Methods: Dorsal root ganglia were dissected from embryonic age day 9 chick embryos and dissociated cells prepared by subsequent Dispase (neutral protease, Collaborative Research) dissociation. Neurons were seeded at low density ($3 \times 10^4$ cells/cm$^2$) into 96 well poly-L-ornithine and laminin coated plates. Cells were cultured for 48 hours in serum-free N2 medium (Bottenstein and Sato, 1979) at 37° C. in a humidified atmosphere, 5% $CO_2$/95% air. Cell survival was assessed at 48 hours using the viable fluorimetric assay described above.

B. Inhibition of Enzymatic Activity

The ability of the indolocarbazole K-252a, for example, to inhibit the enzymatic activity of protein kinase C ("PKC") is well known and documented. Inhibition of PKC activity has been suggested as an approach for inhibiting, mediating, reducing and/or preventing a variety of disease states, including inflammatory diseases, allergy and cancerous conditions, as indicated in the following representative references: U.S. Pat. Nos. 4,877,776, and 4,923,986; published European Patent Specification 558,962 (published Sep. 8, 1993 in the name of E. R. Squibb & Sons, Inc.); Tadka, T. et al., 170(3) *Biochem. Biophys. Res. Comm.* 1151, 1980). The tyrosine kinases, of which trk is a member, are enzymes which catalyze the transfer of the γ-phosphate of ATP to the hydroxyl group oftyrosine on many key proteins. Activated protein tyrosine kinases have been identified as the products of approximately half of known oncogenes (see Chang, C.J. & Geahlen, R. L. 55(11) *J. Nat. Prods.* 1529, 1992). Inhibiting, mediating, reducing and/or preventing a variety of cancerous conditions via inhibition of protein kinases has been set forth (see Chang, C.J., supra).

Because of the important association between protein kinase activity and certain diseases and disorders, our fused pyrrolocarbazoles also find utility in both research and therapeutic settings. For example, in a research environment, the compounds can be used in the development of assays and models for further enhancement of the understanding of the roles that inhibition of protein kinase (e.g., PKC, trk tyrosine kinase) play in the mechanistic aspects of the associated disorders and diseases. In a therapeutic setting, the compounds which inhibit these enzymatic activities can be used to inhibit the deleterious consequences of these enzymes with respect to disorders such as cancer.

As we demonstrate in the Examples of this section, inhibition of enzymatic activity using our fused pyrrolocarbazoles can be determined using the following assays:

1. PKC Activity Inhibition Assay
2. trkA Tyrosine Kinase Activity Inhibition Assay

EXAMPLE III(B)(1)

PKC Activity Inhibition Assay

Fused pyrrolocarbazoles inhibited the activity of protein kinase C (Table VI). The protein kinase C assay has been disclosed (Murakata et al., U.S. Pat. No. 4,923,986; Kikkawa et al., *J. Biol. Chem.* 257:13341-13348 (1982)). The assay was performed with several concentrations of fused pyrrolocarbazoles. The concentration at which protein kinase C was 50% inhibited ($IC_{50}$) was determined.

TABLE VI

Protein Kinase C Inhibition

| COMPOUND | PKC INHIBITION $IC_{50}$ ($\mu$M) |
|---|---|
| I-1 | 0.07 |
| I-6 | 1.0 |
| I-7 | 0.15 |
| I-2 | 0.11 |
| I-9 | 4.5 |
| I-3 | 0.1 |
| I-11 | 0.45 |
| I-12 | 0.085 |
| I-14 | 0.015 |
| I-15 | 0.05 |
| I-20 | 0.15 |
| I-16 | 0.035 |
| I-17 | 1.0 |
| I-22 | 0.25 |
| I-24 | 8.0 |
| I-26 | 0.3 |
| I-23 | 0.06 |
| I-29 | 0.04 |

EXAMPLE III(B)(2)

trkA Tyrosine Kinase Activity Inhibition Assay

Fused pyrrolocarbazoles inhibited trkA tyrosine kinase activity as determined by ELISA. trkA is a high affinity receptor for neurotrophins. Fused pyrrolocarbazoles were added to 96-well microtiter plates that were previously coated with a phosphorylation substrate (phospholipase C-$\gamma$ (PLC$\gamma$)/pGEX fusion protein) (see Rotin, et al., 11 EMBO J. 559, 1992). These compounds were then tested for the ability to inhibit substrate phosphorylation by the trkA tyrosine kinase. Several of the fused pyrrolocarbazoles inhibited trkA tyrosine kinase activity with $IC_{50}$'s of approximately 20 nM (Table VII).

TABLE VII

Inhibition of trkA Tyrosine Kinase Activity

| COMPOUND | INHIBITION OF trkA KINASE $IC_{50}$ (nM) |
|---|---|
| I-2 | 20.6 |
| I-3 | 24.5 |
| I-12 | 26.7 |
| I-1 | >1,000 |
| I-7 | >1,000 |
| I-15 | >1,000 |
| 1-17 | 66.0 |
| 1-24 | >1,000 |
| I-23 | 70.6 |
| I-29 | 18.4 |
| I-32 | >1,000 |
| I-30, I-31 | >1,000 |

Methods: 96-well ELISA plates (Nunc) were coated with 1001 µl/well of the phosphorylation substrate (40 µg/ml) PLC$\gamma$/pGEX fusion protein) in 20 mM Tris, pH 7.6, 137 mM NaCl, and 0.02% NaN$_3$ overnight at 4° C. Plates were then washed three times with TBST (20 mM Tris, pH 7.6, 137 mM NaCl, 0.2% Tween-20) and subsequently blocked with 3% bovine serum albumin (BSA) in TBST for 1 hour at 37° C. Plates were washed three times with TBST, followed by two washes with TBS (TBST sans Tween-20). Fused pyrrolocarbazoles were then added at various concentrations to a reaction mixture (50 mM HEPES, pH 7.4, 5 mM MnCl$_2$, 5 mM MgCl$_2$, 140 mM NaCl, 16 µM ATP, and 15 ng trkA in a total volume of 100 µL.). As a negative control, 100 mM EDTA was included in the reaction solution. The plates were then incubated at 37° C. for 15 min. The detection antibody, monoclonal anti-phosphotyrosine antibody (UBI), was added at a dilution of 1:2000 in TBST, and incubated for 1 hour at 37° C. Plates were then washed three times with TBST, followed by a 1 hour incubation at 37° C. with alkaline phosphatase-labeled goat anti-mouse IgG (1:2000 in TBST (Bio-Rad)). After washing three times with TBST followed by two washes with TBS, a colored product was produced by using NADPH as substrate for alkaline phosphatase, and the coupled reactions of diaphorase and alcohol dehydrogenase (GIBCO-BRL ELISA amplification system). The colored product was read at 490 nm in a microplate reader (Biotek).

C. Inhibition of Induction of a Response Associated with Inflammation

The human interferons (IFNs) designated alpha (IFN$\alpha$), beta (IFN$\beta$) and gamma (IFN$\gamma$) induce their biological responses in cells from two different cell surface receptors, a first receptor for IFN$\alpha$ and IFN$\beta$ and a second receptor for IFN$\gamma$. Transcription of IFN specific genes is necessary for the subsequent IFN-induced biological responses. The IFN receptors have no known kinase activity, but the binding of the specific IFN with its receptor stimulates the phosphorylation of intracellular proteins; when these proteins are phosphorylated, they rapidly translocate to the nucleus and initiate transcription of IFN-specific genes.

Many IFN-induced biological responses, i.e., the inhibition of viral replication, inhibition of tumor growth, etc., are beneficial to the animal. However, a number of the IFN$\gamma$ biological responses are deleterious. For example, when given exogenously, IFN$\gamma$ exacerbates the symptoms of multiple sclerosis and rheumatoid arthritis; endogenous IFN$\gamma$ is also believed to play a role in exacerbating the symptoms of these diseases. Furthermore, IFN$\gamma$ is also believed to play a prominent role (causative and negative) in sepsis and general inflammation.

Indoleamine 2,3-dioxygenase (IDO) is an enzyme which initiates tryptophan degradation in the kynuerinine pathway in macrophages, monocytes and astrocytes. The tryptophan degradation pathway, as well as the interferon system, are relatively inactive in cells under normal, physiological conditions. Quinolinic acid, normally present in very low, non-deleterious amounts, is derived from the degradation of tryptophan. Quinolinic acid has been proposed to be neurotoxic by overstimulating glutamate (NMDA) receptors, resulting in the influx of $Ca^{++}$ and subsequent death of NMDA receptor-positive neurons. It has been proposed that a number of inflammatory brain diseases are caused by an excess of quinolinic acid. Under pathological situations, increased IFN$\gamma$ in response to such situations may induce IDO thereby activating the tryptophan degradation pathway, thus increasing levels of quinolinic acids, resulting in the death of neurons (see Heyes, M. P. et al. 115 *Brain* 1249, 1992). Elevated levels of quinolinic acid have been reported in a variety of inflammatory brain disorders including HIV, Lyme disease, head trauma, stroke, autoimmune diseases and sepsis (see 259 Science 25, 1993).

K-252a and staurosporine both inhibit the transcription of IFNα genes and this inhibition of transcription is not associated with the inhibition of protein kinase C. This was evidenced by prolonged treatment of cells with TPA which eliminated all detectable PKC by immunoblot analysis, but not IFNα induced transcription and the inhibition thereof by K-252a and staurosporine (see Kessler and Levy 266 IBC 23471, 1991; see also Schindler et al 257 Science 809, 1994). K-252a has also been suggested as having antiflammatory and antiallergic effects in vivo (see Ohimori, K. et al 38(1), 6 Drug Res 809, 1988).

Given the deleterious association between IDO and quinolinic acid, and the implications of quinolinic acid with a number a pathological conditions, agents which are capable of inhibiting the induction of IDO by IFNγ are useful in a research environment where the compounds which inhibit induction of IDO can be radiolabelled in order to determine their identity, isolate and purity cells to which these compounds bind and which are involved in the intimation cascade. In a therapeutic setting, the compounds which inhibit such induction can be used to inhibit, mediate, prevent and/or treat diseases and disorders such as sepsis, multiple sclerosis, rheumatoid arthritis and chronic inflammation diseases.

EXAMPLE III(C)(1)

Inhibition of Induction By IFNγ of IOD mRNA

Fused pyrrolocarbazoles in accordance with our invention were tested for a pharmacological activity consisting of their ability to inhibit the induction by IFNγ of indoleamine 2,3-dioxygenase (IDO) mRNA in THP-1 cells, a human monocyte cell line.

Cell Culture: THP-1 cells (American Type Culture Collection, Rockville, Md.), a human monocytic leukemia cell line, were grown in RPMI 1640 medium (Mediatech, Herdon Valley, Va.) with 50 μM 2-mercaptoethanol and 10% fetal bovine serum. Cells were plated in T75 culture flasks, at $4 \times 10^4$ cells/cm$^2$ in 10 ml of medium, and were immediately treated with fused pyrrolocarbazoles at various concentrations. After 30 minutes recombinant (E. coli) IFNγ (Boehringer Mannheim Corporation, Indianapolis, Ind.) was added at 200–400 units/ml. Cells were incubated (37° C., 5% CO$_2$/95% Air) for 48 hours after treatment.

RNA Isolation: Cells were pelleted by centrifugation (50×g, 7 min.) and medium was decanted. The cells were then washed two times with phosphate buffered saline pH 7.2 (PBS) (Mediatech, Herndon Valley, Va.). The cells in the washed pellet were lysed in 2 ml RNAzol B (Tel-Test, Inc., Friendswood, Tex.). RNA was isolated by chloroform extraction, precipitated, and washed following the "RNAzol B isolation of RNA" protocol accompanying this product. RNA was then solubilized in H$_2$O, and the concentration and purity were determined by reading the absorbance at A$_{260}$ nm and A$_{280}$ nm. Finally, the RNA was reprecipitated in ethanol, overnight at –20° C.

cDNA Probes: Indoleamine 2,3-dioxygenase (IDO) cDNA was received from Sohan L. Gupta, Ph.D. (Hipple Cancer Research Center, Dayton, Ohio) (see Da., W. & Gupta, S. L. 168 Biochem. Biophys. Res. Commun. 1, 1990 and Hassanain, H. H. et al. 268 J. Biol. Chem. 5077, 1993). Glyceraldehyde-3-phosphate dehydrogenase (GAPD) cDNA was obtained through American Type Culture Collection (Rockville, Md.). These cDNA's were produced and purified using standard methods (see, Sambrook, Fritsch, Maniatis (1989) Molecular Cloning a Laboratory Manual/ Second Edition 1, 1.21–1.24, 1.74–1.81, hereinafter in this Example, "Maniatis a") using Qiagen plasmid purification kits (Qiagen Inc., Chatsworth, Calif.). DNA concentration and purity were determined by absorbance at 280 nm and 260 nm. Specific DNA inserts were cut out by standard methods using restriction enzymes, and subsequently separated on agarose gels as in Maniatis (see, Sambrook, Fritsch, Maniatis (1989) Molecular Cloning a Laboratory Manual/ Second Edition 1, 6.9–6.15, hereinafter in this Example, "Maniatis b"). cDNA probes were further purified for [$^{32}$P] labeling using the Geneclean II DNA purification kit (BIO 101, Inc., La Jolla, Calif.). Probes were labeled with dCTP-α-$^{32}$P (Amersham Corp., Arlington Heights, Ill.) by random primer labeling, using the Prime-a-Gene Labeling System (Promega Corp., Madison, Wis.).

Analysis and quantification of mRNA: IDO mRNA was detected by Northern blot analysis (see Maniatis a, p. 7.39–7.51) using standard methods. After separation by electrophoresis on 1% agarose gels containing formaldehyde, the RNA was transferred to a Magnagraph nylon transfer membrane (Micron Separations Inc., Westboro, Mass.). The blots were then hybridized with [$^{32}$P]-labeled IDO cDNA (Hipple Cancer Research Center, Dayton, Ohio) according to standard methods (see Maniatis a, p. 7.52), washed and placed in phosphorimaging cassettes for 1 to 4 days. Quantification of IDO mRNA was carried out using a phosphorimager (Molecular Dynamics) in which density (i.e., amount of RNA) is expressed as relative phosphorimager units. The blots were subsequently probed for glyceraldehyde-3-phosphate dehydrogenase (GAPD) mRNA (ATCC, Rockville, Md.), an mRNA that does not change with IFNγ treatment. GAPD mRNA measurement by phosphorimager quantification of Northern blots serves as a means to normalize for potential sample to sample differences in the amount of total RNA loaded on gels. The resulting ratio of IDO mRNA/GAPD mRNA is expressed in Table VIII as a percentage of the ratio observed in IYNγ-induced cells (defined as 100%).

TABLE VIII

| Addition to cells | | |
|---|---|---|
| Compound (nM) | IFNγ (units/ml) | Phosphorimager units % of IFNγ-treated cells |
| No Compound Added | (200) | 100 |
| No Compound Added | (0) | 0.75 |
| I-29 (200 nM) | (200) | 57 |
| I-2 (400 nM) | (400) | 55 |
| I-9 (400 nM) | (400) | 60 |
| I-11 (400 nM) | (400) | 49 |
| I-32 (400 nM) | (400) | 70 |

D. Inhibition of cell growth associated with hyperproliferative states

Although nerve growth factor (NGF) is a neurotrophic protein which plays a crucial role in the development and maintenance of sensory and sympathetic neurons, there is increasing evidence that NGF, in addition to actions within the nervous system, possesses a number of biological effects on cells of the immune-inflammatory compartment. Keratinocytes, the most numerous cells in the epidermis, are thought to be crucial to cutaneous inflammatory responses (Barker, J. N. W. N. et al. 337 Lancet 211, 1991); psoriasis, a disorder characterized by keratinocyte hyperproliferation, inflammatory cell infiltration, and alteration of certain cytokines (Jablonaka, S. et al. In: Roencgk, H. H., Miaback H.(eds.) Psoriasis Dekker, Inc., New York, N.Y. 1991, pp. 261–342). NGF is also reported to activate most cells and T-lymphocytes, which invade the psoriatic lesion; interleukin-6, also expressed in high levels in psoriatic skin and which also stimulates proliferation of human keratinocytes, can enhance NGF secretion (see Grossman, RM et al. 86 PNAS 6367, 1989 and Frei, K. et al. 19 Eur. J. Immunol. 689, 1989). Recently, it was reported that NGF stimulates the proliferation of human keratinocytes in culture, and that K-252a prevents such proliferation (see Pincelli, C. et al., 103(1) J. Invest. Derma. 13, 1994).

In therapeutic settings, the fused pyrrolocarbazoles can be advantageously utilized to inhibit the hyperproliferation of keratinocytes, thus acting to inhibit, mediate, reverse and/or prevent the occurrence of a psoriatic condition. Use of our fused pyrrolocarbazoles can be beneficially exploited in the arena of psoriatic conditions, given the ability of K-252a to inhibit the proliferation of human keratinocytes and the link between the hyperproliferation of keratinocytes and psoriasis; the fused pyrrolocarbazoles can be utilized to further enhance the understanding of inhibition of keratinocytes and the cellular relationship between, e.g., NGF, keratinocytes and disorders exemplified by psoriasis.

Cancers, almost universally by definition, involve hyperproliferative growth of cells to a malignant state, typically resulting in the formation of tumors. Thus, we have investigated the ability of our compounds to effect the growth of prostate cancer cells as an exemplary approach to defining compounds which inhibit the growth of cells associated with a hyperproliferative state. Accordingly, our compounds can also be utilized in this context for both research and therapeutic avenues: in a research environment, the compounds can be used to, e.g., screen for other compounds that can also inhibit the growth of cells associated with hyperproliferative states; in a therapeutic arena, the compounds which beneficially inhibit the growth of specific cells associated with specific diseases and/or disorders can be advantageously exploited in the mediation, treatment and/or prevention of such diseases or disorders.

EXAMPLE III(D)(1)

Inhibition of Growth of Prostate Cancer Cell Line Using Fused Pyrrolocarbazoles

AT-2 cells are a prostate cancer cell sub-line derived from the Dunning H tumor, graciously provided to us by Dr. John Isaacs (John Hopkins, M.D.). Unlike the Dunning H tumor cells, AT-2 cells can be grown in vitro.

Methods: AT-2 cells ($7.5 \times 10^4$ cells/well) were plated on tissue culture plastic in 96-well plates in the presence of RPMI-1640 medium containing 10% fetal calf serum, 250 nM dexamethasone, 2 mM glutamine, 1 mM sodium pyruvate, and penicillin/streptomycin antibiotics. The next day, compounds were added at 4 concentrations (10, 1, 0.1, 0.01 µM) to determine the approximate $IC_{50}$ range. Cultures were assayed 3 days later for cell number using the MTS [(3-(4,5-dimethylthiazol-2-yl)-5-(3-carboxymethoxyphenyl)-2-(4-sulfophenyl)-2H-tetrazolium, inner salt)]assay. The MTS assay (purchased as a kit from Promega) measures the formation of an aqueous soluble formazan (detected by a plate reader at 490nm) produced by the bioreduction of a tetrazolium compound (MTS) in metabolically active cells via mitochondrial succinate dehydrogenase. After determining linearity of the substrate incubation time over a range of cell plating densities, the amount of product measured is directly proportional to cell number. MTS (333 µg/ml) and 25 µM phenazine methosulfate are mixed and added directly to the culture medium, and incubated at 37° C. in the 5% $CO_2$/95% air incubator for 0.5–4 h. Absorbance of the product at 490 nm is read on the BIO-TEK plate reader. Background values were obtained from wells containing culture medium with substrate solution, but no cells. In addition, values were also obtained from wells containing cells plated at day 0 and assayed on the day compound was added (day 1) in order to determine the number of cells at the time compound was added. After the initial dose-finding experiment was completed, subsequent experiments were set up so that there were 3 or more concentrations near the predicted $IC_{50}$.

TABLE IX

| Compound # | AT-2 cell growth $IC_{50}$ (nM) |
| --- | --- |
| I-3 | 380 |
| I-7 | 1370 |
| I-29 | 3260 |
| I-2 | 4600 |
| I-24 | >10,000 |
| I-14 | 3070 |
| I-15 | 4300 |
| I-20 | >10,000 |
| I-21 | >10,000 |

E. Inhibition of Developmentally Programmed Motoneuron Death

In the chick, somatic motoneurons undergo naturally occurring death between embryonic days 6 and 10 (E6 and E10). (See Chu-Wang, L. W. & Oppenheim, R. W. 177 J. Comp. Neurol. 33,1978; and Hamburger, V 160 J. Comp. Neurol. 535, 1975). During this period, the number of motoneurons on the two sides of the lumbar spinal cord of developing chick embryos decreases by about 50%, from about 46,000 to about 23,000.

As to the data below reveals, fused pyrrolocarbazoles as disclosed herein inhibited the naturally occurring death of these neurons; such inhibition occurred in a dose-dependent manner.

EXAMPLE III(E)(1):

Inhibition of Motoneuron Death In Ovo Using Fused Pyrorolocarbazoles

Chick embryos (E6–E9) were treated with either vehicle (5% Solutol HS 15, BASF Aktiengesellschaft) or concentrations of I-34 or I-32 as described. The samples (50 ul) were applied to the vascularized chorioallantoic membrane through a window in the egg shell as previously described (Oppenheim et al., 1988). Embryos were sacrificed on E10 and spinal cords were removed, fixed in Carnoy's solution (10% acetic acid, 60% ethanol, 30% chloroform), embedded in paraffin, sectioned at 8 um, and stained with thionin as described previously (Oppenheim et al., 1988). Motoneurons (identified by morphology and position) were counted by an individual blind to the treatment conditions in every tenth section according to previously established criteria (Oppenheim et al., 1982, Oppenheim, 1986).

Daily application of I-34 or I-32 to the chorioallantoic membrane of E6 to E9 chicks in ovo resulted in a dose-dependent increase in the number of surviving lumbar motoneurons (Table X). For compounds I-34 and I-32, the maximal effect was achieved at a dose of 0.6 ug/egg, resulting in a 27% and 31% increase, respectively, in motoneuron survival in treated vs. control, vehicle-treated embryos.

TABLE X

| Treatment | Daily Dose (ug/egg) | Number of motoneurons mean ± SD | % increase of motoneurons rescued versus control |
|---|---|---|---|
| Control Vehicle | 0 | 9440 ± 453 | |
| I-34 | 0.6 | 11976 ± 1106** | 27 |
| | 0.3 | 11593 ± 654** | 23 |
| | 0.15 | 10135 ± 354* | 7 |
| | 0.015 | 10480 ± 585* | 11 |
| I-32 | 1.2 | 11743 ± 1497** | 24 |
| | 0.6 | 12357 ± 499** | 31 |
| | 0.3 | 10215 ± 481* | 8 |
| | 0.06 | 9657 ± 529 | not significant |

Number of motoneurons represents counts made on one side of the spinal cord.
Student t test: **$p < 0.01$; *$p < 0.05$ versus control, vehicle-treated embryos IV. Synthetic Processes for Production of Fused Pyrrolocarbazoles The invention features a method for preparing a D-ring-fused pyrrolocarbazole, the method comprising the steps of:

a) obtaining an indole represented by general formula IV, wherein $R^2$ is H, $SO_2R^9$, $CO_2R^9$, or alkyl of 1–4 carbons, and each $R^{3a}$ and $R^{4a}$ is H, F, Cl, Br, I, —$OR^9$, —$O(CH_2)_nNR^7R^8$, $NR^7R^8$, —$SR^{11}$, alkyl, aryl, heteroaryl, —$(CH_2)_nSR^{11}$, —$(CH_2)_nOR^9$, or —$(CH_2)_nNR^7R^8$;

b) reacting said indole with a 2-indanone represented by the following general Formula:

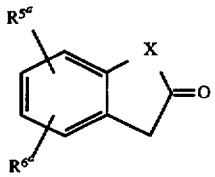

wherein each $R^{5a}$ and $R^{6a}$ is H, F, Cl, Br, I, alkyl, aryl, heteroaryl, CN, $NO_2$, $OR^9$, —$O(CH_2)_nNR^7R^8$, $CO_2R^9$, $SO_2R^9$, $SR^{11}$, —$(CH_2)_nS(O)_xR^9$, —$(CH_2)_nSR^{11}$, $NR^7R^8$, or —$(CH_2)_{nN}R^7R^8$, and X is an alkylene group of 1–3 carbons (inclusive) or —$C(R^{10})_2$—, under conditions capable of forming a 2-(2-cycloalkenyl)indolo tertiary alcohol (Formula V) and eliminating the hydroxyl group of said alcohol to form the corresponding 2-(2-cycloalkenyl)indole (Formula VI);

c) reacting said 2-(2-cycloalkenyl)indole with an imide represented by the following general Formula:

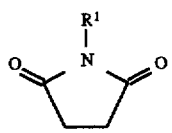

wherein $R^1$ is defined above, under conditions which form a tetrahydropyrrolocarbazole represented by general Formula VII; and d) dehydrogenating the tetrahydrocarbazole ring of said tetrahydropyrrolocarbazole under conditions which form a fused pyrrolocarbazole of general Formula VIII.

The invention features a method for making substantially pure regiospecific D-ring-fused pyrrolocarbazole lactam isomers, said method comprising the steps of:

a) obtaining a fused pyrrolocarbazole represented by general formula VIII, wherein $R^1$, $R^2$, $R^{3a}$, $R^{4a}$, $R^{5a}$, $R^{6a}$ and X are as previously defined;

b) reducing the imide group of said fused pyrrolocarbazole under conditions which form two fused pyrrolocarbazole lactam isomers represented by general Formulae IX and X;

and c) separating said isomers under conditions which produce substantially pure regiospecific D-ring-fused pyrrolocarbazole lactam isomers.

The invention features a method of making a regiospecific D-ring fused pyrrolocarbazole lactam isomer, said method comprising the steps of:

a) obtaining a compound of the general Formula XI, wherein $R^2$, $R^{3a}$, $R^{4a}$, $R^{5a}$, $R^{6a}$ are as previously defined, and X is S, O, CO, alkylene of 1–3 carbons, —$C(R^{10})_2$, —$CH_2Z$—, —$ZCH_2$—, or —$CH_2ZCH_2$—;

b) reacting said compound with a lower alkyl β-cyanoacrylate, preferably ethyl β-cyanoacrylate, under conditions which form tetrahydrocarbazole cyano-ester isomers represented by general Formulae XII and XV, wherein R is a lower alkyl group;

c) separating said isomers under conditions which produce substantially pure regiospecific tetrahydrocarbazole cyano-ester isomers;

d) separately dehydrogenating the tetrahydrocarbazole ring of each of said isomers sufficient to form the corresponding carbazole cyano-esters (Formulae XIII and XVI); and e) separately reacting each of said carbazole cyano-esters under reductive conditions which independently produce regiospecific fused pyrrolocarbazoles represented by general formulae XIV and XVII.

The invention features a method of making a D-ring-fused pyrrolocarbazole, said method comprising the steps of:

a) obtaining an indole represented by general formula IV, wherein $R^2$, $R^{3a}$ and $R^{4a}$ are as previously defined;

b) reacting said indole with a 2-benzocycloalkanone represented by the following general formula:

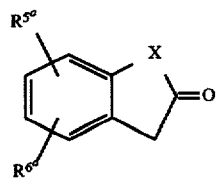

wherein $R^{5a}$ and $R^{6a}$ are as previously defined and X is an alkylene group of 2–3 carbons (inclusive); said reacting being under conditions which form a 2-(2-(1,2,3,4,-tetrahydroarylalkyl)) indolyl tertiary alcohol; and eliminating the hydroxyl group of said alcohol to form the corresponding 2-(2-cycloalkenyl)indole;

c) reacting said 2-(2-cycloalkenyl)indole with an imide represented by the following general Formula:

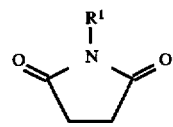

where $R^1$ is as defined above; said reacting being under conditions which form a tetrahydroarylalkylpyrrolocarbazole represented by the general Formula XVIII; and either

29 i) dehydrogenating the D-ring of said pyrrolocarbazole under conditions which produce the corresponding fused pyrrolocarbazole represented by general Formula XIX;

or ii) dehydrogenating the E-ring of said pyrrolocarbazole under conditions which produce the corresponding fused pyrrolocarbazole represented by general Formula XX.

The invention features a method of making a D-ring-fused pyrrolocarbazole, said method comprising the steps of:

a) obtaining a lower alkyl stannylindole represented by general formula XXI, wherein $R^2$ is $-CO_2H$, $-SO_2R^9$, $-CO_2R^9$ or alkyl; $R^{3a}$ and $R^4$ are as defined above;

b) coupling said lower alkyl stannylindole with a compound represented by the following general Formula:

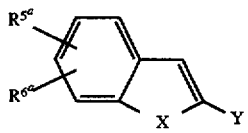

wherein $R^{5a}$ and $R^{6a}$ are as defined above; X is S, O, CO, alkylene of 1-3 carbons, $-C(R^{10})_2-$, $-CH_2Z-$, $-ZCH_2-$ and $CH_2ZCH_2-$; and Y is Br, I or $-OSO_2CF_3$, said coupling being under conditions which form an indole of general formula XXII;

c) separately reacting said indole with either:

i) an imide represented by the following general formula:

or ii) a lower alkyl β-cyanoacrylate;

each under conditions which independently form the corresponding indolo-imide represented by general Formula XXIII;

and d) cyclizing said indoloimide under conditions which form a fused pyrrolocarbazole represented by the following general Formula XXIV.

The following apply herein:

Lower alkyl is 1-4 carbon atoms.

Aryl is $C_6$-$C_{10}$, preferably phenyl or naphthyl.

Alkyl β-cyanoacrylate is 1-8 carbon atoms in the alkyl group.

Arylalkyl is 7-14 carbon atoms.

Heteroaryl is a group of 3-10 atoms selected from C, O, S and N, with at least one atom being O, S or N.

Heteroarylalkyl is a heteroaryl group attached to an alkyl of 1-8 carbon atoms.

Alkylene is 2-8 carbon atoms.

Monosaccharide is a 3, 4, 5, 6 or 7-carbon sugar such as glucose, ribose, or rhamnose.

Alkylcarbonyloxy contains an alkyl group of 1-8 carbons.

V. General Description of Synthetic Processes

Compounds of the invention are prepared by the general processes described below.

30

Figure 2:
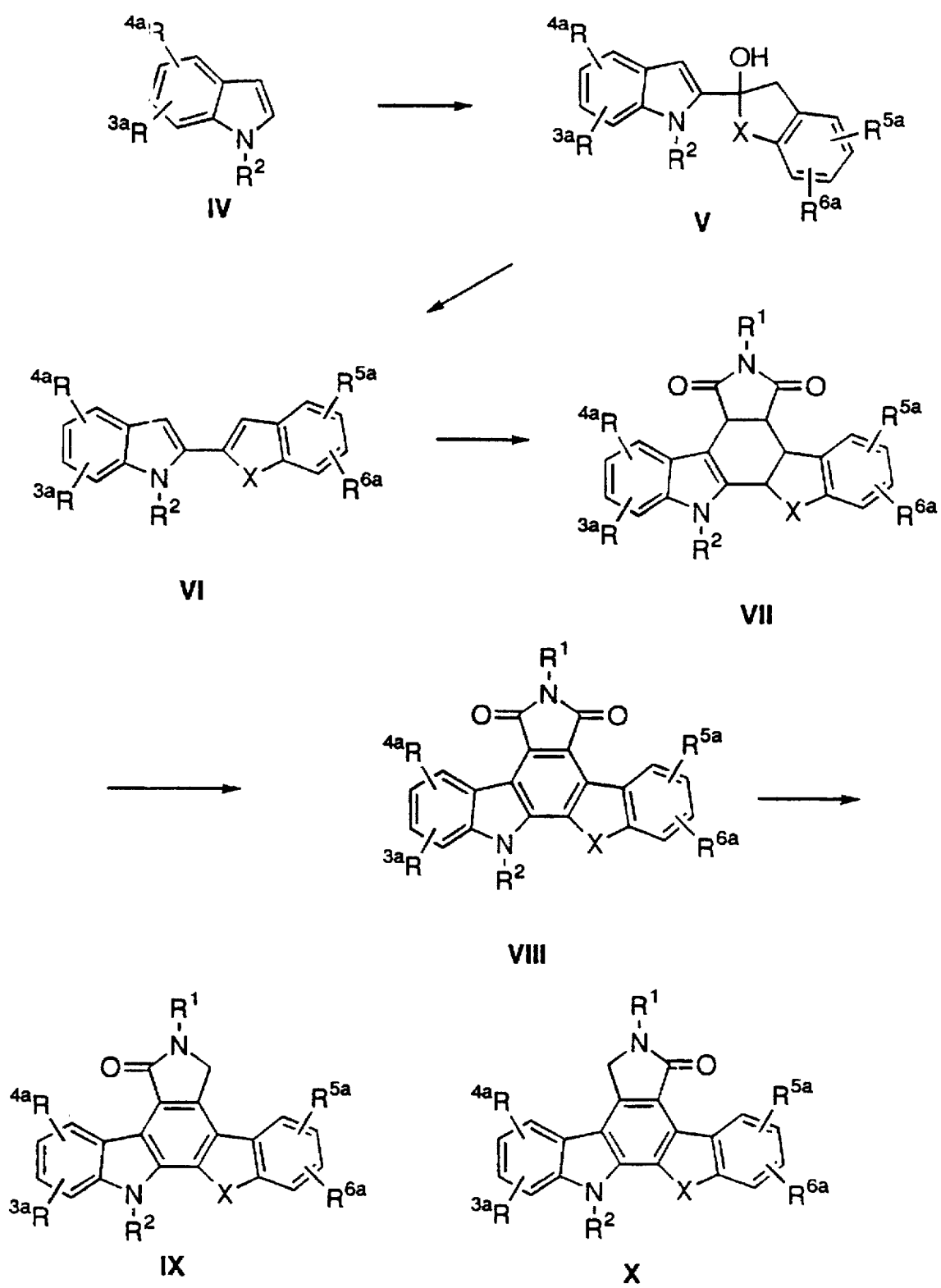
FIG. 2 is a schematic drawing outlining the chemical synthesis of isomeric fused pyrrolocarbazoles (IX and X) from an indole (IV).
Figure 3:
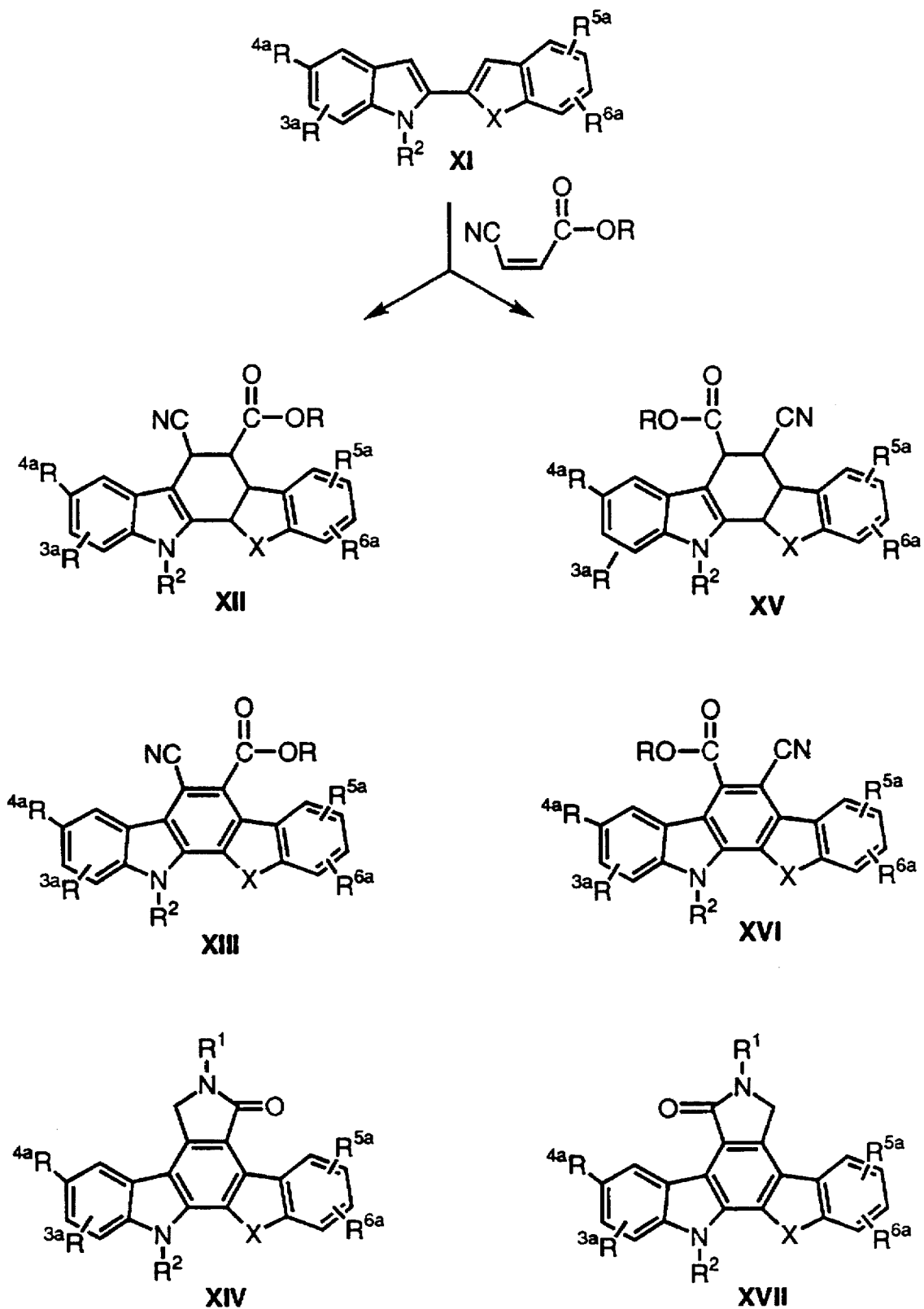
FIG. 3 is a schematic drawing outlining the chemical synthesis of isomeric fused pyrrolocarbazoles (XIV and XVII) from a 2-(2-indenyl) indole (XI).

Two general synthetic routes were employed to prepare the fused pyrrolocarbazoles of the invention (FIGS. 2 and 3). Method A (FIG. 2) uses an indole derivative (IV) which is either unsubstituted or substituted at carbons 4-7 (inclusive). The indole derivatives are prepared using standard methodology (U.S. Pat. No. 3,976,639; U.S. Pat. No. 3,732,245; *The Chemistry of Heterocyclic Compounds, Indoles Parts One and Two*; Houlihan Ed., Wiley-Interscience (1972)). In Method A (FIG. 2), 1H-indole or a derivative thereof is protected as a lithium indole-1-carboxylate intermediate (*Tetrahedron Lett.* 26:5935 (1985)), then treated with a strong base, such as t-BuLi, then alkylated with an appropriate 2-indanone derivative to give the corresponding tertiary alcohol V. The 2-indanone derivatives can be prepared using previously described procedures (see U.S. Pat. No. 4,192,888; U.S. Pat. No. 4,128,666; *J. Am. Chem. Soc.* 89:4524 (1967); *Tetrahedron Lett.* 43:3789 (1974); *Chem. Ber.* 122:1791 (1989); *Can. J. Chem.* 60:2678 (1982); *Helvetica Chimica Acta* 70:1791 (1987); *Chem. Pharm. Bull.* 33:3336 (1985); *J. Org. Chem.* 55:4835 (1990); *Tetrahedron* 45:1441 (1989); *Synthesis* 818 (1981)). The resulting tertiary alcohol V is treated with a dilute acid (e.g., 2N HCl in acetone) to give the corresponding 2-(2-indenyl)indole VI. Alternatively, the starting 1H-indole derivative described previously is converted to a 1-substituted indole derivative (IV; $R^2$ not=H) by standard methodology, for example, by treatment of the 1H-indole with base and an alkylating agent to give a 1-substituted indole. In these examples, the indole derivative can be directly treated with a strong base (e.g., t-BuLi, sec-BuLi, n-BuLi, lithium diisopropylamide) followed by alkylation with a 2-indanone derivative to give the corresponding tertiary alcohol V, which includes substituents in position one of the indole ring. Cycloaddition reaction of compounds of the general formula VI with maleimide, preferably at temperatures of 160°-200° C., forms the corresponding tetrahydrocarbazole VII. Cycloaddition reactions of 2-(2-indenyl)indoles have not been described previously. Cycloaddition reactions of 2-vinyl indoles with maleimides are well known (U.S. Pat. No. 4,912,107 and references therein). Compound VII is dehydrogenated according to conventional processes with, for example, 2,3-dichloro-5,6-dicyano-1,4-benzoquinone, Pd on active charcoal, sulfur or sodium nitrite (U.S. Pat. No. 4,912,107 and references cited therein) to give the corresponding aromatized pyrrolocarbazole derivative VIII. Isomeric lactams of general formula IX and X can be prepared by the reduction of imide VIII with reducing agents (e.g., zinc amalgam, gaseous hydrogen chloride, zinc amalgam in acetic acid, zinc in glacial acetic acid, or hydride reducing agents such as lithium aluminium hydride). Regioisomers are separated by standard processes such as recrystallization or chromatography, for example, column chromatography or HPLC. The imides are reduced to hydroxylactams where $A^1$, $A^2$ or $B^1$, $B^2$=H,OH by hydride reducing agents such as borohydrides or aluminium hydrides (U.S. Pat. Nos. 4,192, 107 and 4,923,986 and references therein). The resulting hydroxyl group is easily converted to alkoxy or thioalkyl groups (U.S. Pat. No. 4,923,986). Derivatives in which $A^1$, $A^2$ or B1, $B^2$ together represent S or N are prepared as described in European Patent Application No. 0 508 792 AI.

Method B (FIG. 3) outlines a novel method for the preparation of isomeric fused pyrrolocarbazole lactams (XIV, XVII). Cycloaddition reaction of a compound of general formula XI with ethyl β-cyanoacrylate at temperatures of 160°-200° C., yields isomeric tetrahydrocarbazole cyano-esters (XII and XV). Isomers XII and XV are separated into regiospecific isomers by recrystallization or chromatography, e.g., column chromatography or HPLC.

XII and XV can be separately dehydrogenated according to conventional methods, for example, with 2,3-dichloro-5,6-dicyano-1,4-benzoquinone, Pd on active charcoal, sulfur or sodium nitrite (U.S. Pat. No. 4,912,107 and references cited therein), to give the corresponding aromatized pyrrolocarbazole derivative (XIII or XVI). Regiospecific lactams of the general structures XIV and XVII (FIG. 3) can be separately prepared by reductive-cyclization of the corresponding nitrile-esters XIII or XVI by using reducing agents, for example, Raney Nickel/$H_2$, PdO, or Pd on activated charcoal.

Figure 4:
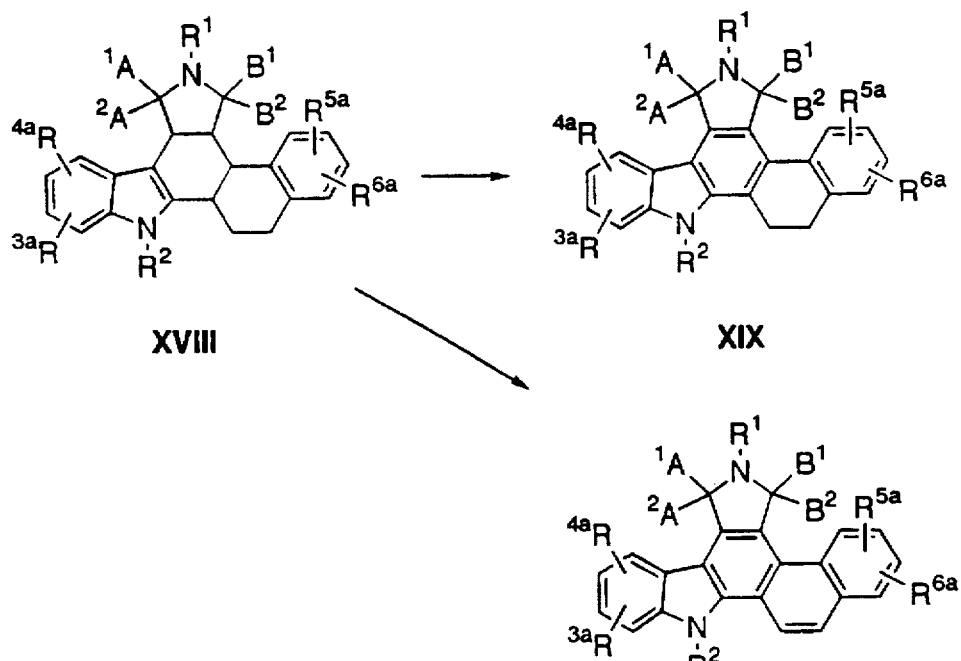
FIG. 4 is a schematic drawing outlining the dehydrogenation of a hexahydrocarbazole (XVIII) to form the corresponding partially (XIX) or more fully (XX) dehydrogenated fused pyrrolocarbazole.

Fused pyrrolocarbazole derivatives of Formula I in which $X=CH_2CH_2$, XIX, or CH=CH, XX are prepared by the procedures described for Methods A and B (FIGS. 2 and 3), except the 2-indanone compound was replaced with a 2-tetralone. The 2-tetralone compound can be prepared by using standard procedures (*J. Med Chem.* 32:2128 (1989); *J. Med Chem.* 36:2279 (1993); *J. Med. Chem.* 36:2485 (1993); *Tetrahedron Lett.* 14:951 (1971); *J. Org. Chem.* 33:4288 (1968); *J. Org. Chem.* 26:4232 (1961); *J. Med. Chem.* 25:1358 (1982); *Synth. Commun.* 21:981 (1991); WO 92/06967, WO 92/16524, and WO 90/15047). FIG. 4 shows a fused pyrrolocarbazole derivative in which X is $CH_2CH_2$ (XVIII). Partial dehydrogenation of XVIII with 2,3-dichloro-5,6-dicyano-1,4-benzoquinone in toluene at 65° C. gives the corresponding dihydronaphthyl derivative XIX. Treatment of XVIII with 2,3-dichloro-5,6-dicyano-1,4-benzoquinone in dioxane at reflux temperatures gives the corresponding fully dehydrogenated naphthyl derivative XX. Replacement of the 2-indanone compound with a 2-benzosuberone derivative (*J. Am. Chem. Soc.* 13:1344, (1991); *J. Org. Chem.* 44:1342 (1979)) gives fused pyrrolocarbazoles of general structure I, where $X=CH_2CH_2CH_2$. Ketone derivatives where X is C=O can be prepared by oxidation of either the imide or lactam of I by using standard oxidizing reagents (e.g., $SeO_2$, $CrO_3$, $Na_2CrO_7$, or $MnO_2$).

Figure 5:
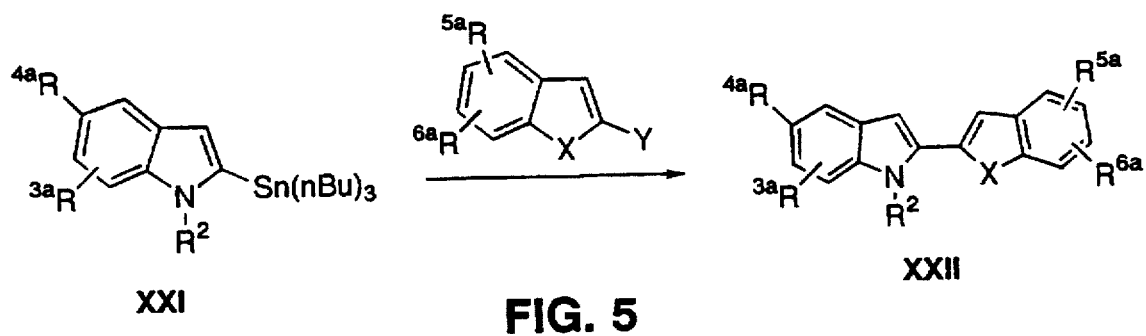
FIG. 5 is a schematic drawing outlining the chemical synthesis of a 2-(2-indenyl)indole derivative (XXII) from a 1-carboxy-2-tributylstannylindole (XXI).
Figure 6:
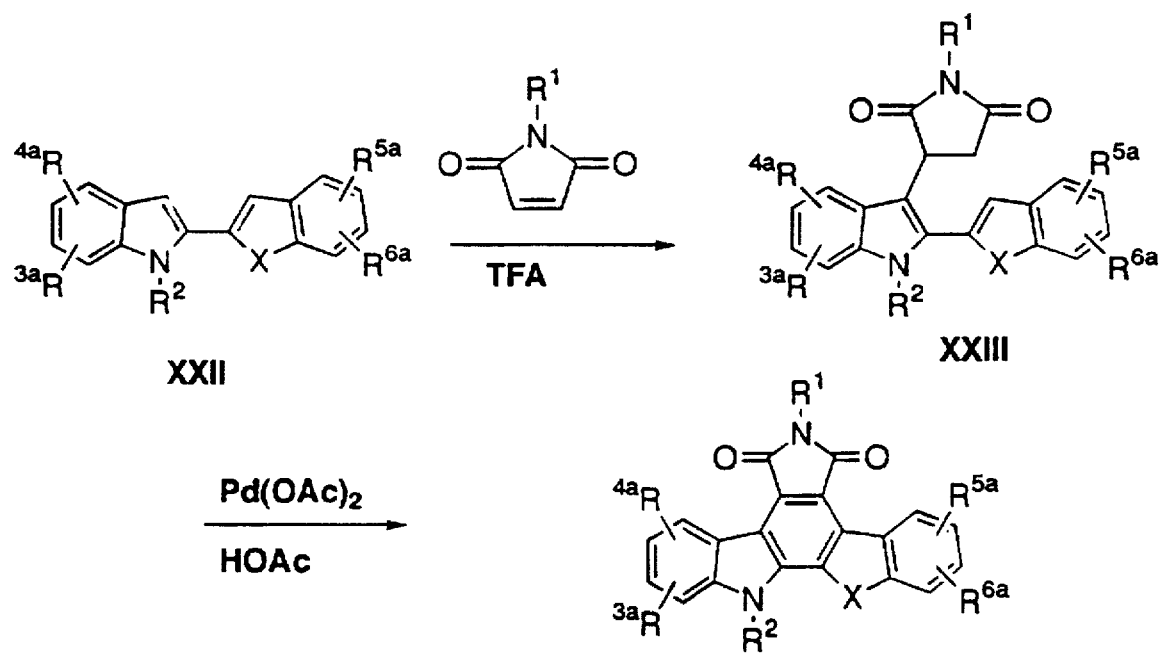
FIG. 6 is a schematic drawing outlining the chemical synthesis of an indoloindenylimide (XXIII) from a 2-(2-indenyl)indole (XXII). The indoloindenylimide (XXIII) is cyclized under reducing conditions to form the corresponding fused pyrrolocarbazole (XXIV).
Figure 7:
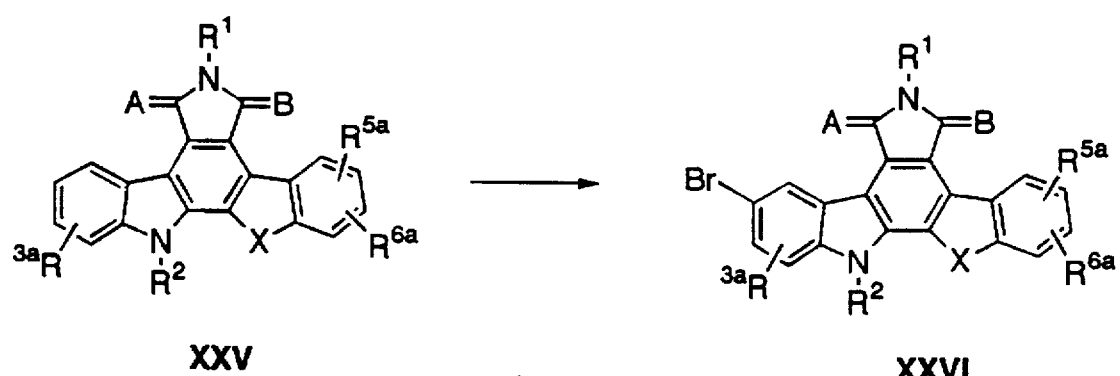
FIG. 7 is a schematic drawing showing the chemical synthesis of a brominated fused pyrrolocarbazole (XXVI) from a fused pyrrolocarbazole (XXV).

Compounds in which X=S, O, or C=O (general structure XXII) can be prepared by cycloaddition reactions as described in Methods A and B (FIGS. 2 and 3). For example, the compounds 2-(2-(1-oxoindenyl)indole, 2-(2-benzothienyl)indole, 2-(2-indenyl)indole, and 2-(2-benzofuranyl)indole may each be prepared by coupling 1-carboxy-2-tributylstannylindole (XXI) with 2-bromobenzothiophene, 2-bromobenzofuran, or 1-oxo-2-(trifluoromethanesulfonate)indene (FIG. 5) by using standard published procedures (*Angew. Chem. Int. Ed. Engl.* 25:508 (1986); *J. Am. Chem. Soc.* 109:5478 (1987); *Tetrahedron Lett.* 37:4407 (1986)). Preparation of a carbazole is also achieved by treatment of 2-(2-benzothienyl)indole or 2-(2-benzofuranyl)indole (XVII, where X=S or O, respectively) with maleimide or ethyl 13-cyanoacrylate in the presence of an acidic catalyst such as trifluoroacetic acid which gives a compound of general formula XXIII (FIG. 6). These compounds can be cyclized to form the corresponding fused pyrrolocarbazole (general structure XXIV) by treatment with a catalyst, for example, Pd(OAc)$_2$ in glacial acetic acid.

The palladium-catalyzed cross-coupling methodology is used to prepare other derivatives, for example, where X in FIG. 6 has 1–3 carbons (inclusive), by coupling the 2-(trifluoromethanesulfonate) derivative of the corresponding cyclic ketone with 1-carboxy-2-tributylstannylindole.

Lactam isomers of general formulae XIV and XVII, in which $R^2$ is hydrogen, can be alkylated in the presence of base (e.g., hydrides, alkoxides, hydroxides of alkali or alkaline earth metals, or of organo-lithium compounds) by treatment with $R^2L$ in which L is a leaving group such as a halogen. The resulting fused pyrrolocarbazole has an alkyl group bound to the indole nitrogen (AU-A-29607 and U.S. Pat. No. 4,912,107). A sugar group can be added to the indole nitrogen as described (European Patent Application No. 0 602 597 A2).

Imides of the general formula XX in which the imide nitrogen is bound by hydrogen can be converted to an $R^1$ group as described for I (U.S. Pat. No. 4,923,986). Lactam isomers with derivatives other than $R^1$=H are prepared by processes described in Method A.

Imides of general formula I in which $R^3$, $R^4$, $R^5$, or $R^6$ substituents are other than H are prepared by the procedures described (U.S. Pat. No. 4,923,986) or by using standard methods known to those skilled in the art of organic chemistry.

Fused pyrrolocarbazoles of the general formula G in which rings B and F may independently contain nitrogen, oxygen, or sulfur ring atoms, as defined above for $E^1$ and $E^2$, may be prepared by similar processes used to prepare the carbocyclic analogs described in general formulae 1a and 1b.

Figure 8:
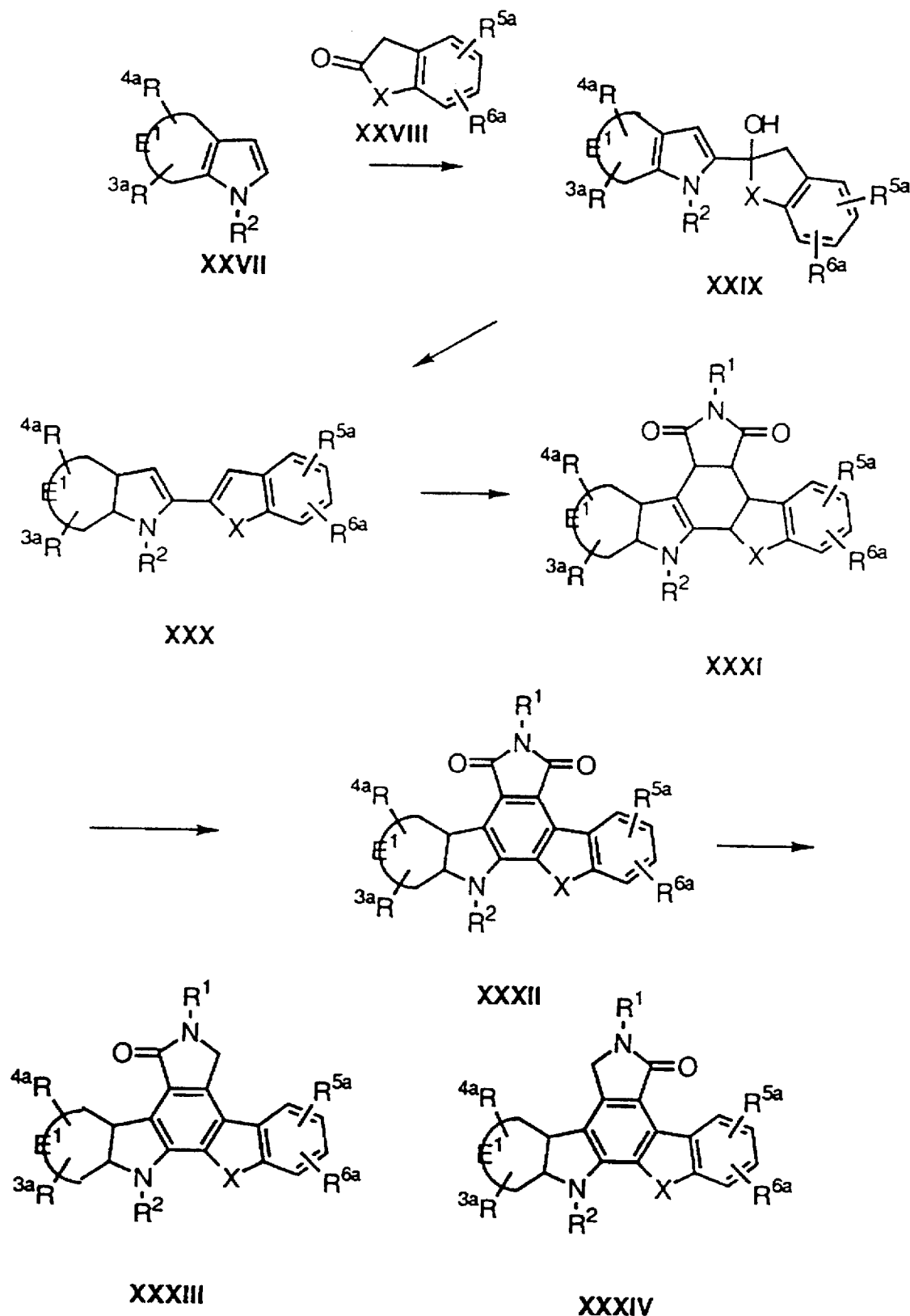
FIG. 8 is a schematic drawing outlining the chemical synthesis of selected isomeric fused pyrrolocarbazoles (XXXIII and XXXIV) from an indole (XXVII).

Preparation of derivatives in which ring B is a 6-membered nitrogen containing heterocyclic ring are outlined in FIG. 8. A 1H-azaindole (XXVII: N in the 4, 5, 6, or 7-positions of the indole phenyl portion, used instead of a 1H-indole; R=H, $R^{3a}$, $R^{4a}$ as previously described) substituted or unsubstituted, is protected as a lithio-1-carboxylate, followed by treatment with a strong base such as t-butyl lithium, then alkylated with a cyclic ketone derivative (for example 2-indanone or 2-tetralone) to give the tertiary alcohol XXIX ($R^{5a}$, $R^{6a}$ and X as previously described). The 1H-azaindole derivatives may be prepared using previously described literature procedures (see *J. Org. Chem.* 57:6995 (1992); *Bioorg. Med. Chem. Lett.* 2:1053 (1992); *Heterocycles* 34:2347 (1992); *J. Hetero. Chem.* 29:359 (1992); *Khim. Geterotsikl. Soedin.* 1:86 (1979); *Khim. Geterotsikl. Soedin.* 8:1135 (1978); *J. Hetero. Chem.* 6:775 (1969); *Tetrahedron* 49:2885 (1993); *Chem. Pharm. Bull.* 35:1823 (1987); *Khim. Geterotsikl. Soedin.* 3:375 (1979); *J. Hetero. Chem.* 15:325 (1978); *Khim. Geterotsikl. Soedin.* 1:27 (1970); *J. Organomet. Chem.* 445:273 (1993); *Heterocycles* 34:2379 (1992); *J. Chem. Soc. C* 11:1505 (1969); published patent specifications WO 94/20497; and WO 94/20459). The resulting tertiary alcohol XXIX may be treated with a dilute acid, for example, 2N HCl in acetone, to give the dehydrated product XXX. The starting 1H-azaindole derivatives (XXVIII previously described may be converted to a 1-substituted azaindole derivative ($R^2$ not H) by standard methodology, for example, by treatment of the 1H-azaindole with base and an alkylating agent to give a 1-substituted product. In these examples the azaindole derivative can be treated directly with a strong base followed by alkylation with a cyclic ketone derivative to give the corresponding tertiary alcohol XXIX, which includes substituents in position 1 of the azaindole ring. Cycloaddition reactions of the compound of general formula XXX with maleimide (FIG. 8) would give compounds of the general formula XXXI. Dehydrogenation of intermediate XXXI in a manner similar to preparation of VIII (FIG. 2) would give imide derivatives of the general formula XXXII (FIG. 8). Lactam isomers of the general formulae XXXIII and XXXIV may be prepared by the reaction of imide derivatives of the general formula XXXII with reducing agents such as zinc amalgam-HCl, zinc amalgam in acetic acid, or hydride reducing agents such as lithium aluminum hydride. Regioisomers can be separated by standard processes such as recrystallization or chromatography, for example, column chromatography or HPLC. The imides are reduced to hydroxylactams where $A^1$, $A^2$ or $B^2$, $B^2$=H, OH, by hydride reducing agents such as borohydrides or aluminum hydrides.

Method B (FIG. 9) outlines an alternative method for the direct preparation of regioisomeric lactam isomers XXXIII and XXXIV. Cycloaddition reaction of a compound of general formula XXX with ethyl b-cyanoacrylate would give tetrahydrocarbazole isomers XXXV and XXXVI. Regioisomers can be separated by standard processes such as recrystallization or chromatography, for example, column chromatography or HPLC. Isomers can be separated at this step or at a later step in the process. Isomers XXXV and XXXVI can be dehydrogenated acco to conventional methods, for example with 2,3-dichloro-5,6-dicyano-1,4-benzoquinone (DDQ), to give the corresponding aromatized pyrrolocarbazole derivatives of the general formulas XXX-VII and XXXVIII. Lactam isomers of the general formulas XXXIII and XXXIV can be prepared by reductive cyclization of the nitrile-esters XXXVII and XXXVIII with reducing agents, e.g., Raney Nickel, PdO, or Pd on activated carbon under a hydrogen atmosphere.

Figure 9:
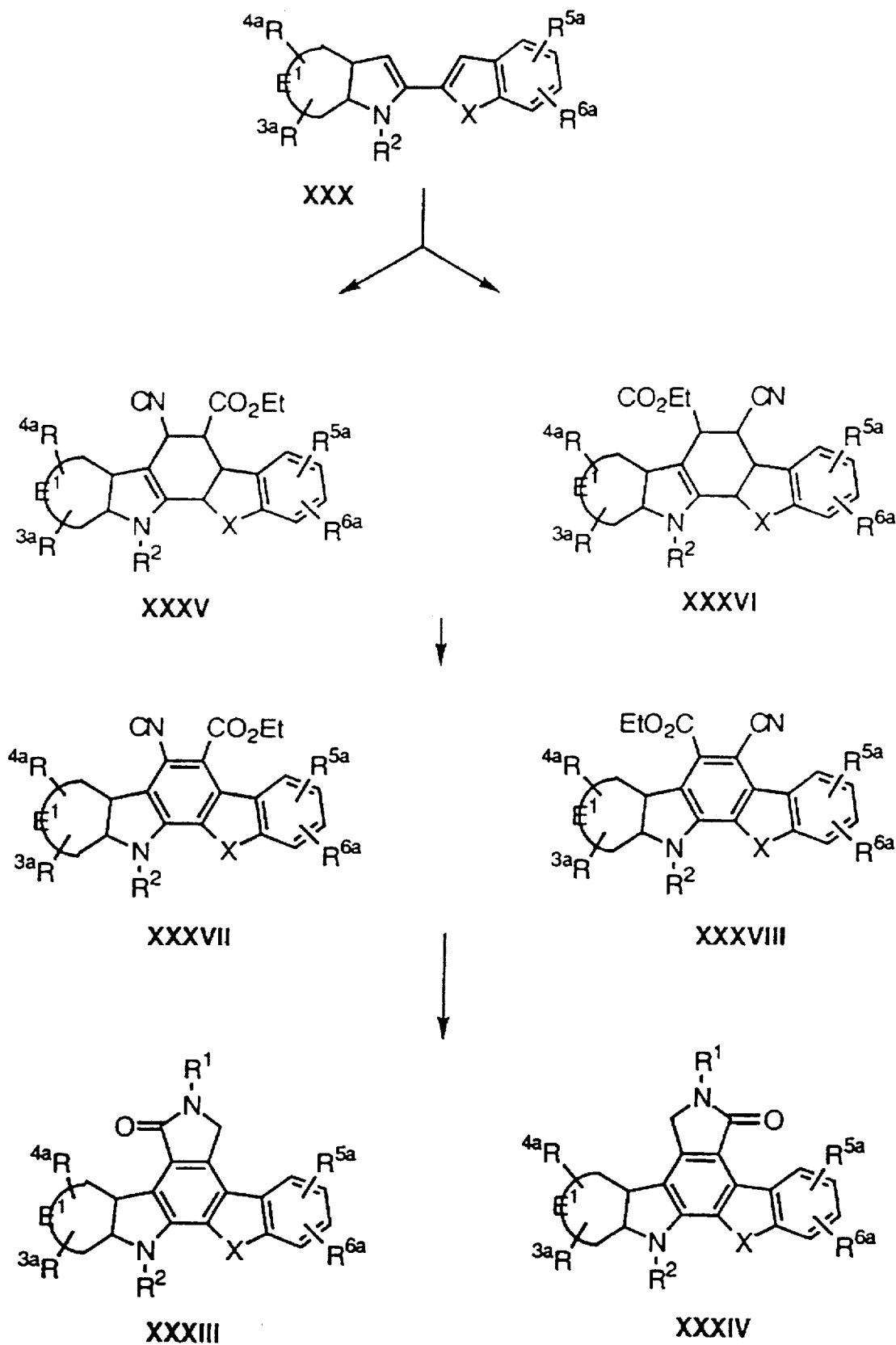
FIG. 9 is a schematic drawing outlining the chemical synthesis of selected isomeric fused pyrrolocarbazoles (XXXIII and XXXIV) from an indole (XXX).

Compounds in which ring B is a 5-membered ring containing oxygen or sulfur may be prepared starting with furyl-pyrroles or thieno-pyrroles, respectively, in place of indoles following the synthetic schemes outlined in FIGS. 8 and 9. Ring fused furyl-pyrroles may be prepared using previously established literature procedures or modifications thereof (Coll. Czech. Chem. Commun. 53:1770 (1988); Can. J. Chem. 56:1429 (1978); C. R. Hebd. Seances Acad. Sci., Ser. C 281:793 (1975)). Ring fused thienyl-pyrroles may be prepared using previously established literature procedures or modifications thereof (Belgian patent specification BE 899925; Ind. J. Chem. 20B:271 (1981); Can J. Chem. 56:1429 (1978); Bull. Soc. Chem. Fr. 11–12 pt2:2511 (1975); C. R. Hebd. Seances Acad. Sci., Ser. C 277:1149 (1973)).

Figure 10:
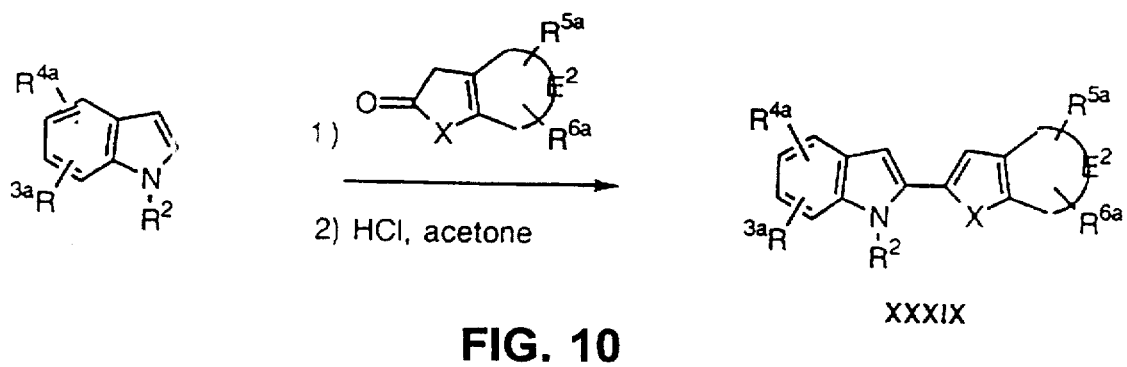
FIG. 10 is a schematic drawing outlining the chemical synthesis of intermediates to fused pyrrolocarbazoles in which ring F contains a ring nitrogen atom.

Alternatively, compounds in which ring F contains nitrogen ting atoms may be prepared starting with cycloalkanone-fused-pyridine derivatives ($X=C_1-C_3$ alkylene). The syntheses of cycloalkanone-pyridine derivatives have been described in the literature (J. Med. Chem. 36:3381 (1993)), and these compounds may be used directly to prepare intermediates of the general structure XXXIX (FIG. 10). Ring fused cycloalkyl- or cycloalkanone-pyridine derivatives may be converted to cyclic vinyl bromides by those skilled in the art of organic synthesis. The vinyl bromide intermediates would be suitable substrates to undergo the tin cross-coupling methodology described in FIG. 5.

Compounds in which ring F contains an oxygen atom may be prepared starting with furyl-fused cycloalkanones or cycloalkenyl derivatives ($X=C_1-C_3$alkylene). Compounds in which ring F contains sulfur ring atoms may be prepared by starting with fused cycloalkenyl-thiophenes. Cycloalkyl ring-fused thienyl and furyl derivatives may be prepared using previously described literature procedures (Acta Chem. Scand. 25:1287 (1971); J. Am. Chem. Soc. 103:2760 (1981)) or modifications thereof. These intermediates can be converted to furyl- or thienyl-cyclopentanones or furyl- or thienyl-cyclopentenes. Alternatively the starting materials may be converted to the corresponding cyclic vinyl bromides by those skilled in the art of organic synthesis. The vinyl bromide intermediates may be used to give desired intermediates using the tin cross-coupling methodology described in FIG. 5.

Figure 11:
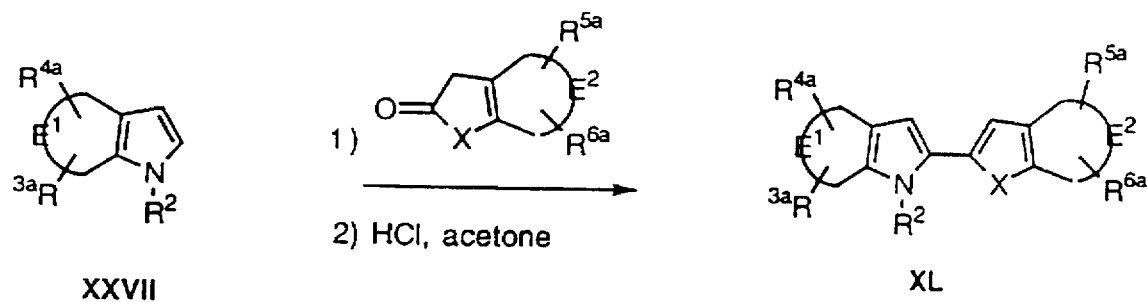
FIG. 11 is a schematic drawing outlining the chemical synthesis of intermediates (XL) to fused pyrrolocarbazoles in which both rings B and F contain ring heteroatoms.
Figure 12:
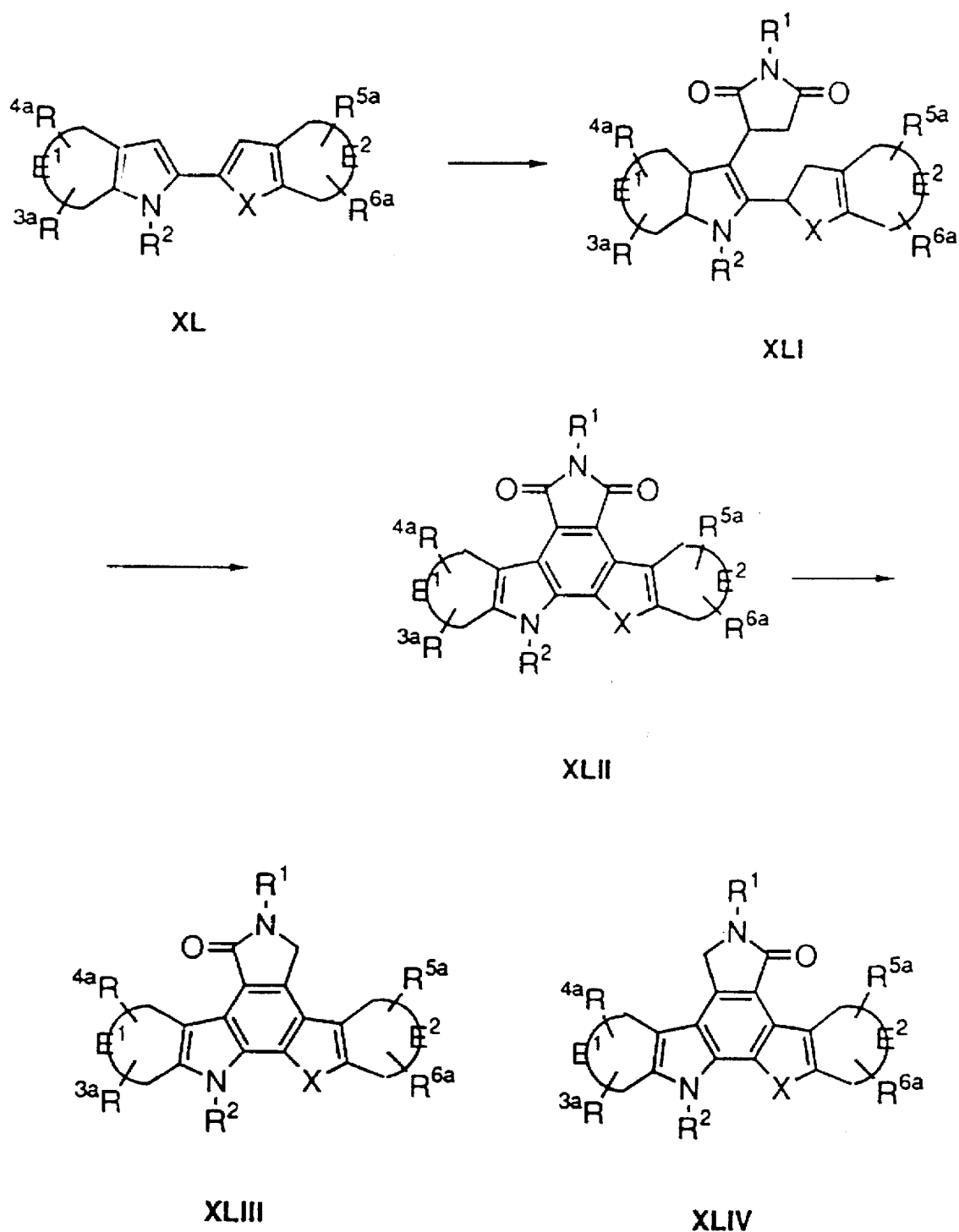
FIG. 12 is a schematic drawing outlining the conversion of intermediates (XL) to isomeric fused pyrrolocarbazoles (XLIII and XLIV) in which both rings B and F contain ring heteroatoms.

Rings B and F may both be substituted by heteroatoms simultaneously as shown in FIG. 11. Intermediate XL may be formed from a hetero atom-substituted B-ring intermediate (XXVII) and an F-ring hetero atom-substituted cyclic ketone or vinyl bromide intermediate as shown in FIG. 8 and FIG. 5. Imide and lactam derivatives containing hetero atoms in the B and F rings may be prepared by the methods shown in FIGS. 8 and 9. Alternatively, the palladium catalyzed cross-coupling methodology described in FIG. 6 may be used to prepare imide derivatives of the general structure XLII (FIG. 12). Reduction of the imide by the methods described (FIG. 8) would give lactam isomers XLIII and XLIV (FIG. 12).

A. Specific Description of Synthetic Processes FIG. 2: Synthesis of Fused Pyrrolocarbazoles (Method A)

Part IA

Step-1A: Preparation of 2-(2-(2-Hydroxy)indanyl)indole (FIG. 2, V, $R^2$, $R^3$=H, $X=CH_2$)

n-BuLi (107.5 mmol, 43 mL of 2.5M solution in hexanes) was added dropwise (15 min) to a solution (12.0 g, 102.4 mmol) of indole (FIG. 2 I, $R^2$, $R^3$=H) in dry THF (400 mL) at −78° C. (nitrogen atmosphere). The solution was stirred for 30 min, then $CO_2$(g) was passed through the solution for 10 min. The clear solution was allowed to warm to ambient temperature, then it was concentrated to half the original volume at reduced pressure. THF (200 mL) was added and the solution re-cooled to −78° C. At this point, t-BuLi (102 mmol, 60 mL of 1.7M solution in hexanes) was added dropwise (45 min). The resulting yellow solution was allowed to stir for 2 h at −78° C. Next, 2-Indanone (15.0 g, 112.6 mmol) in THF (100 mL) was added dropwise (30 min) and the mixture stirred for 1 hour. The reaction was quenched by addition of water (5 mL); the resulting mixture was poured into saturated $NH_4Cl$ solution (250 mL), and then extracted with ether (1×200 mL). The ether layer was washed with 100 mL saturated $NH_4Cl$, dried ($MgSO_4$), and concentrated at reduced pressure to give an oily product. The product (V) was recrystallized from $Et_2O$-hexane to give 10.5 g of a tan powder with an mp of 244°–245° C. The following NMR data were obtained: $^1H$ NMR ($CDCl_3$): δ2.4 (bs, 1H), 3.3 (d, 2H), 3.6 (d, 2H), 6.4 (s, 1H), 7.1–7.4 (m, 7H), 7.6 (d, 1H), 8.6 (bs, 1H). Anal. calc. $C_{17}H_{15}NO$; C, 81.90; H, 6.06; N, 5.62. Found C, 82.16; H, 6.03; N, 5.58.

The mother liquor was concentrated to yield an oily product. Column chromatography (silica gel, EtOAc:hexane 1,2) yielded an additional 2.1 g of product for a total yield of 12.6 g (49%).

Step-2A: Preparation of 2-(2-Indenyl)indole (FIG. 2, VI)

To a stirred solution of 2-(2-(2-hydroxy)indanyl)indole (FIG. 2, V, $R^2$, $R^3$=H, $X=CH_2$) (4.0 g, 16.1 mmol) in acetone (30 mL) was added 2N HCl (10 mL). The mixture was stirred at ambient temperature for 1 hour. About 20 mLs of water were added and the precipitate collected by filtration. The filtrate was washed well with water and dried to give 3.6 g (98%) of a white solid product with an mp of 273°–274° C. (MeOH). The following NMR data were obtained: $^1H$ NMR ($CDCl_3$): δ3.9 (s, 2H), 6.7 (s, 1H), 7.0–7.6 (m, 9H), 8.3 (bs, 1H). Anal.calc. $C_{17}H_{13}N$, C, 88.28; H, 5.67; N, 6.06. Found C, 88.11; H, 5.60; N, 5.98.

Step-3A: Preparation of 4c,7a,7b,12a-Tetrahydro-6H,12H,13H-indeno[2,3-a]pyrrolo [3,4-c]carbazole-5,7-(5H,7H) dione (FIG. 2 VII, $R^2$, $R^3$, R=H, $X=CH_2$).

A mixture of 2-(2-indenyl)indole (FIG. 2, VI, R, $R^2$, $R^3$=H, $X=CH_2$) (1.0 g, 4.3 mmol) and maleimide (525 mg, 5.41 mmol) in a 10 cm sealed reaction vial was heated at 180°–190° C. for 30 min. After cooling the reaction to ambient temperature, MeOH (5 mL) was added. The product (VII) was collected to give 880 mg (62%) of a white solid product with a mp of 254°–255° C. (MeOH). The following NMR data were obtained: $^1$H NMR (DMSO-$d_6$, 300 MHz): δ3.1–3.4 (m, 2H), 3.8 (m, 2H), 3.95 (t, 1H), 4.35 (d, 1H), 6.9–7.4 (m, 7H), 7.75 (d, 1H), 11.05 (s, 1H), 11.25 (s, 1H).

EXAMPLE V(A)(1)

Step-4A: Preparation of 6H,12H,13H-Indeno[2,3-a]pyrrolo [3,4-c]carbazole-5,7(5H, 7H)-dione (FIG. 2, VIB, Compound III)

Compound VII (FIG. 2, $R^2$, $R^3$, $R$=H) (800 mg, 2.44 mmol) was dissolved in toluene (60 mL). Solid 2,3-dichloro-5,6-dicyano-1,4-benzoquinone (1.4 g, 6.1 mmol) was added to the toluene solution in one portion. The solution was maintained at 60°–65° C. for 6 hours. After cooling on an ice bath, the solid product was collected by filtration, resuspended in MeOH (20 mL) and collected by filtration. The product (VIII) was recrystallized from acetone-MeOH to yield 710 mg (90%) of a yellow solid product with a mp greater than 330° C. The following NMR data were obtained: $^1$H NMR (DMSO-$d_6$, 300 MHz): δ4.3 (s, 2H), 7.35 (t, 1H), 7.45–7.65 (m, 4H), 7.75 (d, 1H), 8.95 (d, 1H), 9.1 (d, 1H), 11.15 (s, 1H, 12.3 (s, 1H). MS(FAB): m/e 325 (m+1)$^+$. Anal. calc. for $C_{21}H_{12}N_2O_2$. 0.75 $H_2O$: C, 74.65; H, 4.03; N, 8.29 Found: C, 74.40; H, 3.75; N, 8.26.

EXAMPLES V(A)(2) and (3)

Preparation of 6H,7H,12H,13H-Indeno[2,3-a]pyrrolo[3,4-c] carbazole-5(5H)one (FIG. 2, IX, Compound I-3) and 5H,6H, 12H,13H-Indeno[2,3-a]pyrrolo[3,4-c]carbazole-7(7H)one (FIG. 2, X, Compound I-2)

A stirred suspension of Zn dust (5 g) and mercuric chloride (1 g) was made in 10 mL water. Concentrated hydrochloric acid (2ml) was added dropwise. After 10 min, the aqueous layer was decanted and removed. The zinc amalgam obtained was first washed with water, then repeatedly with EtOH. The zinc amalgam was suspended in EtOH (75 mL). Next, solid Compound VIII (500 mg, 1.5 mmol, R, $R^2$, $R^3$=H, X=$CH_2$)) was added in one portion. HCl(g) was passed through as the mixture was maintained at reflux for 2 hours. After cooling to ambient temperature, the solution was concentrated at reduced pressure to yield an oily product. THF-EtOAc (200 mL, 1:1) was added to the oily product and the mixture was extracted with a saturated $NaHCO_3$ solution (3×100 mL), saturated NaCl solution (3×100 mL) and the resulting solution dried ($MgSO_4$). The drying agent was removed, and the solvent was concentrated at reduced pressure to give a crude solid. Purification by column chromatography (silica gel, 95:5, EtOAc:MeOH) yielded 240 mg (50%) of a 4:1 mixture of Compound I-3 and 1-2. The following NMR data were obtained: $^1$H NMR (DMSO-$d_6$, 300 MHz): δ4.15 (s, 1.6H), 4.25 (s, 0.4H), 4.9 (s, 0.4H), 4.95 (s, 1.6H), 7.2–7.8 (m, 6H), 8.0 (d, 1H), 8.6 (s, 0.8H), 8.8 (s, 0.2H), 9.2 (d, 0.2H), 9.4 (d, 0.8H), 11.8 (s, 0.2H), 11.95 (s, 0.8H). MS(FAB), m/e 311 (m+1)$^+$.

B. Specific Description of Synthetic Processes FIG. 3: Synthesis of Fused Pyrrolocarbazoles (Method B)

Part IIB.

Step-1B: Preparation of 3-Cyano-4-ethoxycarbonyl-1,2,3,4-tetrahydro-[1H]indeno[2,3-a]9H-carbazole (XII) and 4-Cyano-3-ethoxycarbonyl-1,2,3,4-tetrahydro-[1H]indeno [2,3-a]9H-carbazole (XV)

Step-1: A mixture of 2-(2-indenyl)indole (VI) ($R^2$, $R^3$, $R^4$, $R^5$, $R^6$=H, X=$CH_2$, 3.5 g, 15.2 mmol) and ethyl cis-β-cyanoacrylate (10 g, 80 mmol) in a sealed reaction flask, was heated to 190° C. with stirring for 1.5 hours. The mixture was cooled to ambient temperature, MeOH (20 mL) was added and the solution was cooled to –20° C. Compound XV was collected from the filtrate to give 1.65 g (31%) of a light yellow solid with an mp of 270°–272° C. (acetone-MeOH). The following NMR data were obtained: 1H NMR (DMSO-$d_6$, 300 MHz): δ1.3 (t, 3H), 3.1–3.4 (m, 3H), 3.7 (m, 1H), 3.9 (t, 1H), 4.4 (m, 2H), 4.6 (d, 1H), 6.95–7.2 (m, 6H), 7.3 (d, 1H), 7.45 (d, 1H), 11.3 (s, 1H). IR (KBr) cm$^{-1}$: 2210 (CN); 1690 (C=O). MS(FAB): m/e 356 (m$^+$).

The filtrate XV was concentrated at reduced pressure to yield a viscous oily product. The excess ethyl cis-β-cyanoacrylate was removed by Kugelrohr distillation (oven temperature 80°–85° C., 0.5 mm). Ether was added and the Compound XII ($R^2$, $R^3$, $R^4$, $R^5$, $R^6$=H, X=$CH_2$) was crystallized from the residue to give 650 mg (12%) of an off-white solid with an mp of 206°–207° C. (acetone-MeOH). The following NMR data were obtained: $^1$H NMR (DMSO-$d_6$ 300MHz): δ1.15 (t, 3H), 3.1–3.25 (m, 1H), 3.4–3.5 (m, 1H), 3.8 (q, 1H), 3.9 (m, 1H), 4.05 (t, 1H), 4.2–4.3 (m, 3H), 6.95 (t, 1H), 7.1 (t, 1H), 7.2–7.4 (m, 5H), 7.55 (m, 1H), 11.35 (s, 1H). MS(FAB): m/e=356 (m$^+$).

Step-2B: Preparation of 3-Cyano-4-ethoxycarbonyl-indeno [2,3-a]9H-carbazole (FIG. 3, XIII ($R^2$, $R^3$, $R^4$, $R^5$, $R^6$=H, X=$CH_2$))

Compound XII (400 mg, 1.12 mmol) was dissolved in dry toluene (50 mL). 2,3-Dichloro-5,6-dicyano-1,4-benzoquinone (640 mg, 2.8 mmol) was added to the stirred solution in one portion. The solution was stirred at 60°–65° C. for 6 hours. After cooling on an ice bath, the precipitate was collected by filtration, the product was suspended in MeOH (20 mL), collected and washed with cold MeOH (10 mL) to yield 355 mg (90%) of a light green solid with an mp of 292°–293° C. (acetone). The following NMR data were obtained: $^1$H NMR (DMSO-$d_6$, 300 MHz): δ1.4 (t, 3H), 4.3 (s, 2H), 4.7 (q, 2H), 7.3 (m, 1H), 7.4–7.7 (m, 4H), 7.8 (d, 1H), 8.05 (d, 1H), 8.45 (d, 1H), 12.5 (s, 1H). IR (KBr) cm$^{-1}$ 2210 (CN); 1710 (C=O). MS(FAB): m/e 353 (m+1)$^+$. Anal. calc. $C_{23}H_{16}N_2O_2$: C, 78.39; H, 4.58; N, 7.95. Found: C, 78.61; H, 4.28; N, 7.75.

EXAMPLE V(B)(1)

Step-3B: Preparation of 6H,7H,12H,13H-Indeno[2.3-a] pyrrolo[3,4-c]carbazole-5(5H)one (FIG. 3, XIV, Compound I-3)

A mixture of Compound XIII (300 mg; 0.85 mmol) and Raney Nickel catalyst (ca. 1 g, wet form) in MeOH/THF (125/25 mL) was hydrogenated at 35 psi on a Parr Apparatus for 12 hours. The resulting solution was diluted with THF (50 mL), and then filtered through celite. The solvent was concentrated at reduced pressure and the product purified by column chromatography (silica gel; EtOAc:Hex; 2:1, $R_f$=0.3). The product fractions were collected and concentrated to give a white solid. This solid was triturated with MeOH (10 mL), collected by filtration and dried (100° C., 0.5 mm, 12 hours) to give 140 mg (53%) of Compound I-3 as a white solid with a mp of greater than 300° C. (THF-MeOH). The following NMR data were obtained: $^1$H NMR (DMSO-$d_6$, 300 MHz) δ4.25 (s, 2H), 4.9 (s, 2H), 7.2 (t, 1H), 7.35–7.5 (m, 3H), 7.6 (d, 1H), 7.8 (t, 1H), 8.8 (s, 1H, 9.2 (d, 1H), 11.85 (s, 1H). MS(FAB): m/e=311 (M+1)$^+$. Anal. calc.: $C_{21}H_{14}N_2O$ 0.4 $H_2O$; C, 79.42; H, 4.65; N, 8.82. Found: C, 79.54; H, 4.60; N, 8.70.

Step-4B: Preparation of 4-Cyano-3-ethoxycarbonyl-indeno [2,3-a]9H-carbazole (FIG. 3, XVI, $R^2$, $R^3$, $R^4$, $R^5$, $R^6$=H, X=$CH_2$))

To a stirred solution of Compound XV (1.1 g, 3.1 mmol; $R^2$, $R^3$, $R^4$, $R^5$, $R^6$=H, X=$CH_2$)) in dry toluene (70 mL) was added 2,3-dichloro-5,6-dicyano-1,4-benzoquinone (1.75 g, 7.7 mmol) in one portion. The solution was stirred at 60°–65° C. for 6 hours. After cooling on an ice bath, the precipitate was collected by filtration, the product was suspended in MeOH (40 mL), collected and washed with cold MeOH (10 mL) to give 975 mg (89%) of a light green solid (XVI; $R^2$, $R^3$, $R^4$, $R^5$, $R^6$=H, X=$CH_2$) with an mp of 260°–263° C. (acetone). The following NMR data were obtained: $^1$H NMR (DMSO-$d_6$, 300 MHz): δ1.4 (t, 3H), 4.35 (s, 2H), 4.6 (q, 2H), 7.3–7.5 (m, 3H), 7.5–7.8 (m, 5H), 8.5 (d, 1H), 12.6 (s, 1H) IR (KBr) $cm^{-1}$ : 2210 (CN); 1710 (C=O). MS(FAB): m/e 353 (m+1)$^+$. Anal. calc. $C_{23}H_{16}N_2O_2$: C, 78.39; H, 4.58; N, 7.95. Found: C, 78.77; H, 4.39; N, 7.71.

EXAMPLE V(B)(2)

Step-5B: Preparation of 6H,7H,12H,13H-Indeno[2,3-a]pyrrolo[3,4-c]carbazole-5(5H)one A mixture of Compound XVI (170 mg, 0.5 mmol) and Raney Nickel catalyst (approx. 500 mg, wet form) in MeOH/THF (3:175 mL) was hydrogenated at 35 psi on a Parr Apparatus for 12 hours. The solvent was diluted with THF (50 mL), and then filtered through celite. The solvent was concentrated at reduced pressure and the product was purified by column chromatography (silica gel, EtOAc:hexane, 2:1, $R_f$=0.3) to yield 115 mg (77%) of an off-white solid (XVII, compound I-2), mp>300° C. (THF-MeOH). The following NMR data were obtained: $^1$H NMR (DMSO-$d_6$, 300 MHz): δ4.15 (s, 2H), 4.95 (s, 2H), 7.2–7.5 (m, 4H), 7.65 (d, 1H), 7.7 (d, 1H), 8.0 (d, 1H), 8.6 (s, 1H), 9.4 (d, 1H), 11.95 (s, 1H). MS(FAB): m/e 311 (m+1)$^+$. Anal. calc. for: $C_{21}H_{14}N_2O$, 0.4 $H_2O$; C, 79.42; H, 4.65; N, 8.82. Found: C, 79.61; H, 4.56; N, 8.63.

C. Specific Description of Synthetic Processes Preparation of Halogenated Fused Pyrrolocarbazoles Part IIIA. Fluorinated Derivatives Step-1A: Preparation of 5-Fluoro-2-(2-(2-hydroxy)indanyl)indole This compound was prepared using substantially the same procedure as in Part IA, Step-1A, except that 5-fluoroindole was substituted for I.

5-Fluoro-2-(2-(2-hydroxy)indanyl)indole; yield 64%, mp 158°–161° C. dec (MeOH-ether). The following NMR data were obtained: $^1$H NMR (CDCl$_3$, 300 MHz): δ2.2 (bs, 1H), 3.35 (d, 2H), 3.6 (d, 2H), 6.4 (s, 1H), 6.95 (t, 1H), 7.2–7.35 (m, 6H), 8.6 (bs, 1H). Anal. calc. for: $C_{17}H_{14}FNO$; C, 76.36; H, 5.28; N, 5.24. Found: C, 76.70; H, 5.20; N, 5.08.

Step-2A: Preparation of 5-Fluoro-2-(2-indenyl)indole

This compound was prepared by substantially the same procedure as in Part IA, Step-2A.

5-Fluoro-2-(2-indenyl)indole; yield 95%, mp 233°–236° C. dec (MeOH-ether). The following NMR data were obtained: $^1$H NMR (CDCl$_3$, 300 MHz): δ3.85 (s, 2H), 6.65 (s, 1H), 6.9–7.5 (m, 9H), 8.3 (s, 1H). Anal. calc. for: $C_{17}H_{12}FNO$; C, 81.91; H, 4.85; N, 5.62. Found: C, 81.60; H, 4.75; N, 5.54.

Step-3A: Preparation of 3-Fluoro-4c,7a,7b,12a-tetrahydro-6H,12H,13H-indeno[2,3-a]pyrrolo[3,4-c]carbazole-5,7(5H,7H)-dione A mixture of 5-fluoro-2-(2-indenyl)indole (365 mg, 1.45 mmol) and maleimide (215 mg, 2.2 mmol) in a 10 cm sealed reaction vial was heated at 180°–190° C. for 30 min. After cooling the reaction to ambient temperature, ice-cold CH$_3$OH (4 mL) was added. The resulting crystals were collected by filtration to give 275 mg (55%) of product with an mp of 272°–275° C. (acetone-MeOH). The following NMR data were obtained: $^1$H NMR (DMSO-$d_6$, 300 MHz): δ3.1–3.4 (m, 2H), 3.7–3.8 (m, 2H), 3.95 (m, 1H), 4.3 (d, 1H), 6.9(m, 1H), 7.1–7.3 (m, 5H), 7.4 (d, 1H), 11.2–11.3 (d, 2H).

EXAMPLE V(C)(1)

Step-4A: Preparation of 3-Fluoro-6H,12H,13H-indeno[2,3-a]pyrrolo[3,4-c]carbazole-5,7(5H,7H)dione (Compound I-7)

To a solution of 3-fluoro-4c,7a,7b,12a-tetrahydro-6H,12H,13H-Indeno[2,3-a]pyrrolo[3,4-c]carbazole-5,7(5H,7H)dione (Part IIIA, Step-3) (250 mg, 0.73 mmol) in toluene (25 mL) was added solid 2,3-dichloro-5,6-dicyano-1,4-benzoquinone (410 mg, 1.8 mmol) in one portion. The mixture was heated at 45° C. for 6 hours. After cooling on an ice-bath, the precipitate was collected by filtration, and then resuspended in MeOH (10 mL). The product was collected by filtration and washed with cold MeOH (1×5 mL). Recrystallization from THF-MeOH-Et$_2$O gave 215 mg (86% yield) of Compound I-7. Compound I-7 exhibited an mp of greater than 275° C. The following NMR data were obtained: $^1$H NMR (DMSO-$d_6$, 300 MHz): δ4.25 (s, 2H); 7.35–7.55 (m, 3H); 7.65 (m, 1H); 7.75 (d, 1H); 8.6 (d, 1H): 9.1 (d, 1H); 11.3 (s, 1H); 12.35 (s, 1H). MS(FAB): m/e 343 (m+1)$^+$.

EXAMPLE V(C)(2)

Step-5A: Preparation of 3-Fluoro-6H,7H,12H,13H-indeno[2,3-a]pyrrolo[3,4-c]carbazole-5(5H)one and 3-fluoro-5H,6H,12H,13H-indeno[2,3-a]pyrrolo[3,4-c]carbazole-7(7H)one (Compound I-8)

A stirred suspension of Zn dust (1.3 g) and mercuric chloride (200 mg) in water (3 mL) was made and 0.5 mL concentrated hydrochloric acid was added dropwise. After five minutes, the aqueous layer was decanted. The zinc amalgam was first washed with water, then washed repeatedly with EtOH. The zinc amalgam was suspended in EtOH (20 mL), and 75 mg, (0.22 mmol) solid Compound I-7 was added in one portion. HCl(g) was passed through the solution while the solution was maintained at reflux for 1 hour. After cooling to ambient temperature, the solution was concentrated at reduced pressure to give a crude solid. The solid was dissolved in THF-EtOAc (1:1, 100 mL) and extracted with saturated NaHCO$_3$ (2×100 mL), saturated NaCl solution (3×100 mL), and then dried (MgSO$_4$). The drying agent was removed by filtration and the solvent concentrated at reduced pressure. The product was purified by column chromatography (silica gel, 2:1, EtOAc:hexanes) $R^f$=0.3; to give 20 mg (28% yield) of the Compound I-8 mixture. The mixture exhibited an mp of greater than 300° C. The following NMR data were obtained: $^1$H NMR (DMSO-$d_6$, 300 MHz): δ4.15 (s, 1.34H); 4.25 (s, 0.66H); 4.9 (s, 0.66H); 4.95 (s, 1.34H); 7.2–7.85 (m, 6H); 8.6 (s, 0.67H); 8.85 (s, 0.33H); 8.9 (d, 0.33H); 9.4 (d, 0.67H); 11.95 (s, 0.33H); 12.0 (s, 0.67H). MS(FAB): m/e 329 (m+1)$^+$.

EXAMPLE V(C)(3) (Method B)

Step-1B: Preparation of 6-Fluoro-4-cyano-3-ethoxycarbonyl-1,2,3,4-tetrahydro[1H]indeno[2,3-a]9H-carbazole A mixture of 5-fluoro-2-(2-(2-hydroxy)indanyl)indole (Part IIIA, Step IA 1.5 g, 6.0 mmol) and ethyl cis-b- cyanoacrylate (10.0 g, 80 mmol), in a sealed reaction flask, was heated at 180° C. with stirring for 1.5 hours. The mixture was cooled to ambient temperature, MeOH (10 mL) was added and the solution cooled to −20° C. The product was collected to give 650 mg (29% yield) of a light tan solid with an mp of 301°–305° C. (MeOH). The following NMR data were obtained: $^1$H NMR (DMSO-$d_6$, 300 MHz): δ1.3 (t, 3H), 3.1–3.35 (m, 3H), 3.75 (s,m, 4H), 3.95 (m, 1H), 4.4 (q, 2), 4.65 (d, 1H) 6.9–7.0 (m, 1H), 7.02–7.4 (m, 6H), 11.4 (s, 1H). IR (KBr) cm$^{-1}$: 2210 (CN); 1690 (C=O).

Step-2B: Preparation of 6-Fluoro-4-cyano-3-ethoxycarbonyl[1H]indeno[2,3-a]9H-carbazole To a stirred solution of 6-fluoro-4-cyano-3-ethoxycarbonyl-1,2,3,4-tetrahydro-[1H]-indeno[2,3-a]9H-carbazole (Example V(C)3, Step-1B) (400 mg, 1.1 mmol) in dry toluene (40 mL) was added 2,3-dichloro-5,6-dicyano-1,4-benzoquinone (600 mg, 2.7 mmol) in one portion. The solution was stirred at 65°–70° C. for 6 hours. After cooling on an ice bath the precipitate was collected by filtration, the product was suspended in MeOH (20 mL), collected again, then washed with cold MeOH (10 mL) to give 375 mg (92% yield) of a light yellow product with an mp of 256°–258° C. (acetone). The following NMR data were obtained: $^1$H NMR (DMSO-$d_6$, 300 MHz): δ1.4 (t, 3H), 4.3 (s, 2H), 4.7 (q, 2H), 7.0 (m, 1H), 7.1 (m, 1H), 7.15 (m, 1H), 7.4–7.9 (m, 4H), 12.5 (s, 1H). IR (KBr) cm$^{-1}$: 2210 (CN); 1710 (C=O). MS(FAB): m/e 370 (m)$^+$.

Step-3B: Preparation of 3-Fluoro-5H,6H,12H,13H-indeno [2,3-a]pyrrolo[3,4-c]carbazole-7(7H)one (Compound I-12)

A mixture of 6-fluoro-4-cyano-3-ethoxycarbonyl-[1H]-indeno[2,3-a]9H-carbazole (Example V(C)3, Step-2B): (100 mg, 0.27 mmol) and Raney Nickel catalyst (approx. 500 mg, wet form) in THF/MeOH (50 mL) was hydrogenated at 35 psi on a Parr Apparatus for 12 hours. THF (50 mL) was added and the solvent filtered through Celite® diatomaceous earth and concentrated at reduced pressure. The product was purified by column chromatography (silica gel, EtOAc:hexane, 2:1, $R_f$=0.3) to give 15 mg(17% yield) of Compound I-12 as an off-white solid. Compound I-12 exhibited an mp of greater than 300° C. The following NMR data were obtained: $^1$H NMR (DMSO-$d_6$, 300 MHz): δ4.18 (s, 2H), 4.95 (s, 2H), 7.3–7.45 (m, 4H), 7.6–7.75 (m, 2H), 7.83 (d, 1H), 8.6 (s, 1H), 9.4 (d, 1H); 12.0 (s, 1H). MS(FAB): m/e 329 (m+1)$^+$.

EXAMPLE V(C)(4)

Preparation of 3-Fluoro-6H,7H,12H,13H-indeno[2,3-a] pyrrolo[3,4-c]carbazole-5(5H)one (Compound I-23)

To a stirred solution of 6-fluoro-4-cyano-3-ethoxycarbonyl-1,2,3,4-tetrahydro-[1H]-indeno[2,3-a]9H-carbazole (Example V(C)3, step-2B) (230 mg, 0.6 mmol) in dry toluene (25 mL) was added 2,3-dichloro-5,6-dicyano-1,4-benzoquinone (340 mg, 1.5 mmol) in one portion. The solution was stirred at 65°–70° C. for 6 hours. After cooling on an ice bath, the precipitate was collected by filtration, the product was suspended in MeOH (20 mL), collected and washed with cold MeOH (10 mL) to yield 160 mg (70%) of a light yellow solid. The melting point was >300° C. (acetone). The following NMR data were obtained: $^1$H NMR (DMSO-$d_6$, 300 MHz): δ1.45 (t, 3H, J=6 Hz), 4.3 (s, 2H), 4.65 (q, 2H, J=6 Hz), 7.4–7.6 (m, 3H), 7.62–7.68 (m, 1H), 7.75–7.82 (m, 2H), 8.5 (d, 1H, J=8 Hz), 12.55 (s, 1H). IR (KBr) cm$^{-1}$: 2210 (CN); 1710 (C=O). MS(FAB): m/e 370 (m)$^+$.

Preparation of 3-Fluoro-6H,7H,12H,13H-indeno[2,3-a] pyrrolo[3,4-c]carbazole-5(5H)one (Compound I-23)

A mixture of 6-fluoro-4-cyano-3-ethoxycarbonyl-[1H]-indeno[2,3-a]9H-carbazole (125 mg, 0.34 mmol; Example V(C)3, Step-3B) and Raney Nickel catalyst (approx. 500 mg, wet form) in THF (50 mL) was hydrogenated at 35 psi on a Parr Apparatus for 12 hours. THF (50 mL) was added and then the solution was filtered through Celite® and concentrated at reduced pressure to give 75 mg of crude product. The product was purified by HPLC to give Compound I-23 as a white solid. The melting point was greater than 300° C. The following NMR data were obtained: $^1$H NMR (DMSO-$d_6$, 300 MHz): δ4.26 (s, 2H), 4.9 (s, 2H), 7.25–7.60 (m, 4H), 7.75–8.05 (m, 2H), 8.83 (s, 1H), 8.9 (d, 1H, J=10 Hz), 11.88 (s, 1H). MS(FAB): m/e 329 (m+1)$^+$.

D. Specific Description of Synthetic Processes
Preparation of Chlorinated Fused Pyrrolocarbazoles Part IIIB. Chlorinated Derivatives
Step-1A: Preparation of 6-Chloro-2-(2-(2-hydroxy)indanyl) indole This compound was prepared by substantially the same procedure as Part IA, Step 1A, except that 6-chloroindole was substituted for I.

6-Chloro-2-(2-(2-hydroxy)indanyl)indole: yield (24%); mp 202°–204° C. (MeOH-ether). The following NMR data were obtained: $^1$H NMR (CDCl$_3$, 300 MHz): δ2.35 (s, 1H, 3.35 (d, 2H), 3.6 (d, 2H), 6.4 (s, 1H), 7.05 (d, 1H), 7.2–7.4 (m, 5H), 7.45 (d, 1H), 8.6 (s, 1H).

Step-2A: Preparation of 6-Chloro-2-(2-indenyl)indole

This compound was prepared by substantially the same procedure as Part IA, Step-2A.

6-Chloro-2-(2-indenyl)indole; yield 94%; mp 215°–218° C. dec (MeOH-ether). The following NMR data were obtained: $^1$H NMR (CDCl$_3$, 300 MHz): δ3.9 (s, 2H), 6.65 (s, 1H), 7.0–7.65 (m, 8H), 8.25 (s, 1H).

Step-3A: Preparation of 2-Chloro-4c,7a,7b,12a-tetrahydro-12H,13H-indeno[2,3-a]pyrrolo[3,4-c]carbazole-6H-5,7-(5H,7H)-dione.

A mixture of 6-chloro-2-(2-indenyl)indole (210 mg, 0.8 mmol) and maleimide (160 mg, 1.7 mmol) in a 10 cm sealed reaction vial was heated at 180°–190° C. for 1 hour. After the mixture was cooled to ambient temperature, the product was dissolved in MeOH (4 mL). Et$_2$O (5 mL) and hexane (10 mL) were added to precipitate the product as an oil. The oil solidified to a yellow solid product on standing. Purification by column chromatography (silica gel, EtOAc:hexanes, 2:1) gave 200 mg (69% yield) of product with an mp of greater than 225° C. The following NMR data were obtained: $^1$H NMR (DMSO-$d_6$, 300 MHz): δ3.0–3.3 (m, 2H), 3.75 (m, 2H), 3.9 (t, 1H), 4.3 (d, 1H), 6.9–7.3 (m, 6H), 7.7 (d, 1H), 11.2 (s, 1H), 11.35 (s, 1H).

EXAMPLE V(D)(1)

Step-4: Preparation of 2-Chloro-6H,12H,13H-indeno[2,3-a] pyrrolo[3,4-c]carbazole-5,7(5H,7H)-dione (Compound Ia-1)

To a solution of 2-chloro-4c,7a,7b,12a-tetrahydro-6H, 12H,13H-indeno[2,3-a]pyrrolo[3,4-c]carbazole-5,7-(5H, 7H)-dione (250 mg, 0.7 mmol) in toluene (50 mL) was added solid 2,3-dichloro-5,6-dicyano-1,4-benzoquinone (400 mg, 1.7 mmol) in one portion. The mixture was stirred at 60°–65° C. for 4 hours. The solution was cooled in an ice bath and the precipitate collected by filtration. The product was resuspended and triturated with MeOH (10 mL). The product was collected and recrystallized from THF-MeOH-Et20 to give 210 mg (85% yield) of Compound Ia-1 as a yellow solid product with an mp of greater than 300° C. The following NMR data were obtained: $^1$H NMR (DMSO-$d_6$, 300 MHz): δ4.25 (s, 2H), 7.3(d, 2H), 7.4–7.5 (m, 2H), 7.6

(s, 1H);, 1H), 8.85 (d, 1H), 9.05 (d, 1H), 11.15 (s, 1H), 12.35 (s, 1H). MS(FAB): m/e 359 (m+1)⁺.

EXAMPLE V(D)(2)

Preparation of 2-Chloro-6H,7H,12H,13H-indeno[2,3-a] pyrrolo[3,4-c]carbazole-5(5H)one and 2-chloro-5H,6H, 12H,13H-indeno[2,3-a]pyrrolo[3,4-c]carbazole-7(7H)one (Compound Ia-2)

To a stirred suspension of Zn dust (1.5 g) and mercuric chloride (400 mg) in water (5 mL) was added (dropwise) 1 mL concentrated hydrochloric acid. After 10 minutes, the aqueous layer was decanted. The zinc amalgam was first washed with water, then repeatedly with EtOH. The zinc amalgam was suspended in EtOH (25 mL), and solid Compound II-1 (120 mg, 0.34 mmol) was added in one portion. HCl(g) was passed through while the solution was maintained at reflux for 4 hours. After cooling to ambient temperature, the solution was concentrated at reduced pressure. The residue was dissolved in THF-EtOAc (1:1, 100 mL) and extracted with saturated NaHCO₃ (2×100 mL), saturated NaCl solution (2×100 mL), and dried (MgSO₄). The drying agent was removed by filtration and the solvent concentrated at reduced pressure to give a crude solid. The product was purified by column chromatography (silica gel, EtOAc:hexanes, 2:1), $R_f$=0.35, to give 65 mg (56% yield) of the Compound Ia-2 mixture. The mixture exhibited an mp of greater than 300° C. The following NMR data were obtained: ¹H NMR (DMSO-d₆, 300 MHz): δ4.15 (s, 1.6H), 4.2 (s, 0.4H), 4.9 (d, 1H), 7.2–7.5 (m, 3H), 7.55–7.8 (m, 2H), 8.0 (d, 1H), 8.6 (s, 0.8H), 8.8 (s, 0.2H), 9.1 (d, 0.2H), 9.4 (d, 0.8H), 11.95 (s, 0.2H), 12.05 (s, 0.8H). MS(FAB): m/e 345 (m+1)⁺.

EXAMPLE V(D)(3)

Step-1A: Preparation of 5-Chloro-2-(2-(2-hydroxy)indanyl) indole

This compound was prepared by substantially the same procedure as Part IA, Step-1A except that 5-chloroindole was substituted for I.

5-Chloro-2-(2-(2-hydroxy)indanyl)indole, yield 1.7 g (36%) mp 254°–256° C. (ether-hexane), ¹H NMR (CDCl₃) δ2.3 (bs, 1H), 3.35 (d, 2H), 3.6 (d, 2H), 6.35 (s, 1H), 7.1–7.4 (d, 6H), 7.6 (s, 1H), 8.6 (s, 1H).

Step-2A: Preparation of 5-Chloro-2-(2-indenyl)indole

This compound was prepared by substantially the same procedure as Part IA, Step-2A.

5-Chloro-2-(2-indenyl)indole; yield 1.35 g (96%) mp 260°–263° C. (ether-hexane) ¹H NMR (CDCl₃) δ3.85 (s, 2H), 6.65 (s, 1H), 7.05 (s, 1H), 7.15 (d, 1H), 7.2–7.35 (m, 3H), 7.4 (d, 1H), 7.5 (d, 1H), 8.25 (bs, 1H).

Step-3A: Preparation of 3-Chloro-4c,7a,7b,12a-tetrahydro-6H,12H,13H-indeno[2,3-a]pyrrolo[3,4-c]carbazole-5,7-(5H,7H)-dione.

A mixture of 5-chloro-2-(2-indenyl)indole (280 mg, 1.1 mmol) and maleimide (200 mg, 2.1 mmol) in a 10 cm sealed reaction vial was heated at 180°–190° C. for 1 hour. After the mixture was cooled to ambient temperature, MeOH (4 mL) was added. The solution was cooled to −20° C. and the product was collected as a white solid. Recrystallization from acetone-MeOH-Ether gave 250 mg as a white solid product (63%) mp 292°–293° C. The following NMR data were obtained: ¹H NMR (DMSO-d₆, 300 MHz): δ3.05–3.3 (m, 2H), 3.7–3.8 (m, 2H), 3.95 (m, 1H), 4.3 (d, 1H), 7.0–7.35 (m, 6H), 7.7 (s, 1H), 11.3 (s, 1H), 11.4 (s, 1H).

Step-4A: Preparation of 3-Chloro-6H,12H,13H-indeno[2,3-a]pyrrolo[3,4-c]carbazole-5,7(5H,7H)-dione (Compound I-10)

Solid 2,3-dichloro-5,6-dicyano-1,4-benzoquinone (345 mg, 1.52 mmol) was added in one portion to a solution of 3-chloro-4c,7a,7b,12a-tetrahydro-6H,12H,13H-indeno[2,3-a]pyrrolo[3,4-c]carbazole-5,7-(5H,7H)-dione (220 mg, 0.61 mmol) in toluene (50 mL). The mixture was stirred at 60°–65° C. for 4 hours. The solution was cooled in an ice bath and the precipitate collected by filtration. The product was resuspended and tritiated with MeOH (10 mL). The product was collected and recrystallized from THF-MeOH-Et₂O to give 210 mg (96%) of Compound I-10 as a yellow solid product. The melting point was greater than 320° C. The following NMR data were obtained: ¹H NMR (DMSO-d₆, 300 MHz): δ4.2 (s, 2H), 7.4–7.65 (m, 4H), 7.75 (d, 1H), 8.89 (s, 1H), 9.05 (d, 1H, 11.3 (s, 1H); 12.4 (s, 1H). MS(FAB): m/e 359 (m+1)⁺. Anal. calc. for C₂₁H₁₁ClN₂O₂: C, 69.47; H, 3.19; N, 7.72. Found C, 69.29; H, 3.04; N, 7.60.

E. Specific Description of Synthetic Processes Preparation of Brominated Fused Pyrrolocarbazoles Part IIIC. Brominated and Iodinated Derivatives

EXAMPLE V(E)(1)

Preparation of 3-Bromo-6H,12H,13H-indeno[2,3-a]pyrrolo [3,4-c]carbazole-5,7(5H,7H)-dione (Compound I-6)

Solid N-bromosuccinimide (55 mg, 0.31 mmol) was added in one portion to a stirred solution of Compound I-1 (100 mg, 0.31 mmol) in dry THF (5 mL), under a nitrogen atmosphere. The mixture was stirred at ambient temperature for 2 hours. The dark solution was diluted with EtOAc (5 mL) and sequentially washed with a 5% aqueous Na₂S₂O₃ solution (1×10 mL), water (1×10 mL), saturated NaCl solution (2×10 mL) and dried (MgSO₄). The solvent was concentrated at reduced pressure to give 85 mg (68% yield) of a crude product. Recrystallization in THF-MeOH gave Compound I-6 as a yellow powder with an mp of greater than 300° C. The following NMR data were obtained: ¹H NMR (DMSO-d₆, 300 MHz): δ4.25 (s, 2H), 7.4–7.8 (m, 5H), 9.0–9.05 (d, s, 2H), 11.3 (s, 1H), 12.4 (s, 1H). MS(FAB): m/e 404 (m+1)⁺.

EXAMPLE V(E)(2)

Preparation of 3-Bromo-6H,7H,12H,13H-indeno[2,3-a] pyrrolo[3,4-c]carbazole-5(5H)one (Compound I-11)

Solid N-bromosuccinimide (20 mg, 0.1 mmol) was added to a stirred solution of compound I-3 (Example V(B)(1)) (30 mg, 0.1 mmol) in dry THF (5 mL) under a nitrogen atmosphere. The solution was stirred at ambient temperature for 6 hours, then stored at −20° C. for 24 hours. The product was collected by filtration to give 30 mg (80% yield) of Compound I-11 as a light yellow solid product with an mp of greater than 340° C. (THF-MeOH). The following NMR data were obtained: ¹H NMR (DMSO-d₆, 300 MHz): δ4.3 (s, 2H), 4.9 (s, 2H), 7.35–7.45 (m, 2H), 7.55 (bs, 2H), 7.7–7.85 (m, 2H), 8.9 (s, 1H), 9.35 (s, 1H), 12.05 (s, 1H). MS(FAB): m/e 389 (m⁺). Anal. calc. for: C₂₁H₁₃BrN₂O. 0.4 H₂O: C, 63.50; H, 3.33; N, 6.86. Found: C, 63.61; H, 3.51; N, 7.07.

EXAMPLE V(E)(3)

Preparation of 3-Bromo-5H,6H,12H,13H-indeno[2,3-a] pyrrolo[3,4-c]carbazole-7(7H)one (Compound Solid N-bromosuccinimide (20 mg, 0.1 mmol) was added to a stirred solution of Compound I-2 (30 mg, 0.1 mmol) in dry THF (7 mL) under a nitrogen atmosphere. The solution was stirred at ambient temperature 6 hours, then stored at −20° C. for 12 hours. The product was collected by filtration to give 32 mg (84% yield) of a white solid (Compound I-9). Compound I-9 exhibited an mp of greater than 320° C. (THF-MeOH). The following NMR data were obtained: $^1$H NMR (DMSO-d$_6$, 300 MHz): δ4.2 (s, 2H), 4.95 (s, 2H), 7.3–7.5 (m, 2H), 7.6 (bs, 2H), 7.7 (d, 1H), 8.15 (s, 1H), 8.6 (s, 1H), 9.4 (d, 1H), 12.15 (s, 1H). MS(FAB): m/e 389 (m$^+$). Anal. calc. for: C$_{21}$H$_{13}$BrN$_2$O: C, 64.80; H, 3.37; N, 7.20. Found: C, 64.62; H, 3.63; N, 6.7.

EXAMPLE V(E)(4)

Step-1A: Preparation of 2-(2-(2-hydroxy-5-bromo)indanyl) indole

This compound was prepared by substantially the same procedure as Part IA, Step-1A except that 5-bromo-2-indanone was substituted for I.

2-(2-(2-hydroxy-5-bromo)indanyl)indole yield 500 mg (31%) mp 158°–160° C. (ether-hexane), $^1$H NMR (CDCl$_3$) δ2.3 (bs, 1H), 3.25–3.4 (dd, 4H), 6.4 (s, 1H), 7.1–7.4 (m, 6H), 7.6 (d, 1H), 8.6 (s, 1H).

Step-2A: Preparation of 2-(2-(5-bromoindenyl)indole and 2-(2-(6-bromoindenyl)indole This compound was prepared by substantially the same procedure as Part IA, Step-2A.

2-(2-(5-bromoindenyl)indole and 2-(2-(6-bromoindenyl) indole; $^1$H NMR (CDCl$_3$) δ3.8 (d, 2H), 6.7 (s, 0.5H), 6.95 (s, 0.5H), 7.1–7.6 (m, 6H), 8.25 (bs, 1H).

Step-3A: Preparation of 4c,7a,7b,12a-Tetrahydro-6H,12H, 13H-(5-bromo)indeno[2,3a]pyrrolo[3,4-c]carbazole-5,7-(5H,7H)-dione and 4c,7a,7b,12a-tetrahydro-6H,12H,13H-(6-bromo)indeno[2,3-a]pyrrolo[3,4-c]carbazole-5,7-(5H, 7H)-dione A mixture containing 2-(2-(5-bromoindenyl)indole and 2-(2-(6-bromoindenyl)indole (260 mg, 0.84 mmol) and maleimide (125 mg, 1.3 mmol) in a 10 cm sealed reaction vial was heated at 180°–190° C. for 1 hour. After the mixture was cooled to ambient temperature, MeOH (4 mL) was added. The solution was cooled to –20° C. and the product was collected as a white solid product.

Step-4A: Preparation of 9-Bromo-6H,12H,13H-indeno[2,3-a]pyrrolo[3,4-c]carbazole-5,7(5H,7H)-dione (Compound Ib-2) and 10-bromo-6H,12H,13H-indeno[2,3-a]pyrrolo[3,4-c]carbazole-5,7(5H,7H)-dione (Compound Ia-3)

Solid 2,3-dichloro-5,6-dicyano-1,4-benzoquinone (335 mg, 1.5 mmol) was added in one portion to a solution of the mixture containing 4c,7a,7b,12a-tetrahydro-6H,12H,13H-5-bromoindeno[2,3-a]pyrrolo[3,4-c]carbazole-5,7-(5H,7H)-dione and 4c,7a,7b,12a-tetrahydro-6H,12H,13H-6-bromoindeno[2,3-a]pyrrolo[3,4-(5H,7H)-dione (240 mg, 0.59 mmol) in toluene (20 mL). The mixture was stirred at 60°–65° C. for 4 hours. The solution was cooled in an ice bath and the precipitate collected by filtration. The product was resuspended and triturated with MeOH (10 mL). The product was collected and purified by column chromatography (silica gel, EtOAc:Hexane 1:1).

Compound Ia-3: Rf0.45 (10-bromo isomer). The melting point was greater than 300° C. $^1$H NMR (DMSO-d$_6$, 300 MHz): δ4.3 (s, 2H), 7.3 (m, 1H), 7.5–7.75 (m, 3H), 8.0 (s, 1. for C$_{21}$H$_{11}$BrN$_2$O$_2$0.4 H$_2$O : C, 61.45; H, 2.90; N, 6.82. Found C, 61.39; H, 2.67; N, 6.66.

Compound Ib-2: Rf0.4 (9-bromo isomer) mp>300° C. $^1$H NMR (DMSO-d$_6$, 300 MHz): δ4.3 (s, 2H), 7.35 (m, 1H), 7.55–7.75 (m, 4H), 8.95 (d, 1H), 9.3 (s, 1H), 11.3 (s, 1H); 12.35 (s, 1H). MS(FAB): m/e 404 (m+1)$^+$. Anal. calc. for C$_{21}$H$_{11}$BrN$_2$O$_2$: C, 62.55; H, 2.75; N, 6.95. Found C, 62.23; H, 2.71; N 6.66.

EXAMPLE V(E)(5)

Preparation of 3-Iodo-5H,6H,12H,13H-indeno[2,3-a] pyrrolo[3,4-c]carbazole-7(7H)one (Compound I-40)

Step-1: Preparation of 3-Tributylstannyl-5H,6H,12H,13H-indeno[2,3-a]pyrrolo[3,4-c]carbazole-7(7H) one To a solution of 3-bromo-5H,6H,12H,13H-indeno[2,3-a] pyrrolo[3,4-c]carbazole-7(7H)one (Compound I-9) (50 mg, 0.13 mmol), bis(tributyltin) (0.065 ml, 0.13 mmol) and triethylamine (1.0 mL) in DMF (11 mL) was added tetrakis (triphenylphosphine)palladium(0) (32 mg). The solution was heated in a sealed reaction tube at 120° C. for 18 h. The mixture was cooled to ambient temperature and solvent concentrated at reduced pressure. The product was purified by column c H), 8.9–9.05 (dd, 2H), 11.25 (s, 1H); 12.35 (s, 1H). MS(FAB): m/e 404 (m+1)$^+$. Anal. calc chromatography (silica gel, EtOAc:MeOH; 1:2, Rf=0.64) to give 17 mg (20%). The compound was further purified by preparative TLC (silica gel, EtOAc:hexane; 3:1) to give the subject compound as a tan solid, mp>300° C. $^1$H NMR (DMSO-d$_6$, 300 MHz): d 0.88 (t, 3H), 1.13 (q, 2H), 1.33 (q, 2H), 1.58 (q, 2H), 4.17 (s, 2H), 4.92 (s, 2H), 7.33–7.54 (m, 4H), 7.63–7.71 (m, 3H), 8.0 (s, 1H), 8.54 (s, 1H), 9.42 (d, 1H), 11.92 (s, 1H); MS (m/e)=600 (m+1)$^+$.

Step-2: Preparation of Compound I-40

To a solution of 3-tributylstannyl-5H,6H,12H,13H-indeno[2,3-a]pyrrolo[3,4-c]carbazole-7(7H)one (Step-1) (16 mg, 0.026 mmol) in dry CH$_2$Cl$_2$ (4 mL) was added a solution of I$_2$(8 mg, 2 mL CH$_2$Cl$_2$) dropwise. The mixture was stirred at ambient temperature 2 h., then a solution of 10% NaHSO$_3$ was added. After stirring for 10 min. the mixture was filtered. The solid was collected and washed with water, CH$_2$Cl$_2$ and dried under vacuum (100° C., 6 h) to give 6 mg (53%) of Compound I-40. $^1$H NMR (DMSO-d$_6$, 300 MHz) d 4.29 (s, 2H), 4.96 (s, 2H), 7.33–7.50 (m, 3H), 7.66–7.79 (m, 2H), 8.29 (s, 1H), 8.62 (s, 1H), 8.42 (d, 1H), 12.08 (s, 1H). MS (m/e)=437 (m+1)$^+$.

EXAMPLE V(E)(6)

Preparation of 3-(2-Iodoethenyl)-5H,6H,12H,13H-indeno [2,3-a]pyrrolo[3,4-c]carbazole-7(7H)-one (Compound I-44)

Step-1: Preparation of 3-(2-Trimethylsilylethenyl-5H,6H, 12H,13H-indeno[2,3-a]pyrrolo[3,4-c]carbazole-7(7H)one To a solution of 3-bromo-5H,6H,12H,13H-indeno[2,3-a] pyrrolo[3,4-c]carbazole-7(7H)one (Compound I-9) (400 mg, 1.0 mmol), 2-(trimethylsilylvinyl)tributylstannae (500 mg, 1.3 mmol) and zinc chloride (170 mg, 1.3 mmol) in DMF (5 mL) was added bis(triphenylphosphine)palladium (II)chloride (7 mg). The solution was heated in a sealed reaction tube at 100° C. for 36 h. The mixture was cooled to ambient temperature and solvent concentrated at reduced pressure. The residue was triturated with hexane to give 470 (89%) mg of tan solid. The product was chromatographed (neutral alumina, THF:hexane; 1:1 to THF: hexane 2:1, Rf=0.45), and the subject compound crystallized in the collected fractions, mp>300° C. $^1$H NMR (DMSO-d$_6$, 300 MHz) d 0.2 (s, 9H), 4.17 (s, 2H), 4.94 (s, 2H), 6.55 (d, 1H, J=19.1 Hz), 7.12 (d, 1H, J=19.2 Hz), 7.33–7.45 (m, 4H), 7.56–7.59 (m, 1H), 7.68 (d, 1H, J=7 Hz), 8.09 (s, 1H), 8.62 (s, 1H), 9.40 (d, 1H, J=7.6 Hz), 12.01 (s, 1H); MS (m/e)=431 (m+1)$^+$.

Step-2

To a slurry of 3-(2-trimethylsilylethenyl-5H,6H,12H, 13H-indeno[2,3-a]pyrrolo[3,4-c]carbazole-7(7H)one (Step-1) (50 mg, 0.12 mmol) in CH$_2$Cl$_2$(3 mL) was added a solution of iodide (19 mg) in CH$_2$Cl$_2$ dropwise. The mixture was stirred 4 h at ambient temperature, then concentrated at reduced pressure. To the residue was added a solution of 10% NaHSO$_3$ (2 mL), and the solution was stirred 20 h. A yellow solid was collected and dried to give 35 mg. A THF extract of the solid after evaporation and trituration with MeOH gave 10 mg of Compound I-44 as a yellow solid, mp>300° C. $^1$H NMR (DMSO-d$_6$, 300 MHz) d 4.17 (s, 2H), 4.96 (s, 2H), 7.22–7.70 (m, 7H), (m, 1H), 8.10 (s, 1H), 8.63 (s, 1H), 9.40 (d, 1H, J=7.6 Hz), 12.04 (s, 1H); MS (m/e)=463 (m+1)$^+$.

F. Specific Description of Synthetic Processes
Preparation of Methylated Fused Pyrrolocarbazoles Part IVA. Methylated Derivatives

EXAMPLE V(F)(1)

Step-1A: Preparation of 2-(2-(2-Hydroxy)indanyl)-7-methylindole

This compound was prepared by substantially the same procedure as Part IA, Step-1A except that 7-methylindole was substituted for I.

2-(2-(2-Hydroxy)indanyl)-7-methylindole: yield 11%; mp 199°–200° C. The following NMR data were obtained: $^1$H NMR (CDCl$_3$, 300 MHz): δ2.3 (s, 1H), 2.55 (s, 3H), 3.4 (d, 2H), 3.6 (d, 2H), 6.4 (s, 1H), 7.0 (m, 2H), 7.2–7.35 (m, 4H), 7.45 (d, 1H), 8.5 (s, 1H).

Step-2A: Preparation of 2-(2-Indenyl)-7-methylindole

This compound was prepared by substantially the same procedure as Part IA, Step-2A.

2-(2-Indenyl)-7-methylindole; yield 92%, mp 204°–206° C. The following NMR data were obtained: $^1$H NMR (CDCl$_3$, 300 MHz): δ2.6 (s, 3H), 3.85 (s, 2H), 6.7 (s, 1H), 7.0–7.5 (m, 8H), 8.2 (s, 1H).

Step-3A: Preparation of 1-Methyl-12H,13H-indeno[2,3-a]pyrrolo[3,4-c]carbazole-6H-5,7(5H,7H)-dione (Compound Ib-1)

A mixture of 2-(2-indenyl)-7-methylindole (100 mg, 0.41 mmol) and maleimide (80 mg, 0.82 mmol) in a 10 cm sealed reaction vial was heated at 180°–185° C. for 30 min. After cooling to ambient temperature, the product was dissolved in CH$_3$OH (5 mL) and precipitated by slow addition of ether-hexane (1:2) to yield a yellow amorphous solid. This solid, 1-methyl-4c,7a,7b,12a-tetrahydro-6H,12H,13H-indeno[1,2-a]pyrrolo[3,4-c]carbazole-5,7(5H,7H)-dione, in toluene (20 mL) was added to solid 2,3-dichloro-5,6-dicyano-1,4-benzoquinone (235 mg, 1.03 mmol) in one portion. The mixture was heated at 60°–65° C. for 6 hours. After cooling to ambient temperature, the solid precipitate was collected. The product was suspended and triturated in cold MeOH and the precipitate collected by filtration. The precipitate was washed with cold MeOH, and recrystallized from THF-MeOH-Et$_2$O to yield Compound Ib-1 as an orange powder. The yield was 35 mg (25% yield). The mp was greater than 320° C. The following NMR data were obtained: $^1$H NMR (DMSO-d$_6$, 300 MHz): δ2.65 (s, 3H), 4.35 (s, 2H), 7.2 (t, 2H), 7.35 (d, 1H), 7.4–7.55 (m, 2H), 7.8 (d, 1H), 8.8 (d, 1H), 9.15 (d, 1H), 11.2 (s, 1H), 12.35 (s, 1H). MS(FAB): m/e 339 (m+1)$^+$.

EXAMPLES V(F)(2) and (3)

Step-1A: Preparation of 2-(2-(2-Hydroxy)indanyl)-1-methylindole n-BuLi (6.1 mL of 2.5M solution in hexanes, 15.2 mmol) was added dropwise over a 10 min period to a solution of freshly distilled 1-methylindole (2.0 g, 15.2 mmol) in dry ether (15 mL) under a nitrogen atmosphere. The solution was stirred at reflux 6 hours. After cooling to ambient temperature, 2-indanone (2.2 g, 16.8 mmol) in ether (15 mL) was added dropwise. The mixture was stirred at reflux for 30 min, poured into 2N HCl (50 mL) and extracted with CH$_2$Cl$_2$ (2×50 mL). The combined CH$_2$Cl$_2$ layers were washed with H$_2$O (2×50 mL), saturated NaCl solution (2×50 mL) and dried (MgSO$_4$). The product was purified by column chromatography (silica gel, CH$_2$Cl$_2$) to give 500 mg (13% yield) with an mp of 160°–161° C. The following NMR data were obtained: $^1$H NMR (CDCl$_3$, 300 MHz): δ2.2 (s, 1H), 3.5 (d, 2H), 3.65 (d, 2H), 4.0 (s, 3H), 7.0–7.6 (m, 9H).

Step-2A: Preparation of 2-(2-Indenyl)-1-methylindole

This compound was prepared by substantially the same procedure as Part IA, Step-2A.

2-(2-Indenyl)-1-methylindole; yield 95%; mp 146°–148° C. The following NMR data were obtained: $^1$H NMR (CDCl$_3$, 300 MHz): δ4.0 (s, 2H), 4.1 (s, 3H), 7.1–7.7 (m, 10H). MS(FAB): m/e 245 (m$^+$).

Step-3A: Preparation of 13-Methyl-4c,7a,7b,12a-tetrahydro-6H,12H-indeno[2,3-a]pyrrolo[3,4-c]carbazole-5,7(5H,7H)-dione.

A mixture of 2-(2-indenyl)-1-methylindole (300 mg, 1.4 mmol) and maleimide (200 mg, 2.1 mmol) in a 10 cm sealed reaction vial was heated at 180°–190° C. for 30 min. After cooling to ambient temperature, MeOH (5 mL) was added and the crystals which formed were collected by filtration and washed with cold MeOH to give 335 mg (70% yield) of a light yellow solid product. The melting point was greater than 220° C. acetone-MeOH. The following NMR data were obtained: $^1$H NMR (CDCl$_3$, 300 MHz): δ2.9 (m, 1H), 3.4–3.55 (m, 2H), 3.65–3.95 (m, 5H), 4.5 (d, 2H), 7.1–7.5 (m, 7H), 8.1 (d, 1H). MS(FAB): m/e 342(m$^+$).

EXAMPLE V(F)(4)

Step-4A: Preparation of 13-Methyl-6H,12H-indeno[2,3-a]pyrrolo[3,4-c]carbazole-5,7(5H,7H)-dione (Compound I-4)

Solid 2,3-dichloro-5,6-dicyano-1,4-benzoquinone (500 mg, 2.2 mmol) was added in one portion to a solution of 13-methyl-4c,7a,7b,12a-tetrahydro-6H,12H-indeno[2,3-a]pyrrolo[3,4-c]carbazole-5,7(5H,7H)-dione (300 mg, 0.9 mmol) in toluene (25 mL). The mixture was stirred at 60°–65° C. for 4 hours. After cooling in an ice-bath, the precipitate was collected by filtration. The solid was suspended in MeOH, recollected and washed with cold MeOH (5 mL). The product was recrystallized from THF-MeOH to give 260 mg (88% yield) of Compound I-4 as a yellowish powder. Compound I-4 has an mp of greater than 220° C. The following NMR data were obtained: $^1$H NMR (DMSO-d$_6$, 300 MHz): δ4.2 (s, 3H), 4.6 (s, 2H), 7.3 (t, 1H), 7.4–7.55 (m, 2H), 7.6 (t, 1H), 7.75 (m,2H), 9.0 (d, 1H), 9.15 (d, 1H), 11.2 (s, 1H). MS(FAB); m/e 338 (m$^+$).

EXAMPLE V(F)(5) (Method A)

Preparation of a mixture of 13-Methyl-6H,7H,12H-indeno[2,3-a]pyrrolo[3,4-c]carbazole-5(5H)one and 13-methyl-5H,6H,12H-indeno[2,3-a]pyrrolo[3,4-c]carbazole-7(7H) one (Compound I-5)

To a stirred suspension of Zn dust (800 mg) and mercuric chloride (100 mg) in water (5 mL) was added 0.5 mL of concentrated hydrochloric acid (dropwise). After 5 min, the aqueous layer was decanted. The zinc amalgam was first washed with water, then repeatedly washed with EtOH. The zinc amalgam was suspended in THF (40 mL), and solid Compound I-4 (Example V(A)(3)) (200 mg, 0.6 mmol) was added in one portion. HCl(g) was passed through while the solution was maintained at reflux for 1 hour. The reaction mixture was cooled on an ice bath, and a brown precipitate was collected by filtration and washed with MeOH (5 mL). Recrystallization from THF-ether gave 45 mg (23% yield) of the mixture as a tan powder product with amp of greater than 260° C. The following NMR data were obtained: $^1$H NMR (DMSO-d$_6$, 300 MHz): δ4.2 (s, 3H), 4.6 (s, 1.67H), 4.75 (s, 0.33H), 4.85 (s, 0.33H), 4.90 (s, 1.67H), 7.25–7.45 (m, 3H), 7.55 (t, 1H), 7.65 (d, 1H), 7.75 (d, 1H), 8.0 (d, 1H), 8.55 (s, 0.83H), 8.8 (0.17H), 9.3 (d, 0.17H), 9.5 (d, 0.83H). MS(FAB): m/e 325 (m+1)$^+$.

G. Specific Description of Synthetic Processes
Preparation of Methoxylated Fused Pyrrolocarbazoles Part VA: Methoxylated Derivatives

EXAMPLE V(G)(1)

Preparation of 5-Methoxy-2-(2-(2-hydroxy)indanyl)indole
Step-1A

This compound was prepared by substantially the same procedure as Part IA, Step-1A except that 5-methoxyindole was substituted for I.

5-Methoxy-2-(2-(2-hydroxy)indanyl)indole, yield 2.9 g (59%) mp 139°–142° C. (ether-hexane). The following NMR data were obtained: $^1$H NMR (CDCl$_3$) δ2.3 (bs, 1H), 3.3 (d, 2H), 3.55 (d, 2H), 3.9 (s, 3H), 6.35 (s, 1H), 6.8 (d, 1H), 7.05 (s, 1H), 7.2–7.4 (m, 5H), 8.45 (bs, 1H).

Step-2A: Preparation of 5-Methoxy-2-(2-indenyl)indole

This compound was prepared by substantially the same procedure as Part IA, Step-2A.

5-Methoxy-2-(2-indenyl)indole; yield (59%) mp 208°–210° C. (ether-hexane) $^1$H NMR (CDCl$_3$) δ3.9 (s, 5H), 6.6 (s, 1H), 6.85 (d, 1H), 7.05 (d, 2H), 7.15–7.3 (m, 3H), 7.4 (d, 1H), 7.45 (d, 1H), 8.15 (bs, 1H).

Step-3A: Preparation of 6-Methoxy-4-cyano-3-ethoxycarbonyl-1,2,3,4-tetrahydro-[1H]indeno[2,3-a]9H-carbazole A mixture of 5-methoxy-2-(2-indenyl)indole (500 mg, 1.9 mmol) and ethyl cis-b-cyanoacrylate (5.0 g, 40 mmol), in a sealed reaction flask, was heated at 180° C. with stirring for 1.5 hours. The mixture was cooled to ambient temperature, MeOH (10 mL) was added and the solution was cooled to −20° C. The product was collected to give 175 mg (24%) of a light tan solid product, mp 278°–282° C. The following NMR data were obtained: $^1$H NMR (DMSO-d$_6$, 300 MHz): δ1.25 (t, 3H), 3.1–3.35 (m, 3H), 3.8 (s,m, 4H), 3.9 (m, 1H), 4.3–4.55 (m, 2H), 4.6 (d, 1H), 6.7 (d, 1H), 6.95 (s, 1H), 7.05–7.25 (m, 5H), 11.1 (s, 1H). IR (KBr) cm$^{-1}$: 2210 (CN); 1690 (C=O).

Step-4A: Preparation of 6-Methoxy-4-cyano-3-ethoxycarbonyl-1,2,3,4-tetrahydro-[1H]-indeno[2,3-a]9H-carbazole 2,3-dichloro-5,6-dicyano-1,4-benzoquinone (185 mg, 0.81 mmol) was added in one portion to a stirred solution of 6-methoxy-4-cyano-3-ethoxycarbonyl-1,2,3,4-tetrahydro-[1H]-indeno[2,3-a]9H-carbazole (125 mg, 0.32 mmol) in dry toluene (20 mL). The solution was stirred at 60°–65° C. for 6 hours. After cooling on an ice bath the precipitate was collected by filtration, the product was suspended in MeOH (20 mL), collected and washed with cold MeOH (10 mL). The filtrate was recrystallized from acetone to yield 110 mg (90%) of a light tan product. The melting point was greater than 250° C. The following NMR data were obtained: $^1$H NMR (DMSO-d$_6$, 300 MHz): δ1.4 (t, 3H), 3.9 (s, 3H), 4.25 (s, 2H), 4.6 (q, 2H), 7.25 (d, 1H), 7.4 (m, 2), 7.62 (m, 1H), 7.75 (m, 1H), 7.95 (d, 1H), 12.5 (s, 1H). IR(KBr) cm$^{-1}$: 2210 (CN); 1710 (C=O). MS(FAB): m/e 370 (m$^+$).

Step-5A: Preparation of 3-Methoxy-5H,6H,12H,13H-Indeno[2,3-a]pyrrolo[3,4-c]carbazole-7(7H)one (Compound I-13)

A mixture of 6-methoxy-4-cyano-3-ethoxycarbonyl-1,2,3,4-tetrahydro-[1H]indeno[2,3-a]9H-carbazole (80 mg, 0.21 mmol) and Raney Nickel catalyst (approx. 500 mg, wet form) in THF (50 mL) was hydrogenated at 35 psi on a Parr Apparatus for 12 hours. THF (50 mL), was added and then the solvent was filtered through Celite® and concentrated at reduced pressure. The product was purified by column chromatography (silica gel, EtOAc:hexane, 2:1, R$_f$=0.3) to yield 76 mg (94%) of Compound I-13 as an off white solid product. The melting point was greater than 300° C. The following NMR data were obtained: $^1$H NMR (DMSO-d$_6$, 300 MHz): δ3.9 (s, 3H), 4.15 (s, 2H), 4.95 (s, 2H), 7.1 (d, 1H), 7.3–7.8 (m, 5H), 8.57 (s, 1H), 9.4 (d, 1H); 11.75 (s, 1H). MS(FAB): m/e 341 (m+1)$^+$. Anal. calc. for: C$_{22}$H$_{16}$N$_2$O$_2$, 0.75 H$_2$O ; C, 74.66; H, 4.99; N7.92. Found: C, 74.46; H, 4.65; N, 7.79.

H. Specific Description of Synthetic Processes
Preparation of Fused Pyrrolocarbazoles Having Expanded E Ring Derivatives Part VIA: Expanded E Ring Derivatives

EXAMPLE V(H)(1)

Step-1A: Preparation of 2-(2-(2-Hydroxy)-1,2,3,4-tetrahydronaphthyl)indole (FIG. 2, V, R$^2$,R$^3$=H, X=CH$_2$CH$_2$ n-BuLi (85.3 mmol, 34 mL of 2.5M sol. in hexanes) was added dropwise to a solution of indole (10.0 g, 85.3 mmol) in dry THF (500 mL) at −78° C. (nitrogen atmosphere) over a 15 min period. The solution was stirred for 30 min, followed by the addition (by bubbling) of CO$_2$(g) for 10 min. The solution was allowed to warm to ambient temperature, then concentrated to approximately 300 mL at reduced pressure. THF (200 mL) was added and the solution was recooled to −78° C. A solution of t-BuLi (85.3 mmol, 50 mL of 1.7M solution in hexanes) was then added dropwise. The resulting yellow solution was allowed to stir for 2 hours at −78° C. Instead of 2-indanone, 2-tetralone (13.7 g, 12.9 mL, 93.7 mmol) was added dropwise and the mixture was stirred for 1 hour. The reaction was quenched by addition of water (5 mL). The reaction was poured into a saturated NH$_4$Cl solution (250 mL), and extracted with ether (2×200 mL). The Et$_2$O layer was washed with 100 mL of a saturated NH$_4$Cl solution, followed by drying (MgSO$_4$), and concentration to give an oil. The product was recrystallized from MeOH to give 10 g (45%) of a white solid product, (top 191°–192° C.). The following NMR data was obtained: $^1$H NMR (CDCl$_3$): d 2.1–2.2 (b, 2H), 2.5–2.65 (m, 1H), 2.9–3.1 (m, 2H), 3.35 (m, 1H), 5.35 (s, 1H), 6.2 (s, 1H), 6.2–7.1 (m, 6H), 7.35 (d, 1H), 7.4 (d, 1H), 11.5 (s, 1H). Anal. calc. for C$_{18}$H$_{17}$NO: C, 82.10; H, 6.51; N, 5.32. Found C, 82.07; H, 6.47; N, 5.18.

Step-2A: Preparation of 2-(2-(3,4-dihydro)naphthyl)indole

To a stirred solution of 2-(2-(2-Hydroxy)-1,2,3,4-(tetrahydronaphthyl)indole (step-1)(5.0 g, 19.0 mmol) in acetone (150 mL) was added 2N HCl (5 mL) at ambient temperature. The solution was stirred for 1 hour, then water (approximately 25 mL) was added. The precipitate was collected by filtration, washed well with water and dried to give 4.5 g (97%) of purified product. A sample was recrystallized from MeOH to give product which exhibited mp of 179°–180° C. The following NMR data were obtained: $^1$H NMR (CDCl$_3$): δ2.7 (m, 2H); 2.9 (m, 2H), 6.65 (s, 1H), 6.98 (t, 1H), 7.05–7.15 (m, 6H), 7.35 (d, 1H), 7.5 (d, 1H), 11.35 (bs, 1H). Anal. calc. for C$_{18}$H$_{15}$N: C, 88.13; H, 6.16; N, 5.71. Found, C, 88.24; H, 6.14; N, 5.61.

Step-3A: Preparation of 4c,7a,7b,12,13,13a-Hexahydro-6H,14H-naphthyl[3,4-a]pyrrolo[3,4-c]carbazole-5,7-(5H,7H)dione (FIG. 4, XVIII, A1, A2; B1, B2═O)

A stirred mixture of 2-(2-(3,4-dihydronaphthyl)indole (500 mg, 2.0 mmol) and maleimide (300 mg, 3.1 mmol) in a sealed reaction vial was heated at 180°–190° C. for 30 min. After cooling to ambient temperature, MeOH (5 mL) was added, the product was collected and recrystallized from MeOH to give 610 mg (89%) of a white solid product, mp 256°–258° C. The following NMR data were obtained: $^1$H NMR (DMSO-d$_6$, 300 MHz): δ1.6–1.75 (m, 1H) 2.15 (d, 1H), 2.9–3.0 (m, 2H), 3.15–3.25 (m, 1H), 3.45 (t, 1H), 3.95 (m, 1H), 4.3 (d, 1H), 7.0–7.4 (m, 7H), 7.8 (d, 1H), 10.8 (s, 1H), 11.15 (s, 1H).

Step-4: Preparation of 12,13-Dihydro-6H,14H-naphthyl[3,4-a]pyrrolo[3,4-c]carbazole-5,7(5H,7H)dione (Compound I-14)

Solid 2,3-dichloro-5,6-dicyano-1,4-benzoquinone (930 mg, 4.1 mmol) was added in one portion to a solution of 4c,7a,7b,12,13,13a-hexahydro-6H,14H-napthyl[3,4-a]pyrrolo[3,4-c]carbazole-5,7-(5H,7H)dione (400 mg, 1.2 mmol) in toluene (50 mL). The solution was maintained at 60°–65° C. for six hours. After cooling on an ice bath, the solid was collected by filtration, suspended in MeOH (20 mL) and the product collected by filtration to give 320 mg (79%) of Compound I-14 as an orange solid. The melting point was 258°–260° C. The following NMR data were obtained: $^1$H NMR (DMSO-d$_6$, 300 MHz): δ2.9 (m, 2H), 3.1 (m, 2H), 7.3–7.4 (m, 4H), 7.5–7.65 (m, 2H), 8.15 (d, 1H), 8.95 (d, 1H), 11.1 (s, 1H), 12.0 (s, 1H). MS(FAB): m/e 338 (m$^+$). Anal. calc. for C$_{22}$H$_{14}$N$_2$O$_2$: C, 78.09; H, 4.17; N, 8.28. Found; C, 77.67; H, 3.96; N, 8.16.

EXAMPLE V(H)(2)

Preparation of 6H,14H-naphthyl[3,4-a]pyrrolo[3,4-c]carbazole-5,7(5H,7H)-dione (Compound I-15)

Solid 2,3-dichloro-5,6-dicyano-1,4-benzoquinone (465 mg, 2.1 mmol) was added in one portion to a solution of 4c,7a,7b,12,13,13a-hexahydro-6H,14H-naphthyl[3,4-a]pyrrolo[3,4-c]carbazole-5,7-(5H,7H)dione (200 mg, 0.59 mmol) in dry dioxane (30 mL). The solution was stirred at reflux for 12 hours. The mixture was cooled to ambient temperature, the precipitate was removed by filtration, and the solvent concentrated at reduced pressure. The residue was heated to reflux in MeOH (25 mL), cooled to ambient temperature, recrystallized from THF-MeOH and the product collected to yield 120 mg (61%) of Compound I-15 as a brown solid. The melting point was greater than 330° C. The following NMR data were obtained: $^1$H NMR (DMSO-d$_6$, 300 MHz): δ 7.4 (t, 1H), 7.6 (t, 1H); 7.7–7.8 (m, 3H), 8.1 (m, 1H), 8.2 (d, 1H), 8.6 (d, 1H), 9.1 (d, 1H), 10.0 (m, 1H), 11.2 (s, 1H), 12.9 (s, 1H). MS(FAB): m/e 336 (m$^+$). Anal. calc. for C$_{22}$H$_{12}$N$_2$O$_2$: C, 78.56; H, 3.60; N, 8.33. Found; C, 78.03; H, 3.30; N, 8.12.

EXAMPLE V(H)(3)

Step-1B: Preparation of 3-Cyano-4-ethoxycarbonyl-1,2,3,4-tetrahydro-1,2-di-hydronaphthyl[3,4-a]9H-carbazole and 4-cyano-3-ethoxycarbonyl-1,2,3,4-tetrahydro-1,2-di-dronaphthyl[3,4-a]9H-carbazole A mixture of 2-(2-(3,4-dihydro)naphthyl)indole (FIG. 2, R$^2$R$^3$, R$^4$, R$^5$R$^6$═H, X═CH$_2$CH$_2$ 1.0 g, 4.1 mmol) and ethyl cis-β-cyanoacrylate (5.0 g, 40 mmol) was heated in a sealed reaction flask at 180° C. with stirring for 1 hour. The mixture was cooled to ambient temperature and the excess cyanoacrylate was removed by Kugelrohr distillation (oven temperature 80°–85° C., 0.5 mm). MeOH (25 mL) was added to the residue and the product triturated to give 700 mg (46%) of a white solid. The $^1$H NMR data showed approximately a 2:1 mixture of each of the 4-CN:3-CN isomers. The following NMR data were obtained: $^1$H NMR (DMSO-d$_6$, 300 MHz): δ1.25 (t, 3H), 3.1–3.35 (m, 3H), 3.8 (s,m, 4H), 3.9 (m, 1H), 4.3–4.55 (m, 2H), 4.6 (d, 1H), 6.7 (d, 1H), 6.95 (s, 1H), 7.05–7.25 (m, 5H), 11.1 (s, 1H).

Step-2B: Preparation of 3-Cyano-4-ethoxycarbonyl-1,2-di-hydronaphthyl[3,4-a]9H-carbazole and 4-cyano-3-ethoxycarbonyl-1,2-di-hydronaphthyl[3,4-a]9H-carbazole 2,3-dichloro-5,6-dicyano-1,4-benzoquinone (900 mg, 4.0 mmol) was added in one portion to a stirred solution of the product from the preceding step (590 mg, 1.6 mmol) in dry toluene (50 mL). The solution was stirred at 65°–70° C. for 6 hours. The mixture was cooled to ambient temperature and the precipitate removed by filtration, and washed with toluene (10 mL). The toluene solution was concentrated at reduced pressure to yield a crude solid. Purification by column chromatography (silica gel, EtOAc:Hexane 2:1) gave 510 mg (87%) of an off-white solid product. The following NMR data were obtained: $^1$H NMR (DMSO-d$_6$, 300 MHz): δ1.15 and 1.4 (t, 3H), 2.9 and 3.1–3.2 (q, 2H), 4.35 and 4.6 (q, 2H), 7.2–7.7 (m, 4H), 7.9 (d, 0.5H), 8.2 (d, 0.5H), 8.4 (d, 1H), 12.2 (d, 1H)

Step-3B: Preparation of 12,13-dihydro-6H,7H,14H-naphthyl[3,4-a]pyrrolo[3,4-c]carbazole-5(5H)one (Compound I-16) and 12,13-Dihydro-5H,6H,14H-naphthy[3,4-a]pyrrolo[3,4-c]carbazole-7(7H)one (Compound I-17)

The isomeric mixture from the preceding step (300 mg; 0.81 mmol) was added to Raney Nickel catalyst (approximately 1 g, wet form) in MeOH (75 mL)/THF (25 mL) and was hydrogenated at 35 psi on a Parr Apparatus for 12 hours. The solution was diluted with THF (50 mL), then filtered through Celite®. The solvent was concentrated at reduced pressure to give 210 mg (80%) of crude product. The product was purified by column chromatography (silica gel; EtOAc:Hex; 2:1, R$_f$ 5-oxo=0.3 R$_f$ 7-oxo=0.25). The fractions containing product were collected and concentrated to give a white solid. A sample was recrystallized from MeOH-ether and dried (100° C., 0.5 mm, 12 hours) in order to obtain the following information:

Compound I-16: 5-oxo isomer mp>300° C. $^1$H NMR (DMSO-d$_6$, 300 MHz) δ2.9 (m, 2H), 3.1 (m, 2H), 4.95 (s, 2H), 7.1 (t, 1H), 7.3–7.48 (m, 4H), 7.55 (d, 1H), 8.75 (s, 1H), 9.15 (d, 1H), 11.6 (s, 1H). MS(FAB): m/e=325 (M+1)$^+$. Anal. calc. C$_{22}$H$_{16}$N$_2$O.0.1 H$_2$O ; C, 81.01; H, 5.01; N, 8.59. Found: C, 80.83; H, 5.04; N, 8.46.

Compound I-17: 7-oxo isomer mp>300° C. $^1$H NMR (DMSO-d$_6$, 300 MHz) δ2.9 (m, H), 3.1 (m, 2H), 4.9 (s, 2H), 7.2–7.35 (t, 4H), 7.5 (t, 1H), 7.6 (d, 1H), 8.2 (m, 1H), 8.4 (s, 1H), 11.7 (s, 1H). MS(FAB): m/e=325 (M+1)$^+$. Anal. calc. for: C$_{22}$H$_{16}$N$_2$O.0.25 H$_2$O ; C, 80.34; H, 5.06; N, 8.52. Found: C, 80.16; H, 5.08; N, 8.23.

EXAMPLE V(H)(4)

Preparation of 3-Bromo-12,13-dihydro-6H,7H,14H-naphthyl[3,4-a]pyrrolo[3,4-c]carbazole-5(5H)one (Compound I-18)

Solid N-bromosuccinimide (14 mg, 0.1 mmol) was added to a stirred solution of Compound I-16 (25 mg, 0.08 mmol) in dry THF (5 mL) under a nitrogen atmosphere. The solution was stirred at ambient temperature for 12 hours, then concentrated at reduced pressure. Recrystallization from MeOH gave 25 mg (81%) of Compound I-18 as a white solid. The melting point was greater than 300° C. (THF-MeOH). The following NMR data were obtained: $^1$H NMR (DMSO-d$_6$, 300 MHz): δ2.9 (m, 2H), 3.2 (m, 2H), 4.9 (s, 2H), 7.3–7.45 (m, 3H), 7.5–7.6 (m, 2H), 7.82 (d, 1H, 8.92 (s, 1H), 9.35 (s, 1H), 11.8 (s, 1H). MS(FAB): m/e 403 (m$^+$).

EXAMPLE V(H)(5)

Preparation of 3-Bromo-12,13-Dihydro-5H,6H,14H-naphthyl[3,4-a]pyrrolo[3,4-c]carbazole-7(7H)one (Compound I-19)

To a stirred solution of Compound I-17, (25 mg, 0.08 mmol) in dry THF (7 mL) under a nitrogen atmosphere was added solid N-bromosuccinimide (14 mg, 0.1 mmol). The solution was stirred at ambient temperature for 12 hours, then concentrated at reduced pressure. The product was recrystallized from MeOH-ether to yield 22 mg (71% yield) of Compound I-19 as a white solid. The melting point was greater than 300° C. (THF-MeOH). The following NMR data were obtained: $^1$H NMR (DMSO-d$_6$, 300 MHz): δ2.9 (m, 2H), 3.05 (m, 2H), 4.95 (s, 2H), 7.3–7.35 (m, 3H), 7.55–7.65 (m, 2H), 8.15 (s, 1H), 8.2 (m, 1H, 8.48 (s, 1H, 11.9 (s, 1H. MS(FAB): m/e 403 (m$^+$).

EXAMPLE V(H)(6)

Step-1: Preparation of 5-fluoro-2-(2-(2-hydroxy)-1,2,3,4-tetrahydronaphthyl)indole (FIG. 3, V, R$^2$=H, R$^3$=F on C5, X=CH$_2$CH$_2$)

Preparation of this compound used substantially the same procedure as Example V(H)(1), Step-1A, except that 5-fluoroindole (3.35 g, 24.8 mmol) and 2-tetralone (4.0 g, 27.3 mmol) were used to give 5-fluoro-2-(2-(2-hydroxy)-1, 2,3,4-tetrahydronaphthyl)indole; yield 1.8 g (26%), mp 158°–159° C. dec (ether-hexane). The following NMR data were obtained: $^1$H NMR (CDCl$_3$, 300 MHz): d 2.1 (s, 1H), 2.25 (t, 2H), 2.8–2.9 (m, 1H), 3.05–3.2 (m, 2H), 3.45 (d, 1H), 6.23 (s, 1H), 6.9 (t, 1H), 7.1–7.3 (m, 6H), 8.55 (bs, 1H).
Step-2: Preparation of 2-(2-(3,4-dihydro)naphthyl)-5-fluoroindole Substantially the same procedure as Example V(H)(1), Step-2A was employed using 5-fluoro-2-(2-(2-hydroxy)-1, 2,3,4-tetrahydronaphthyl)indole (1.0 g, 3.6 mmol); yield 900 mg (96%), mp 174°–176° C. dec (MeOH-ether). The following NMR data were obtained: $^1$H NMR (CDCl$_3$, 300 MHz): δ2.75–2.82 (m, 2H), 2.95–3.02 (m, 2H), 6.65 (s, 1H), 6.8 (s, 1H), 6.9–7.0 (m, 1H), 7.1–7.3 (m, H), 8.25 (bs, 1H).
Step-3: Preparation of 3-Cyano-4-ethoxycarbonyl-6-fluoro-1,2,3,4-tetrahydro-1,2-dihydronaphthyl[3,4-a]-9H-carbazole and 4-cyano-3-ethoxycarbonyl-6-fluoro-1,2,3,4-tetrahydro-1,2-dihydronaphthyl[3,4-a]9H-carbazole (FIG. 3, XII and XV, R$^2$, R$^3$, R$^5$, R$^6$=H, R$^4$=F) (X=CH$_2$CH$_2$)

A mixture of 2-(2-(3,4-dihydro)naphthyl)-5-fluoroindole (700 mg, 2.7 mmol) and ethyl cis-β-cyanoacrylate (3.3 g, 27 mmol) was heated in a sealed reaction flask at 180° C. with stirring for 1 hour. The mixture was cooled to ambient temperature and the excess cyanoacrylate was removed by Kugelrohr distillation (oven temperature 80°–85° C., 0.5 mm). MeOH (25 mL) was added to the residue and the 4-cyano product was separated to give 400 mg (39%) of a white solid, mp 256°–258° C. The following NMR data were obtained: $^1$H NMR (DMSO-d$_6$, 300 MHz): δ1.25 (t, 3H), 3.1–3.35 (m, 3H), 3.8 (s,m, 4H), 3.9 (m, 1H), 4.3–4.55 (m, 2H), 4.6 (d, 1H), 6.7 (d, 1H), 6.95 (s, 1H), 7.05–7.25 (m, 5H), 11.1 (s, 1H).

Step-4: Preparation of 3-Cyano-4-ethoxycarbonyl-6-fluoro-1,2-tetrahydronaphthyl[3,4-a]9H-carbazole 2,3-dichloro-5,6-dicyano-1,4-benzoquinone (475 mg, 2.1 mmol) was added in one portion to a stirred solution of 3-cyano-4-ethoxycarbonyl-6-fluoro-1,2,3,4-tetrahydro-1,2-dihydronaphthyl[3,4-a]9H-carbazole (325 mg, 0.84 mmol) in dry toluene (50 mL). The solution was stirred at 65°–70° C. for 6 hours. The mixture was cooled to ambient temperature, the precipitate removed by filtration, and washed with toluene (10 mL). The toluene solution was concentrated at reduced pressure to give a crude solid. Purification of the combined solid by column chromatography (silica gel, EtOAc:Hexane 2:1) gave 275 mg (85%) of a light yellow solid product, mp 258°–260° C. The following NMR data were obtained: $^1$H NMR (DMSO-d$_6$, 300 MHz): δ1.2 (t, 3H), 2.9–3.0 (q, 2H), 3.1–3.2 (m, 2H), 4.35 (q, 2H), 7.3–7.5 (m, 5H), 7.7 (m, 1H), 8.1 (m, 1H), 12.25 (s, 1H).
Step-5: Preparation of 12,13-Dihydro-3-fluoro-5H,6H,14H-naphthyl[3,4-a]pyrrolo[3,4-c]carbazole-7(7H)one (Compound I-22)

A solution of 3-cyano-4-ethoxycarbonyl-6-fluoro-1,2-tetrahydronaphthyl[3,4-a]9H-carbazole (140 mg; 0.37 mmol) and Raney Nickel catalyst (approximately 0.5 g, wet form) in MeOH (40 mL)/THF (20 mL) was hydrogenated at 35 psi on a Parr Apparatus for 12 hours. The solution was diluted with THF (50 mL), then filtered through Celite®. The solvent was concentrated at reduced pressure and the product was recrystallized to give 35 mg (28%) of a white solid (Compound I-22). The melting point was greater than 300° C. The following NMR data were obtained: $^1$H NMR (DMSO-d$_6$, 300 MHz) δ2.85 (m, 2H), 3.02 (m, 2H), 4.9 (s, 2H), 7.2–7.35 (m, 4H), 7.6 (m, 1H), 7.8 (d, 1H), 8.2 (m, 1H), 8.45 (m, 1H), 11.95 (bs, 1H). MS(FAB): m/e=343 (M+1)$^+$.

EXAMPLE V(H)(7)

Step-1: Preparation of 2(2-(2-Hydroxy-6-fluoro-1,2,3,4-tetrahydronaphthyl))indole This compound was prepared by substantially the same procedure as Example V(H)(1), step-1A, except that 6-fluoro-2-tetralone and indole were used to give 2-(2-(6-fluoro-2-hydroxy-1,2,3,4-tetrahydronaphthyl))indole; mp 187°–188° C. $^1$H NMR (CDCl$_3$, 300 MHz): d 2.05 (s, 1H), 2.25 (m, 2H), 2.75–2.9 (m, 1H), 3.0–3.15 (m, 2H), 3.4 (m, 2H), 6.25 (s, 1H), 7.0–7.2 (m, 3H), 7.25–7.35 (m, 2H), 7.4 (d, 1H), 7.55 (d, 1H), 8.55 (s, 1H). Anal. talc. for C$_{18}$H$_{16}$BrNO: C, 63.17; H, 4.71; N, 4.09; Br, 23.35. Found: C, 63.06; H, 4.71; N, 4.02; Br, 23.57.
Step-2: Preparation of 2-(2-(6-Fluoro-3,4-dihydronaphthyl) indole)

Substantially the same procedure as Example V(H)(1), step-2A, was employed using 2-(2-(2-hydroxy-6-fluoro-1,2, 3,4-tetrahydronaphthyl)indole) (Step-1) to give the subject compound, mp 228°–231° C. $^1$H NMR (CDCl$_3$, 300 MHz): d 2.8 (m, 2H), 2.95 (m, 2H), 6.70 (s, 1H), 6.75 (s, 1H), 7.0 (m, 2H), 7.1 (m, 1H, 7.2–7.4 (m, 4H), 7.4 (d, 1H, 7.6 (d, 1H, 8.3 (s, 1H). Anal. calc. for C$_{18}$H$_{14}$BrN: C, 66.58; H, 4.33; N, 4.22; F, 24.87. Found; C, 66.68; H, 4.35; N, 4.32; F, 24.64.
Step-3: Preparation of 10-Fluoro-4c,7a,7b,12,13,13a-hexahydro-6H,14H-naphthyl[3,4-a]pyrrolo[3,4-c] carbazole-5,7-(5H,7H)dione A stirred mixture of 2-(2-(6-fluoro-3,4-dihydronaphthyl) indole (500 mg, 1.9 mmol) and maleimide (3 70 mg, 3.8 mmol) in a sealed reaction vial was heated at 180°–190° C. for 2 h. After cooling to ambient temperature, MeOH (3 mL) was added and the product was collected and recrystallized from MeOH to give 465 mg (68%) of a white solid, mp 322°–325° C. $^1$H NMR (acetone-d$_6$, 300 MHz): d 2.76–2.84

(m, 1H, 2.98–3.10 (m, 1H), 3.17–3.20 (m, 1H), 3.95–3.96 (m, 2H), 4.24–4.32 (m, 1H), 4.53 (t, 1H, J=5.8 Hz), 4.93–4.98 (dd, 1H, J=6 Hz, 1.8 Hz), 5.34–5.37 (dd, 1H, J=6.8 Hz, 1.8 Hz), 7.85–7.92 (m, 2H), 7.97–8.09 (m, 3H), 8.30 (d, 1H, J=7.5 Hz), 8.38–8.43 (m, 1H), 8.94 (d, 1H, J=8.1 Hz), MS(m/e)=360 (m$^+$).

Step-4: Preparation of 10-Fluoro-12,13-dihydro-6H,14H-naphthyl[3,4-a]pyrrolo[3,4-c]carbazole-5,7(5H,7H)dione (Compound Ia-4)

To a solution of 10-fluoro-4c,7a,7b,12,13,13 a-hexahydro-6H,14H-naphthyl[3,4-a]pyrrolo[3,4-c] carbazole-5,7-(5H,7H)dione (400 mg, 1.1 mmol) in toluene (50 mL) was added solid 2,3-dichloro-5,6-dicyano-1,4-benzoquinone (630 mg, 2.8 mmol) in one portion. The solution was maintained at 60°–65° C. for six hours. After cooling on an ice bath, the solids were collected by filtration, suspended in MeOH (25 mL) and the product collected by filtration to give 30 mg (77%) of Compound Ia-4, mp 304°–305° C. $^1$H NMR (DMSO-d$_6$, 300 MHz): d 2.91–2.96 (m, 2H), 3.1–3.35 (m, 2H), 7.11–7.18 (m, 1H), 7.24–7.34 (m, 2H), 7.54–7.63 (m, 2H), 8.20 (t, 1H, J=6.5 Hz), 8.94 (d, 1H, J=7.9 Hz), 11.14 (s, 1H), 12.0 (s, 1H). MS (m/e)=325 (m +1)$^+$. Anal. calc. for $C_{22}H_{13}N_2O_2F$: C, 74.15; H, 3.68; N, 7.86. Found; C, 73.79; H, 3.50; N, 7.71.

EXAMPLE V(H)(8)

Step-1: Preparation of 2-(2-(2-Hydroxy-6-bromo-1,2,3,4-tetrahydro)naphthyl)indole The subject compound was prepared by substantially the same procedure as Example V(H)(1), step-1A, except that 6-bromo-2-tetralone and indole were used to give 2-(2-(2-hydroxy-6-bromo-1,2,3,4-tetrahydro)naphthyl)indole; mp 231°–232° C. $^1$H NMR (CDCl$_3$, 300 MHz): d 2.1 (s, 1H), 2.3 (m, 2H), 2.8–2.9 (m, 1H), 3.0–3.15 (m, 2H), 3.4 (m, 2H), 6.25 (s, 1H), 6.8–6.9 (m, 2H), 7.05–7.20 (m, 3H), 7.4 (d, 1H), 8.55 (s, 1H). Anal. calc. for $C_{18}H_{16}FNO$: C, 76.85; H, 5.93; N, 4.98; F, 6.75. Found; C, 76.36; H, 5.75; N, 4.99; F, 6.66.

Step-2: Preparation of 2-(2-(6-bromo-3,4-dihydro)naphthyl) indole

Substantially the same procedure as Example V(H)(1), step-2A, was employed using 2-(2-(2-Hydroxy-6-bromo-1, 2,3,4-tetrahydro)naphthyl)indole (Step-1) to give the subject compound, mp 193°–195° C. $^1$H NMR (CDCl$_3$, 300 MHz): d 2.8 (m, 2H), 2.95 (m, 2H), 6.65 (s, 1H), 6.75 (s, 1H), 6.9 (m, 2H), 7.1 (m, 2H), 7.2 (t, 1H), 7.6 (d, 1H), 8.3 (s, 1H). Anal. calc. for $C_{18}H_{14}FN$: C, 82.11; H, 5.36; N, 5.32; F, 7.22. Found; C, 81.94; H, 5.34; N, 5.30; F, 7.24.

Step-3: Preparation of 10-Bromo-4c,7a,7b,12,13,13 a-hexahydro-6H,14H-naphthyl[3,4-a]pyrrolo[3,4-c] carbazole-5,7-(5H,7H)dione A stirred mixture of 2-(2-(6-bromo-3,4-dihydro)naphthyl) indole (400 mg, 0.95 mmol) and maleimide (540 mg, 2.4 mmol) in a sealed reaction vial was heated at 190° C. for 2 h. After cooling to ambient temperature, MeOH (3 mL) was added and the product was collected and recrystallized from MeOH to give 500 mg (77%) of the subject compound as a yellow solid, mp>320° C. $^1$H NMR (DMSO-d$_6$, 300 MHz): d 1.61 (m, 1H), 2.10 (m, 1H), 2.91–2.93 (m, 2H), 3.17–3.30 (m, 2H), 3.91–3.95 (m, 1H), 4.24 (d, 1H, J=7.7 Hz), 6.97–7.09 (m, 2H), 7.28–7.37 (m, 4H), 7.82 (d, 1H, J=7.8 Hz), 10.86 (s, 1H), 11.14 (s, 1H; MS(m/e)=422 (m+1)$^+$.

Step-4: Preparation of 10-Bromo-12,13-dihydro-6H,14H-naphthyl[3,4-a]pyrrolo[3,4-c]carbazole-5,7(5H,7H)dione (Compound Ia-5)

To a solution of 10-bromo-4c,7a,7b,12,13,13a-hexahydro-6H,14H-naphthyl[3,4-a]pyrrolo[3,4-c] carbazole-5,7-(5H,7H)dione (400 mg, 0.95 mmol) in toluene (50 mL) was added solid 2,3-dichloro-5,6-dicyano-1,4-benzoquinone (540 mg, 2.4 mmol) in one portion. The solution was maintained at 60°–65° C. for six hours. After cooling on an ice bath, the solids were collected by filtration, suspended in MeOH (25 mL) and the product was collected by filtration to give 365 mg (92%) of Compound Ia-5, mp>300° C. $^1$H NMR (DMSO-d$_6$, 300 MHz): d 2.91–2.96 (m, 2H), 3.09–3.12 (m, 2H), 7.25–7.33 (m, 2H), 7.50–7.63 (m, 3H), 8.09 (d, 1H, J=8.5 Hz), 8.93 (d, 1H, J=7.9 Hz), 11.16 (s, 1H), 12.06 (s, 1H). MS (m/e)=418 (m+1)$^+$.

EXAMPLE V(H)(9)

Preparation of 10-(2-(4-Pyridylethenyl))-12,13-dihydro-6H, 14H-naphthyl[3,4-a]pyrrolo[3,4-c]-carbazole-5,7(5H,7H) dione (Compound Ia-6)

To a solution of 10-Bromo-12,13-Dihydro-6H,14H-naphthyl[3,4-a]pyrrolo[3,4-c]carbazole-5,7(5H,7H)dione (Compound Ia-5) (120 mg, 0.29 mmol), 2-vinylpyridine (60 mg, 0.58 mmol) and triethylamine (0.5 mL) in DMF (4 mL) was added tetrakis(triphenylphosphine)palladium(0) (20 mg). The solution was heated in a sealed reaction tube at 100°–110° C. for 48 h. The mixture was cooled to ambient temperature, filtered through a pad of diatomaceous earth (Celite®), and the solvent was concentrated at reduced pressure. The product was triturated with MeOH to give 125 mg (99%) of a yellow solid. Recrystallization from MeOH-Et$_2$O gave Compound Ia-6 as a yellow solid, mp>320° C. $^1$HNMR (DMSO-d$_6$, 300 MHz): d 2.97–3.00 (m, 2H), 3.13–3.17 (m, 2H), 7.29–7.41 (m, 3H), 7.57–7.63 (m, 3H), 7.70 (d, 1H, J=7.7 Hz), 7.77–7.83 (m, 2H), 8.18 d, 1H, J=8.3 Hz), 8.61 (s, 1H), 8.95 (d, 1H, J=7.9Hz), 11.14 (s, 1H), 12.04 (s, 1H). MS(FAB): m/e 442 (m+1)$^+$.

EXAMPLE V(H)(10)

Preparation of 10-(2-(4-Pyridylethyl))-12,13-dihydro-6H, 14H-naphthyl[3,4-a]pyrrolo[3,4-c]-carbazole-5,7(5H,7H) dione (Compound Ia-7)

To 10-(2-(4-Pyridylethenyl))-12,13-Dihydro-6H,14H-naphthyl[3,4-a]pyrrolo[3,4-c]-carbazole-5,7(5H,7I-I)dione (Compound Ia-6) (100 mg, 0.23 mmol) in DMF (30 mL) was added a small spatula of fancy nickel catalyst. The solution was hydrogenated at 40 psi for 12 h. The solvent was filtered through a pad of Celite®, and then concentrated at reduced pressure. The product was recrystallized from MeOH to give 90 mg (90%) of Compound Ia-7 as a light yellow solid, mp>320° C. $^1$H NMR (DMSO-d$_6$, 300 MHz): d 2.93–2.97 (m, 2H), 3.00–3.15 (m, 6H), 7.18–7.34 (m, 5H), 7.54–7.59 (m, 3H), 8.07 (d, 1H, J=8.0), 8.55 (m, 1H), 9.40 (d, 1H, J=7.8 Hz), 11.05 (bs, 1H), 11.98 (s, 1H). MS(FAB): m/e 444 (m+1)$^+$.

EXAMPLE V(H)(11)

Preparation of 5-Hydroxy-12,13-dihydro-6H,14H-naphthyl [3,4-a]pyrrolo[3,4-c]carbazole-7(7H)one (Compound I-38)

To a solution of 12,13-dihydro-6H,14H-naphthyl[3,4-a] pyrrolo[3,4-c]carbazole-5,7(5H,7H)dione (Compound I-15) (25 mg, 0.07 mmol) in DMF (5 mL) was added NaBH$_4$ (50 mg). The mixture was stirred 12 h at ambient temperature, and then concentrated at reduced pressure. The product was recrystallized from DMF-MeOH-Et$_2$O to give 20 mg (80%) of Compound I-38 as a yellow solid, mp>320° C. $^1$H NMR (DMSO-d$_6$, 300 MHz): d 6.5 (bs, 1H), 6.86 (s, 1H), 7.3 (t, 1H), 7.56 (t, 1H), 7.65–7.8 (m, 3H), 8.1 (d, 1H, 8.19 (d, 1H), 8.65 (d, 1H), 9.2–9.3 (m, H), 12.45 (s,1H), MS m/e=337 (m−1)$^+$.

I. Specific Description of Synthetic Processes Preparation of Benzothienyl Fused Pyrrolocarbazoles Part VII: Benzothienyl Derivatives

EXAMPLE V(I)(1)

Preparation of 6H,12-Benzo[b]thieno[2,3-a]pyrrolo[3,4-c]carbazole-5,7(5H,7H)dione (Compound I-20)

A solution of 2-(2-benzo[b]thienyl)indole (FIG. 2, V R, $R^2$, $R^3$=H, X=S, 250 mg, 1.0 mmol), maleimide (120 mg, 1.2 mmol) and trifluoroacetic acid (1 mL) in dry toluene (75 mL) was stirred at reflux for 12 hours. The solution was cooled to ambient temperature and concentrated at reduced pressure to yield a crude solid. The solid was dissolved in glacial HOAc (40 mL). 5% Pd(OAc)$_2$ was added and the mixture maintained at reflux for 12 hours. The solution was cooled to ambient temperature, filtered through Celite®, then concentrated at reduced pressure. MeOH was added to the residue and the product collected (80 mg, 23%). The product was further purified by column chromatography (EtOAc:Hexane 2:1 R$_f$=0.5) to give Compound I-20. The melting point was greater than 300° C. The following NMR data were obtained: $^1$H NMR (DMSO-d$_6$, 300 MHz) δ7.4 (t, 1H, 7.55–7.75 (m, 4H), 8.25 (m, 1H), 9.05 (d, 1H), 9.8 (m, 1H), 11.4 (s, 1H), 12.8 (s, 1H). MS(FAB): m/e=343 (M+1)$^+$. Anal. calc. for: C$_{20}$H$_{10}$N$_2$OS·0.5 H$_2$O ; C, 67.49; H, 3.26; N, 7.87. Found: C, 67.50; H, 3.07; N, 7.51.

EXAMPLES V(I)(2) and V(I)(3)

Preparation of 6H,7H,12H-Benzo[b]thieno[2,3-a]pyrrolo[3,4-c]carbazole-5(5H)one and 6H, 7H, 12H-Benzo[b]thieno[2,3-a]pyrrolo[3,4-c]carbazole-7(7H)one (Compounds I-42 and I-43)

To a stirred suspension of Zn dust (500 mg) and mercuric chloride (150 mg) in water (3 mL) was added dropwise 0.5 mL of concentrated hydrochloric acid. After 10 minutes, the aqueous layer was decanted. The zinc amalgam was first washed with water, then repeatedly with EtOH. The zinc amalgam was suspended in EtOH (10 mL) and solid 6H,12-Benzo[b]thieno[2,3-a]pyrrolo[3,4-c]carbazole-5,7(5H,7H)dione (Compound I-20) (40 mg, 0.12 mmol) was added. A few drops of concentrated hydrochloric acid was added and then the reaction was brought to reflux. After 3 hours the reaction was allowed to cool to ambient temperature and the solvent was removed at reduced pressure. The residue was dissolved in THF-EtOAc (1:1, 50 mL) and extracted with saturated NaCO$_3$ solution (2×25 mL), saturated NaCl solution (2×25 mL), and dried (MgSO$_4$). After filtration the solvent was removed at reduced pressure to give a yellow solid. The product was first purified by column chromotography (silica gel, 2:1 EtOAc/hexanes) to give a mixture of regioisomers of 2:1 (7-oxo/5-oxo). The 5- and 7-oxo isomers were separated by reverse-phase HPLC to give 24 mg of the 7-oxo and 12 mg of the 5-oxo isomers (total yield 89%). The following data were obtained: 5-oxo isomer (Compound I-42), mp>300° C., $^1$H NMR(DMSO-d$_6$, 300 MHz); d 5.10 (s, 2H), 7.26 (t, 1H, J=8.1 Hz), 7.39 (dt, 1H, J=6.9, 1.5 Hz), 7.47 (t, 1H, J=7.3 Hz), 7.61 (dt, 2H, J=6.9, 1.5 Hz), 8.21 (dt, 2H, d=7.3, 5.1 Hz), 8.89 (s, 1H, 9.23 (d, 1H, J=8.1 Hz), 12.31 (s, 1H). MS (ID): m/e 329.17 (m+1). 7-oxo isomer (Compound I-43), mp>300° C. $^1$H NMR (DMSO-d$_6$, 300 MHz); d 5.01 (s, 2H), 7.29 (t, 1H, J=7.3 Hz), 7.35 (m, 1H, 7.53 (m, 1H), 7.68 (t, 2H, J=8.8 Hz), 8.14 (dd, 2H, J=8.8, 5.6 Hz), 8.74 (s, 1H), 10.24 (m, 1H), 12.43 (s, 1H). MS (ID): m/e 329.18 (m+1).

J. Specific Description of Synthetic Processes Preparation of Benzofuranyl Fused Pyrrolocarbazoles Part VIII: Benzofuranyl Derivatives

EXAMPLE V(J)(1)

Preparation of 6H,13H-Benzofuranyl[2,3-a]pyrrolo[3,4-c]carbazole-5,7(5H, 7H)dione (Compound I-21)

This compound was prepared from 2-(2-benzofuranyl)indole (FIG. 2, VI, R, $R^2$, $R^3$=H; X=O) and maleimide by substantially the same procedure as in Part VII to give Compound I-21. The melting point was greater than 300° C. The following NMR data were obtained: $^1$H NMR (DMSO-d$_6$, 300 MHz) δ7.3 (t, 1H), 7.5–7.7 (m, 4H), 7.9 (d, 1H), 8.7 (m, 1H), 8.9 (m, 1H), 11.2 (b, 1H), 12.8 (b, 1H). MS (FAB): m/e 326 (M$^+$).

K. Specific Description of Synthetic Processes Preparation of Aryl, Alkyl, Alkynyl and Substituted Alkyl and Alkanyl Fused Pyrrolocarbazoles Part IX: Aryl, Arylalkenyl and Heteroarylalkenyl Derivatives

EXAMPLE V(K)(1)

Preparation of 3-Phenyl-5H,6H,12H,13H-indeno[2,3-a]pyrrolo[3,4-c]carbazole-7(7H)one (Compound I-27)

A solution of 3-bromo-5H,6H,12H,13H-indeno[2,3-a]pyrrolo[3,4-c]carbazole-7(7H)one (Compound I-9) (100 mg, 0.26 mmol), phenylboronic acid (35 mg, 0.29 mmol) and bis(triphenylphosphine)palladium(II) chloride (25 mg) in DMF (5 ml) was heated in a sealed reaction tube at 100°–110° C. for 24 hours. The mixture was cooled to ambient temperature, filtered through a pad of Celite® and concentrated at reduced pressure. The product was triturated with THF to give 77 mg of a brown solid which contained product and starting material. HPLC purification gave Compound I-27 as a tan solid. The melting point was greater than 300° C. The following NMR data were obtained: $^1$H NMR (DMSO-d$_6$, 300 MHz): δ4.2 (s, 2H), 5.05 (s, 2H), 7.3–7.55 (m, 5H), 7.7 (d, 2H, J=8 Hz), 7.8–7.9 (m, 3H), 8.2 (s, 1H); 8.6 (s, 1H), 9.4 (d, 1H, J=9Hz), 12.0 (s, 1H). MS(FAB): m/e 387 (m+1)$^+$.

EXAMPLE V(K)(2)

Preparation of 3-(2-Phenylethenyl)-5H,6H,12H,13H-indeno[2,3-a]pyrrolo[3,4-c]carbazole-7(7H)-one (Compound I-24)

To a solution of 3-bromo-5H,6H,12H,13H-indeno[2,3-a]pyrrolo[3,4-c]carbazole-7(7H)one (Compound I-9) (100 mg, 0.26 mmol), styrene (30 mg, 0.29 mmol) and triethylamine (0.5 mL) in DMF (4 mL) was added tetrakis (triphenylphosphine)palladium(0) (25 mg). The solution was heated in a sealed reaction tube at 100°–110° C. for 48 hours. The mixture was cooled to ambient temperature, filtered through a pad of Celite®, then the solvent was concentrated at reduced pressure. The product was triturated with MeOH to give 85 mg (80%) of a brown solid. Recrystallization from DMF-Et$_2$O gave the product, Compound I-24, as a tan solid. The melting point was greater than 300° C. The following NMR data were obtained: $^1$H NMR (DMSO-d$_6$, 300 MHz): δ4.2 (s, 2H), 5.02 (s, 2H), 7.25–7.5 (m, 7H), 7.6–7.75 (m,4H), 7.8 (d, 1H, J=8Hz), 8.2 (s, 1H), 8.6 (s, 1H), 9.4 (d, 1H, J=9 Hz), 12.8 (s, 1H). MS(FAB): m/e 413 (m+1)$^+$.

EXAMPLE V(K)(3)

3-(2-Pyridinylethenyl)-5H,6H,12H,13H-indeno[2,3-a]pyrrolo[3,4-c]carbazole-7(7H)-one (Compound I-32).

To a solution of 3-bromo-5H,6H,12H,13H-indeno[2,3-a]pyrrolo[3,4-c]carbazole-7(7H)one (Compound I-9) (100 mg, 0.26 mmol), 2-vinylpyridine (54 mg, 0.6 mL, 0.51 mmol) and triethylamine (0.5 mL) in DMF (4 mL) was added tetrakis(triphenylphosphine)palladium(0) (30 mg). The solution was heated in a sealed reaction tube at 100°–110° C. for 48 h. The mixture was cooled to ambient temperature, filtered through a pad of Celite®, then the solvent was concentrated at reduced pressure. The product was triturated with MeOH to give 90 mg (84%) of Compound I-31 as a yellow solid, purification by column chromatography (silica gel, EtOAc:MeOH, 9:1), mp>320° C. $^1$H NMR (DMSO-$d_6$, 300 MHz): δ4.2 (s, 2H), 5.0 (s, 2H), 7.2–7.42 (m, 4H), 7.58–7.7 (m, 4H), 7.8–7.95 (m, 2H), 8.3 (s, 1H), 8.6 (d, 1H, J=6 Hz), 8.63 (s, 1H), 9.4 (d, 1H, J=9 Hz), 12.1 (s, 1H). MS(FAB): m/e 414 (m+1)$^+$.

Part X: Ester Derivatives

EXAMPLE V(K)4

Preparation of 3-(3-Ethyl propenoate)-5H,6H, 12H,13H-indeno[2,3-a]pyrrolo[3,4-c]carbazole-7(7H)one (Compound I-25)

To a solution of 3-bromo-5H,6H,12H,13H-indeno[2,3-a]pyrrolo[3,4-c]carbazole-7(7H)one (Compound I-9) (100 mg, 0.26 mmol), ethyl acrylate (52 mg, 0.05 mL, 0.52 mmol) and triethylamine (0.5 mL) in DMF (4 mL) was added tetrakis(triphenylphosphine)palladium(0) (25 mg). The solution was heated in a sealed reaction tube at 100°–110° C. for 48 h. The mixture was cooled to ambient temperature, filtered through a pad of Celite®, and concentrated at reduced pressure. The product was triturated with MeOH to a solid, and it was recrystallized from THF-MeOH to give 75 mg (72%) of Compound I-25 as a tan solid. The melting point was greater than 300° C. The following NMR data were obtained: $^1$H NMR (DMSO-$d_6$, 300 MHz): δ1.3 (t, 3H, J=6 Hz), 4.2–4.3 (s, m, 4H), 5.0 (s, 2H), 6.75 (d, 1H, J=20 Hz), 7.35–7.5 (m, 2H), 7.6–7.75 (m, 2H), 7.85–7.95 (m, 2H), 8.4 (s, 1H), 8.65 (m, 1H), 9.4 (d, 1H, 8 Hz), 12.2 (s, 1H). MS(FAB): m/e 409 (m+1)$^+$.

EXAMPLE V(K)(5)

Preparation of 3-(2-(4-Pyridyl)ethenyl)-5H,6H,12H,13H-indeno[2,3-a]pyrrolo[3,4-c]carbazole-7(7H)-one (Compound I-33)

To a solution of 3-bromo-5H,6H,12H,13H-indeno[2,3-a]pyrrolo[3,4-c]carbazole-7(7H)one (Compound I-9) (100 mg, 0.26 mmol), 4-vinylpyridine (55 mg, 0.52 mmol) and triethylamine (0.5 mL) in DMF (4 mL) was added tetrakis(triphenylphosphine)palladium(0) (30 mg). The solution was heated in a sealed reaction tube at 100°–110° C. for 48 h. The mixture was cooled to ambient temperature, filtered through a pad of Celite®, and the solvent was concentrated at reduced pressure. The product was triturated with MeOH to give 75 mg (70%) of a tan solid. Recrystallization from DMF-THF-Et$_2$O gave Compound I-33 as a tan solid, mp>330° C. $^1$HNMR (DMSO-$d_6$, 300 MHz): d 4.19 (s, 2H), 5.02 (s, 2H), 7.30–7.43 (m, 3H), 7.59–7.85 (m,6H), 8.28 (s, 1H), 8.55 (bs, 2H), 8.65 (s, 1H), 9.41 (d, 1H, J=7.3 Hz), 12.10 (s, 1H). MS m/e=414 (m+1)$^+$. Anal. calc. for C$_{28}$H$_{19}$N$_3$O.2.5 H$_2$O:C, 73.35, H, 5.28; N, 9.16. Found; C, 73.66; H, 4.92; N, 8.82.

EXAMPLE V(K)(6)

Preparation of 3-(2-(2-Phthalimido)ethenyl)-5H,6H,12H, 13H-indeno[2,3-a]pyrrolo[3,4-c]carbazole-7(7H)-one (Compound I-39)

To a solution of 3-bromo-5H,6H,12H,13H-indeno[2,3-a]pyrrolo[3,4-c]carbazole-7(7H)one (Compound I-9) (150 mg, 0.39 mmol), N-vinylphthalimide (134 mg, 0.77 mmol) and triethylamine (0.5 mL) in DMF (4 mL) was added tetrakis(triphenylphosphine)palladium(0) (25 mg). The solution was heated in a sealed reaction tube at 100°–110° C. for 48 h. The mixture was cooled to ambient temperature, filtered through a pad of Celite®, and the solvent was concentrated at reduced pressure. The product was triturated with MeOH to give 85 mg (80%) of a brown solid. Recrystallization from DMF-Et$_2$O gave Compound I-39 as a tan solid, mp>300° C. $^1$H NMR (DMSO-$d_6$, 300 MHz): d 4.17 (s, 2H), 5.03 (s, 2H), 7.35–7.42 (m, 4H), 7.60–7.72 (m, 4H), 7.87–7.97 (m, 3H), 8.10 (s, 1H), 8.61 (s, 1H), 9.40 (d, 1H, J=7.2 Hz), 12.03 (s, 1H). MS m/e=504.5 (m +23(Na))$^+$.

EXAMPLE V(K)(7)

Preparation of 3-(2-(2-Pyridylethenyl))-6H,7H,12H,13H-indeno[2,3-a]pyrrolo[3,4-c]carbazole-5(5H)-one (Compound I-41)

To a solution of 3-bromo-6H,7H,12H,13H-indeno[2,3-a]pyrrolo[3,4-c]carbazole-5(5H)one (Compound I-8) (450 mg, 1.16 mmol), 2-vinylpyridine (245 mg, 2.3 mmol) and triethylamine (0.5 mL) in DMF (6 mL) was added tetrakis-(triphenylphosphine)palladium(0) (25 mg). The solution was heated in a sealed reaction tube at 100°–110° C. for 48 h. The mixture was cooled to ambient temperature, filtered through a pad of Celite®, and the solvent was concentrated at reduced pressure. The product was triturated with MeOH to give 300 mg (67%) of Compound I-41 as a light yellow solid. A sample was purified by column chromatography (EtOAc:PAW (pyr:HOAc:H2O; 55:25:20)85:15), mp>320° C. $^1$H NMR (DMSO-$d_6$, 300 MHz): d 4.22 (s, 2H), 4.92 (s, 2H), 7.21–7.28 (m, 2H), 7.38–7.55 (m, 2H), 7.60–7.65 (m, 3H), 7.70–7.85 (m, 4H), 8.6 (m, 2H), 8.82 (s, 1H), 9.4 (m, 1H), 12.05 (s, 1H). MS m/e=414 (m+1)$^+$.

EXAMPLE V(K)(8)

Preparation of 3-(2-(2-Pyridylethyl)-5H,6H,12H,13H-indeno[2,3-a]pyrrolo[3,4-c]carbazole-7(7H)-one (Compound I-34)

To Compound I-32 (Example V(K)(3) (460 mg, 1.1 mmol) in DMF (25 mL) was added a small spatula of raney nickel catalyst then the solution was hydrogenated at 40 psi for 12 h. The solvent was filtered through a pad of Celite®, and then concentrated at reduced pressure. MeOH was added and the product collected to give 410 mg (89%) of Compound I-34 as a light yellow solid, mp>300° C. $^1$H NMR (DMSO-$d_6$, 300 MHz): d 3.17–3.22 (bs, 4H), 4.15 (s, 2H), 4.89 (s, 2H), 7.22–7.41 (m, 5H), 7.51 (d, 1H, J=8.2 Hz), 7.66–7.71 (m, 2H), 8.55 (s, 2H), 9.39 (d, 1H, J=7.5 Hz), 11.82 (s, 1H). MS m/e=415 (m+1)$^+$. Anal. calc. for C$_{28}$H$_{21}$N$_3$O.1.0 H$_2$O : C, 77.58; H, 5.35; N, 9.69. Found; C, 77.54; H, 4.93; N, 9.35.

EXAMPLE V(K)(9)

Preparation of 3-(2-Cyanoethenyl)-5H,6H,12H,13H-indeno[2,3-a]pyrrolo[3,4-c]carbazole-7(7H)-one (Compound I-35)

To a solution of 3-bromo-5H,6H,12H,13H-indeno[2,3-a]pyrrolo[3,4-c]carbazole-7(7H)one (Compound I-9) (100 mg, 0.26 mmol), cyanoacrylate (0.43 ml, 0.51 mmol) and triethylamine (0.5 mL) in DMF (3 mL) was added tetrakis (triphenylphosphine)palladium(0) (20 mg). The solution was heated in a sealed reaction tube at 100°–110° C. for 48 h. The mixture was cooled to ambient temperature, filtered through a pad of Celite®, and the solvent was concentrated at reduced pressure. The product was triturated with MeOH to give 90 mg (97%) of a tan solid. Recrystallization from DMF-Et$_2$O gave Compound I-35 as a tan solid, mp>330° C. $^1$H NMR (DMSO-d$_6$, 300 MHz): d 4.2 (s, 2H), 5.0 (s, 2H), 7.3–7.5 (m, 3H), 7.6–7.95 (m,4H), 8.35 (s, 1H), 8.65 (s, 1H), 9.4 (d, 1H, J=9 Hz), 12.25 (s, 1H); IR: 2220 cm$^{-1}$; MS m/e=362 (m+1)$^+$.

EXAMPLE V(K)(10)

Preparation of 3-Ethynyl-5H,6H,12H,13H-indeno[2,3-a] pyrrolo[3,4-c]carbazole-7(7H)one (Compound I-36)

To a solution of 3-bromo-5H,6H,12H,13H-indeno[2,3-a] pyrrolo[3,4-c]carbazole-7(7H)one (Compound I-9) (435 mg, 1.1 mmol), trimethylsilylacetylene (0.47 ml, 3.3 mmol) and triethylamine (1.0 mL) in DMF (11 mL) was added bis(triphenylphosphine)palladium(II)chloride (17 mg). The solution was heated in a sealed reaction tube at 100°–110° C. for 24 h. The mixture was cooled to ambient temperature, filtered through a pad of celite then the solvent concentrated at reduced pressure. The product was dissolved in DMF (8 mL), MeOH (8 mL) cesium fluoride (370 mg, 2.4 mmol) added and the mixture stirred at ambient temperature 24 h. The solvent was concentrated at reduced pressure to give a dark solid. Purification by column chromatography (silica gel, EtOAc:MeOH; 10:1, R$_f$=0.53) give 30 mg of a tan solid. The compound was further purified by preparative TLC (silica gel, EtOAc:hexane; 3:1) to give Compound I-36 as a tan solid, mp>300° C. $^1$H NMR (DMSO-d$_6$, 300 MHz): d 4.2 (s, 2H), 5.0 (s, 2H), 7.38–7.46 (m, 3H), 7.58–7.75 (m,4H), 8.15 (s, 1H), 9.42 (d, 1H, J=9 Hz), 12.19 (s, 1H; MS m/e=335 (m$^+$).

EXAMPLE V(K)(11)

Step-1: Preparation of 5-Pentyl-2-(2-(2-hydroxyindenyl)) indole

5-Pentyl-2-(2-(2-hydroxyindenyl))indole was prepared by substantially the same procedure as Example V(A)(1), step-1A, except that 2-indanone and 5-pentylindole were used. 5-Pentyl-2-(2-(2-hydroxyindenyl))indole was immediately used in the next step.

Step-2: Preparation of 5-Pentyl-2-(2-indenyl)indole

Substantially the same procedure as Example V(A)(1), step-2A, was employed using 5-pentyl-2-(2-(2-hydroxyindenyl))indole (Step-1) to give the subject compound, mp 222°–223° C. $^1$H NMR (CDCl$_3$, 300 MHz): d 1.9 (m, 3H), 1.4 (m, 4H), 1.7 (m, 2H), 2.65 (m, 2H), 3.9 (s, 2H), 6.6 s, 1H), 7.1 (m, 2H), 7.2–7.35 (m, 3H), 7.4 (m, 2H), 7.5 (d, 1H), 8.2 (s, 1H). Anal. calc. for C$_{22}$H$_{23}$N: C, 87.66; H, 7.69; N, 4.65. Found; C, 87.33; H, 7.72; N, 4.58.

Step-3: Preparation of 3-Pentyl-4c,7a,7b,12a-tetrahydro-6H, 12H,13H-indeno[2,3-a]pyrrolo[3,4-c]carbazole-5,7-(5H, 7H)dione.

A mixture of 5-pentyl-2-(2-indenyl)indole (Step-2) (300 mg, 1.0 mmol) and maleimide (193 mg, 2.0 mmol) in a 10 cm sealed reaction vial was heated at 180°–190° C. for 1 h. After cooling to ambient temperature, the product was dissolved in MeOH (5 mL), and then concentrated at reduced pressure. The product was purified by column chromatography (silica gel, EtOAc:hexane; 2:1) to give 260 mg (66%) of the subject compound as a yellow foam. $^1$H NMR (CDCl$_3$, 300 MHz): d 0.89 (t, 3H, J=5.5 Hz), 1.26–1.35 (m, 4H), 1.63–1.67 (m, 2H), 2.68–2.75 (m, 2H), 2.94–3.02 (m, 1H), 3.30–3.36 (m, 1H), 3.70–3.89 (m, 3H), 4.40 (m, 1H), 6.74 (s, 1H), 7.05 (d, 1H, J=7.2 Hz), 7.14–7.39 (m, 5H), 7.80 (s, 1H), 7.98 (s, 1H).

Step-4: Preparation of 3-Pentyl-6H,12H,13H-indeno[2,3-a] pyrrolo[3,4-c]carbazole-5,7(5H,7H)dione (Compound I-37)

To a solution of the product from step-3 (250 mg, 0.63 mmol) in toluene (15 mL) was added solid 2,3-dichloro-5, 6-dicyano-1,4-benzoquinone (356 mg, 1.57 mmol) in one portion. The solution was maintained at 60°–65° C. for 6 hours. After cooling on an ice bath, the solids were collected by filtration. The product was purified by column chromatography (silica gel, EtOAc:hexane; 2:1) to give 75 mg (30%) of Compound I-37 as a dark solid, mp>300° C. $^1$H NMR (CDCl$_3$, 300 MHz): d 0.94 (m, 3H), 1.40 (m, 4H), 1.74 (m, 2H), 2.80 (m, 2H), 4.28 (s, 2H), 6.96 (s, 1H), 6.4–6.6 (m, 3H), 7.8 (d, 1H, J=6.9 Hz), 7.8 (s, 1H), 9.13 (d, 1H, J=7.2 Hz), 11.23 (s, 1H), 12.15 (s, 1H). MS m/e=393 (m−1)$^+$.

L. Specific Description of Synthetic Processes
Preparation of Allyl Fused Pyrrolocarbazoles Part XI: Allyl Derivatives

EXAMPLE V(L)(1)

Preparation of 13-Allyl-5H,6H,12H-indeno[2,3-a]pyrrolo[3, 4-c]carbazole-7(7H)one (Compound I-26)

5H,6H,12H,13H-Indeno[2,3-a]pyrrolo[3,4-c]carbazole-7 (7H)one (Compound I-2) (200 mg, 0.65 mmol) was added to a stirred solution of NaH (25 mg of 60% oil dispersion, 0.65 mmol) in dry DMF (10 mL) under a nitrogen atmosphere. The dark mixture was stirred at ambient temperature for 1 h, then allyl bromide (87 mg, 0.08 mL, 0.72 mmol) was added dropwise, and the mixture was stirred 12 hours at ambient temperature. The resulting yellow solution was concentrated at reduced pressure to give a solid. The product was crystallized from MeOH to give 90 mg (40%) of Compound I-26 as a yellow solid. The melting point was greater than 300° C. The following NMR data were obtained: 1H NMR (DMSO-d$_6$, 300 MHz): δ3.45 (s, 2H), 4.7 (d, 1H), 4.95 (s, 2H), 5.1 (d, 1H, 5.4 (s, 2H), 6.2–6.3 (m, 1H, 7.35–7.45 (m, 3H), 7.55 (t, 1H), 7.7 (m, 2H), 8.05 (d, 1H, J=8 Hz), 8.6 (s, 1H; 9.5 (d, 1H, J=9 Hz). MS(FAB): m/e 351 (m+1)$^+$.

M. Specific Description of Synthetic Processes
Preparation of Oxo Fused Pyrrolocarbazoles Part XII: Oxo Derivatives

EXAMPLE V(M)(1)

Preparation of 12-Oxo-6H,13H-indeno[2,3-a]pyrrolo[3,4-c] carbazole-5,7(5H,7H)dione (Compound I-28)

To a solution of CrO$_3$ (465 mg, 4.65 mmol) in pyridine (20 mL) was added 6H,12H,13H-indeno[2,3-a]pyrrolo[3,4-c]carbazole-5,7(5H, 7H)dione (Compound I-1), and the mixture was stirred at ambient temperature for 2.5 days. An excess of THF was added and the solution was filtered through a pad of Celite®. The THF solution was washed well with saturated NaCl solution, then concentrated at reduced pressure to give an orange solid product. The product was recrystallized from THF-MeOH to give 270 mg (86%) of Compound I-28 as an orange solid. The melting point was greater than 300° C. The following NMR data were obtained: $^1$H NMR (DMSO-d$_6$, 300 MHz): δ7.35 (t, 1H, J=6 Hz), 7.45 (t, 1H, J=6 Hz), 7.6 (t, 1H, J=6 Hz), 7.7 (m, 3H), 8.7 (d, 1H, J=9 Hz); 8.9 (d, 1H, J=9 Hz), 11.6 (s, 1H), 12.4 (s, 1H). MS(FAB): m/e 338 (M$^+$).

EXAMPLE V(M)(2)

7-Hydroxy-12-oxo-6H,13H-indeno[2,3-a]pyrrolo[3,4-c]carbazole-5(5H)dione (Compound I-30) and 5-Hydroxy-12-oxo-6H,13H-indeno[2,3-a]pyrrolo[3,4-c]carbazole-7(7H)dione (Compound I-31)

To a stirred solution of 12-oxo-6H,13H-indeno[2,3-a]pyrrolo[3,4-c]carbazole-5,7(5H,7H)dione (Compound I-28) (75 mg, 0.22 mmol) in DMF/MeOH (10 mL, 1:1) was added solid sodium borohydride (50 mg, 1.3 mmol) in one portion. The mixture was stirred 14 h at ambient temperature, then concentrated at reduced pressure. MeOH was added and the product triturated to give 25 mg (33%) of a 2:1 mixture of Compound I-31:Compound I-30 as an orange solid. mp>330° C. $^1$H NMR(DMSO-$d_6$+D20, 300 MHz): δ6.32 (s, 0.33H), 6.4 (s, 0.66 H), 7.25–7.7 (m, 5H) 7.95 (d, 0.33H, J=6.7 Hz), 8.25 (d, 0.67H, J=6.7 Hz), 8.76 (m, 0.67H), 8.9 (m, 1.33H). MS(FAB): m/e 341 (m+1)$^+$.

N. Specific Description of Synthetic Processes
Preparation of Lower Hydroxyalkyl Fused Pyrrolocarbazoles Part XIII: Lower Hydroxyalkyl Derivatives

EXAMPLE V(N)(1)

Preparation of 13-(2-Hydroxyethyl)-5H,6H,12H,13H-indeno[2,3-a]pyrrolo[3,4-c]carbazole-7(7H)one (Compound I-29)

5H,6H,12H,13H-indeno[2,3-a]pyrrolo[3,4-c]carbazole-7(7H)one (Compound I-2) (200 mg, 0.65 mmol) was added to a stirred solution of NaH (25 mg of 60% oil dispersion, 0.65 mmol) in dry DMF (10 mL) under a nitrogen atmosphere. The dark mixture was stirred at ambient temperature for 1 hour. Ethyl bromoacetate (120 mg, 0.08 mL, 0.72) was added dropwise and the mixture was stirred 12 hours. The resulting yellow solution was concentrated at reduced pressure to give a crude yellow solid. The product was dissolved in dry THF (10 mL) and lithium aluminium hydride (1 mL of 1M solution in ether) was added dropwise. The solution was stirred 6 hours at room temperature, then the reaction was quenched by the addition of $H_2O$ (1 mL). The mixture was filtered and concentrated at reduced pressure. THF was added to the residue and the product was collected to give 30 mg(17%) of Compound I-29 as a white solid. The melting point was greater than 300° C. The following NMR data were obtained: $^1$H NMR (DMSO-$d_6$, 300 MHz): δ3.8–3.9 (b, 2H), 4.55 (s, 2H), 4.77 (t, 2H), 4.9 (s, 2H), 5.0 (b, 1H, $D_2O$ exchange), 7.3–7.45 (m, 3H), 7.5–7.57 (t, 1H), 7.67 (d, 1H, J=6 Hz), 7.5 (d, 1H, J=6 Hz), 8.0 (d, 1H, J=6 Hz); 8.57 (s, 1H), 9.5 (d, 1H, J=7 Hz). MS(FAB): m/e 355 (M+1)$^+$.

Although our invention has been described in considerable detail, those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the scope of the invention.

What is claimed is:
1. A fused pyrrolocarbazole defined by the formula:

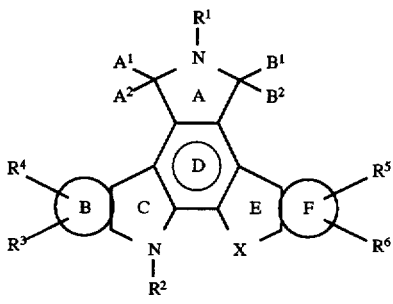

wherein:
a) B and F, independently, and each together with the carbon atoms to which they are attached, form either
   1) an unsaturated 6-membered carbocyclic aromatic ring in which from one to three carbon atom(s) may be replaced by nitrogen atom(s); or
   2) an unsaturated 5-membered carbocyclic aromatic ring in which either
      i) one carbon atom is replaced with an oxygen, nitrogen, or sulfur atom; or
      ii) two carbon atoms are replaced with a sulfur and nitrogen atom, or an oxygen and nitrogen atom;
b) $R^1$ is selected from the group consisting of H, alkyl of 1–4 carbons, aryl, arylalkyl, heteroaryl, and heteroarylalkyl; $COR^9$, where $R^9$ is selected from the group consisting of alkyl of 1–4 carbons, and aryl, $—OR^{10}$, where $R^{10}$ is selected from the group consisting of H and alkyl of 1–4 carbons; $—CONH_2$, $—NR^7R^8$, $—CH_2)_nNR^7R^8$, wherein n is an integer selected from the group consisting of 1–4; and $—OCH_2)_nNR^7R^8$; wherein either
   1) $R^7$ and $R^8$ are each independently selected from the group consisting of H and alkyl of 1–4 carbons; or
   2) $R^7$ and $R^8$ are combined together to form a linking group of the general formula $—(CH_2)_2—X^1—(CH_2)_2—$, where $X^1$ is selected from the group consisting of O, S and $CH_2$; c) $R^2$ is selected from the group consisting of H, $—SO_2R^9$; $—CO_2R^9$, $—COR^9$, alkyl of 1–8 carbons, alkenyl of 2–8 carbons, alkynyl of 2–8 carbons, and a monosaccharide of 5–7 carbons wherein each hydroxyl group of said monosaccharide is independently selected from a group consisting of an unsubstituted hydroxyl group and a replacement moiety replacing said hydroxyl group, said replacement moiety selected from the group consisting of H, alkyl of 1–4 carbons, alkylcarbonyloxy of 2–5 carbons and alkoxy of 1–4 carbons; wherein either
   1) each alkyl of 1–8 carbons, alkenyl of 2–8 carbons, or alkynyl of 2–8 carbons is unsubstituted; or
   2) each alkyl of 1–8 carbons, alkenyl of 2–8 carbons, or alkynyl of 2–8 carbons is independently substituted with a moiety selected from the group consisting of 1–3 aryl of 6–10 carbons; phenyl, naphthyl; heteroaryl, F, Cl, Br, I, $—CN$, $—NO_2$, OH, $—OR^9$, $—O(CH_2)_nNR^7R^8$, $—OCOR^9$, $—OCONHR^9$, O-tetrahydropyranyl, $NH_2$, $—NR^7R^8$, $—NR^{10}COR^9$; $—NR^{10}CO_2R^9$, $—NR^{10}CONR^7R^8$, $—NHC(=NH)NH_2$, $—NR^{10}SO_2R^9$, $—S(O)_yR^{11}$, wherein $R^{11}$ is selected from the group consisting of H, alkyl of 1–4 carbons, aryl of 6–10 carbons, and heteroaryl wherein y is an integer selected from the group consisting of 1 and 2; —SR$^{11}$, —CO$_2$R$^9$, —CONR$^7$R$^8$, —CHO, COR$^9$, —CH$_2$OR$^7$, —CH=NNR$^{11}$R$^{12}$, —CH=NOR$^{11}$, —CH=NR$^9$, —CH=NNHCH(N=NH)NH$_2$, —SO$_2$NR$^{12}$R$^{13}$, —PO(OR$^{11}$)$_2$, and OR$^{14}$ where R$^{14}$ is the residue of an amino acid after the hydroxyl group of the carboxyl group is removed; and wherein either i) R$^{12}$ and R$^{13}$ are each independently selected from the group consisting of H alkyl of 1–4 carbons, aryl of 6–10 carbons, and heteroaryl; or ii) R$^{12}$ and R$^{13}$ are combined together to form a linking group of the general formula —(CH$_2$)$_2$—X$^1$—(CH$_2$)$_2$;

d) R$^3$, R$^4$, R$^5$ and R$^6$ are each independently selected from the group consisting of H, aryl, heteroaryl; F, Cl, Br, I, —CN, CF$_3$, —NO$_2$, OH, —OR$^9$, —O(CH$_2$)$_n$NR$^7$R$^8$, —OCOR$^9$, —OCONHR$^9$, NH$_2$, —CH$_2$OH, —CH$_2$OR$^{14}$, —NR$^7$R$^8$, —NR$^{10}$COR$^9$, —NR$^{10}$CONR$^7$R$^8$, —SR$^{11}$, —S(O)$_y$R$^{11}$ wherein is an integer selected from the group consisting of 1 and 2; —CO$_2$R$^9$, —COR$^9$, —CONR$^7$R$^8$, —CHO, —CH=NOR$^{11}$, —CH=NR$^9$, —CH=NNR$^{11}$R$^{12}$, —(CH$_2$)$_n$SR$^9$, wherein n is an integer selected from the group consisting of 1–4, —CH$_2$)$_n$S(O)$_y$R$^9$, —CH$_2$SR$^{15}$ where R$^{15}$ is an alkyl of 1–4 carbons; —CH$_2$S(O)$_y$R$^{14}$, —CH$_2$)$_n$NR$^7$R$^8$, —CH$_2$)$_n$NHR$^{14}$, alkyl of 1–8 carbons, alkenyl of 2–8 carbons; alkynyl of 2–8 carbons; wherein either 1) each alkyl of 1–8 carbons, alkenyl of 2–8 carbons or alkynyl of 2–8 carbons is unsubstituted; or 2) each alkyl of 1–8 carbons, alkenyl of 2–8 carbons or alkynyl of 2–8 carbons as defined in (c)(2), above;

e) X is selected from the group consisting of 1) an unsubstituted alkylene of 1–3 carbons; and 2) an alkylene of 1–3 carbons substituted by R$^2$, OR$^{10}$, —SR$^{10}$, R$^{15}$, where R$^{15}$ is selected from the group consisting of an alkyl of 1–4 carbons; phenyl, naphthyl, arylalkyl of 7–14 carbons, and 3) —CH=CH—, —CH(OH)CH(OH)—, —O—, —S—, —S(=O)—, S(=O)$_2$—, —C(=O)—, —C(=NOR$^{11}$)—, —C(OR$^{11}$)(R$^{11}$)—, —C(=O)CH(R$^{15}$)—, —CH(R$^{15}$)C(=O)—, —C(R$^{10}$)$_2$—, —C(=NOR$^{11}$)CH(R$^{15}$)—, —CH(R$^{15}$)C(=NOR$^{11}$)—, —CH$_2$Z—, —Z—CH$_2$—, —CH$_2$ZCH$_2$—, wherein Z is selected from the group consisting of C(R$^{11}$)(OR$^{11}$), O, S, C(=O), C(=NOR$^{11}$), and NR$^{11}$;

f) A$^1$ and A$^2$ are selected from the group consisting of H, H; H, —OR$^{11}$; H, —SR$^{11}$; H, —N(R$^{11}$)$_2$; and a group wherein A$^1$ and A$^2$ together form a moiety selected from the group consisting of =O; =S; and =NR$^{11}$, and g) B$^1$ and B$^2$ are selected from the group consisting of H, H; H, —OR$^{11}$; H, —SR$^{11}$; H, —NCR$^{11}$)$_2$; and a group wherein B$^1$ and B$^2$ are selected from the group consisting of =O, =S; and =NR$^{11}$ with the proviso that at least one of the pairs A$^1$, A$^2$ or B$^1$, B$^2$ is =O.

2. The fused pyrrolocarbazole of claim 1 defined by the formula:

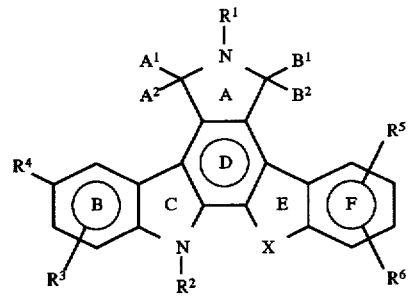

wherein:

a) R$^1$ is selected from the group consisting of H, alkyl of 1–4 carbons, aryl, arylalkyl, heteroaryl, and heteroarylalkyl; COR$^9$, where R$^9$ is selected from the group consisting of alkyl of 1–4 carbons, and aryl; —OR$^{10}$, where R$^{10}$ is selected from the group consisting of H, alkyl of 1–4 carbons; —CONH$_2$, —NR$^7$R$^8$, —(CH$_2$)$_n$NR$^7$R$^8$, wherein n is an integer selected from the group consisting of 1–4; and —O(CH$_2$)$_n$NR$^7$R$^8$; wherein either 1) R$^7$ and R$^8$ are each independently selected from the group consisting of H and alkyl of 1–4 carbons; or 2) R$^7$ and R$^8$ are combined together to form a linking group of the general formula —(CH$_2$)$_2$—X$^1$—(CH$_2$)$_2$—, where X$^1$ is selected from the group consisting of O, S and CH$_2$;

b) R$^2$ is selected from the group consisting of H, —SO$_2$R$^9$; —CO$_2$R$^9$, —COR$^9$, alkyl of 1–8 carbons, alkenyl of 2–8 carbons, alkynyl of 2–8 carbons; and a monosaccharide of 5–7 carbons wherein each hydroxyl group of said monosaccharide is independently selected from the group consisting of an unsubstituted hydroxyl group and a replacement moiety replacing said hydroxyl group, said replacement moiety selected from the group consisting of H, alkyl of 1–4 carbons, alkylcarbonyloxy of 2–5 carbons and alkoxy of 1–4 carbons; wherein either 1) each alkyl of 1–8 carbons, alkenyl of 2–8 carbons, or alkynyl of 2–8 carbons is unsubstituted; or 2) each alkyl of 1–8 carbons, alkenyl of 2–8 carbons, or alkynyl of 2–8 carbons is independently substituted with a moiety selected from the group consisting of 1–3 aryl of 6–10 carbons, phenyl and naphthyl; heteroaryl, F, Cl, Br, I, —CN, —NO$_2$, OH, —OR$^9$, —O(CH$_2$)$_n$NR$^7$R$^8$, —OCOR$^9$, —OCONHR$^9$, O-tetrahydropyranyl, NH$_2$, —NR$^7$R$^8$, —NR$^{10}$COR$^9$; —NR$^{10}$CO$_2$R$^9$, —NR$^{10}$CONR$^7$R$^8$, —NHC(=NH)NH$_2$, —NR$^{10}$SO$_2$R$^9$, —S(O)$_y$R$^{11}$, wherein R$^{11}$ is selected from the group consisting of H, alkyl of 1–4 carbons, aryl of 6–10 carbons, and heteroaryl wherein y is an integer selected from the group consisting of 1 and 2; —SR$^{11}$, —CO$_2$R$^9$, —CONR$^7$R$^8$, —CHO, COR$^9$, —CH$_2$OR$^7$, —CH=NNR$^{11}$R$^{12}$, —CH=NOR$^{11}$, —CH=NR$^9$, —CH=NNHCH(N=NH)NH$_2$, —SO$_2$NR$^{12}$R$^{13}$, —PO(OR$^{11}$)$_2$, or OR$^{14}$ where R$^{14}$ is the residue of an amino acid after the hydroxyl group of the carboxyl group is removed; and wherein either i) R$^{12}$ and R$^{13}$ are each independently selected from the group consisting of H, alkyl of 1–4 carbons, aryl of 6–10 carbons, and heteroaryl; or ii) R$^{12}$ and R$^{13}$ are combined together to form a linking group of the general formula —(CH$_2$)$_2$—X$_1$—(CH$_2$)$_2$;

c) $R^3$, $R^4$, $R^5$ and $R^6$, are each independently selected from the group consisting of H, aryl, heteroaryl; F, Cl, Br, I, —CN, $CF_3$, —$NO_2$, OH, —$OR^9$, —$O(CH_2)_nNR^7R^8$, —$OCOR^9$, —$OCONHR^9$, $NH_2$, —$CH_2OH$, —$CH_2OR^{14}$, —$NR^7R^8$, —$NR^{10}COR^9$, —$NR^{10}CONR^7R^8$, —$SR^{11}$, —$S(O)_yR^{11}$ wherein y is an integer selected from the group consisting of 1 and 2; —$CO_2R^9$, —$COR^9$, —$CONR^7R^8$, —CHO, —CH=$NOR^{11}$, —CH=$NR^9$, —CH=$NNR^{11}R^{12}$, —$CH_2)_nSR^9$, wherein n is an integer of 1–4, —$CH_2)_nS(O)_yR^9$, —$CH_2SR^{15}$ where $R^{15}$ is an alkyl of 1–4 carbons; —$CH_2S(O)_yR^{14}$, —$(CH_2)_nNR^7R^8$, —$CH_2)_nNHR^{14}$, alkyl of 1–8 carbons, alkenyl of 2–8 carbons; alkynyl of 2–8 carbons; wherein either 1) each alkyl of 1–8 carbons, alkenyl of 2–8 carbons or alkynyl of 2–8 carbons is unsubstituted; or 2) each alkyl of 1–8 carbons, alkenyl of 2–8 carbons or alkynyl of 2–8 carbons is defined in (b)(2), above;

d) X is selected from the group consisting of
1) an unsubstituted alkylene of 1–3 carbons; and
2) an alkylene of 1–3 carbons substituted by $R^2$, $OR^{10}$, —$SR^{10}$, $R^{15}$, where $R^{15}$ is selected from the group consisting of an alkyl of 1–4 carbons; phenyl, naphthyl, arylalkyl of 7–14 carbons; and
3) —CH=CH—, —CH(OH)CH(OH)—, —O—, —S—, —S(=O)—, —C(=O)_2—, —C(=O)—, —C(=$NOR^{11}$)—, —C($OR^{11}$)($R^{11}$)—, —C(=O)CH($R^{15}$)—, —CH($R^{15}$)C(=O)—, —C($R^{10}$)_2—, —C(=$NOr^{11}$)CH($R^{15}$)—, —CH($R^{15}$)—, —CH($R^{15}$)C(=$NOR^{11}$)—, —$CH_2Z$—, —Z—$CH_2$—, —$CH_2ZCH_2$—, wherein Z is selected from the group consisting of C($R^{11}$)($OR^{11}$), O, S, C(=O), C(=$NOR^{11}$), and $NR^{11}$;

e) $A^1$ and $A^2$ are selected from the group consisting of H, H; H, —$OR^{11}$; H, —$SR^{11}$; H, —N($R^{11}$)_2, and a group wherein $A^1$ and $A^2$ together form a moiety selected from the group consisting of =O; =S, and =$NR^{11}$; and f) $B^1$ and $B^2$ are selected from the group consisting of H, H; H, —$OR^{11}$; H, —$SR^{11}$; H, —N($R^{11}$)_2; and a group wherein $B^1$ and $B^2$ together form a moiety selected from the group consisting of =O; =S, and =$NR^{11}$; with the proviso that at least one of the pairs of $A^1$, $A^2$ or $B^1$, $B^2$ is =O.

3. The fused pyrrolocarbazole of claim 2 defined by a formula selected from the group consisting of:

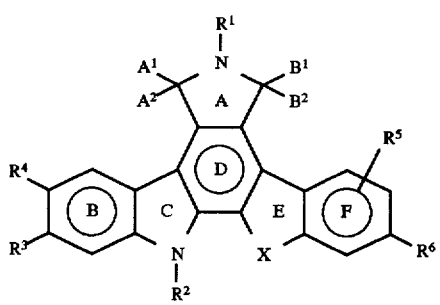

and

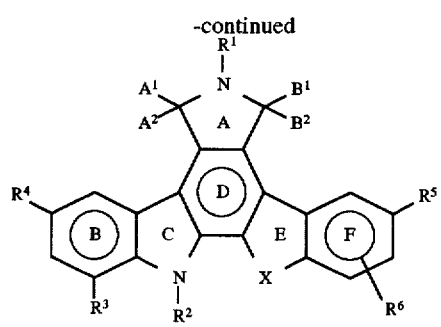

-continued wherein:
a) $A^1$ and $A^2$ are selected from the group consisting of H, H; H, —OH; and =O; and $B^1$ and $B^2$ are selected from the group consisting of H, H; H, —OH; and =O; provided that at least one of $A^1$, $A^2$ or $B^1$, $B^2$ is =O;
b) $R^1$ is H;
c) $R^2$ is selected from the group consisting of H, allyl, hydroxyethyl, and alkyl of 1–4 carbons;
d) $R^3$, $R^4$, $R^5$, and $R^6$, are each independently selected from the group consisting of H, F, Cl, Br, I, alkyl of 1–4 carbons, alkoxyl of 1–4 carbons, heteroarylalkenyl, heteroarylalkyl, cyanoethyl, cyanovinyl, aryl of 6–10 carbons, alkynyl, arylalkenyl, alkoxycarbonylalkenyl, and haloalkenyl;
e) X is selected from the group consisting of
1) an unsubstituted alkylene of 1–3 carbons;
2) an alkylene of 1–3 carbons substituted by $R^2$, —$OR^{11}$, —$SR^{11}$, $R^{15}$; phenyl, naphthyl, arylalkyl of 7–11 carbons; and
3) —CH=CH—, —CH(OH)CH(OH)—, —O—, —S—, —S(=O)—, —S(=O)_2—, —C(=O)—, —C(=$NOR^{11}$)—, —C($OR^{11}$)($R^{11}$)—, —X(=O)CH($R^{15}$)—, —CH($R^{15}$)C(=O)—, —C($R^{10}$)_2—, —C(=$NOR^{11}$)CH($R^{15}$)—, —CH($R^{15}$)C(=$NOR^{11}$)—, —$CH_2Z$—, —Z—$CH_2$—, —$CH_2ZCH_2$—, where Z is selected from the group consisting of C($R^{11}$)($OR^{11}$), O, S, C(=O), C(=$NOR^{11}$), and $NR^{11}$.

4. The fused pyrrolocarbazole of claim 3 wherein:
a) $A^1$ and $A^2$ are selected from the group consisting of H, H; H, —OH; and =O; and $B^1$ and $B^2$ are selected from the group consisting of H, H; H, —OH; and O; provided that at least one of $A^1$, $A^2$ or $B^1$, $B^2$ is =O;
b) $R^1$ is H;
c) $R^2$ is selected frown the group consisting of H, $CH_3$, $CH_2CH$=$CH_2$, and $CH_2CH_2OH$;
d) each $R^3$, $R^4$, $R^5$, and $R^6$, independently, is selected from the group consisting of H, F, Cl, Br, I, $CH_3$, $OCH_3$, HC=$CHC_6H_5$, HC=$CHCO_2H_5$, $C_6H_5$, HC=CH-2-pyr, HC=CH-4-pyr, $H_2CCH_2$-2-pyr, HC=CHCN, C=CH, n-pentyl, HC=CH-2-phthalimide, and HC=CHI; and
e) X is selected from the group consisting of —$CH_2$—, —$CH_2CH_2$—, —CH=CH—, —S—, —O—, and —C(=O)—.

5. The fused pyrrolocarbazole of claim 1 wherein $R^9$ is selected from the group consisting of phenyl and naphthyl.

6. The fused pyrrolocarbazole of claim 1, wherein $R^2$ is selected from the group consisting of H, —$SO_2R^9$; —$CO_2R^9$, —$COR^9$, alkyl of 1–4carbons, alkenyl of 2–4 carbons, alkynyl of 2–4 carbons, and a monosaccharide of 5–7 carbons wherein each hydroxyl group of said monosaccharide is independently selected from a group consisting of an unsubstituted hydroxyl group and a replacement moiety replacing said hydroxyl group, said replacement moiety selected from the group consisting of H, alkyl of 1–4 carbons, alkylcarbonyloxy of 2–5 carbons and alkoxy of 1–4 carbons.

7. The fused pyrrolocarbazole of claim 1 wherein $R^2$ is selected from the group consisting of alkyl of 1–8 carbons, alkenyl of 2–8 carbons, and alkynyl of 2–8 carbons is independently substituted with a moiety selected from the group consisting of phenyl and naphthyl.

8. The fused pyrrolocarbazole of claim 1 wherein $R^2$ is selected from the group consisting of alkyl of 1–8 carbons, alkenyl of 2–8 carbons, and alkynyl of 2–8 carbons is independently substituted with a moiety consisting of —S(O)$_y$R$^{11}$, where R$^{11}$ is selected from the group consisting of phenyl and naphthyl.

9. The fused pyrrolocarbazole of claim 1 wherein $R^3$, $R^4$, $R^5$ and $R^6$ are each independently selected from the group consisting of H, aryl, heteroaryl; F, Cl, Br, I, —CN, CF$_3$, —NO$_2$, OH, —OR$^9$, —(CH$_2$)$_n$NR$^7$R$^8$, —OCOR$^9$, —OCONHR$^9$, NH$_2$, —CH$_2$OH, —CH$_2$OR$^{14}$, —NR$^7$R$^8$, —NR$^{10}$COR$^9$, —NR$^{10}$CONR$^7$R$^8$, —SR$^{11}$, —S(O)$_y$R$^{11}$ wherein y is an integer selected from the group consisting of 1 and 2; —CO$_2$R$^9$, —COR$^9$, —CONR$^7$R$^8$, —CHO, —CH=NOR$^{11}$, —CH=NR$^9$, —CH=NNR$^{11}$R$^{12}$, —(CH$_2$)$_n$SR$^9$, wherein n is an integer selected from the group consisting of 1–4, —(CH$_2$)$_n$S(O)$_y$R$^9$, —CH$_2$SR$^{15}$ where R$^{15}$ is alkyl of 1–4 carbons; —CH$_2$S(O)$_y$R$^{14}$, —(CH$_2$)$_n$NR$^7$R$^8$, —(CH$_2$)$_n$NHR$^{14}$, alkyl of 1–4 carbons, alkenyl of 2–4 carbons; alkynyl of 2–4 carbons.

10. The fused pyrrolocarbazole of claim 9, wherein $R^3$, $R^4$, $R^5$ and $R^6$ are each independently selected from the group consisting of H, aryl of 6–10 carbons, heteroaryl; F, Cl, Br, I, —CN, CF$_3$, —NO$_2$, OH, —OR$^9$, —O(CH$_2$)$_n$NR$^7$R$^8$, —OCOR$^9$, —OCONHR$^9$, NH$_2$, —CH$_2$OH, —CH$_2$OR$^{14}$, —NR$^7$R$^8$, —NR$^{10}$COR$^9$, —NR$^{10}$CONR$^7$R$^8$, SR$^{11}$, —S(O)$_y$R$^{11}$ wherein y is an integer selected from the group consisting of 1 and 2; —CO$_2$R$^9$, —COR$^9$, —CONR$^7$R$^8$, —CHO, —CH=NOR$^{11}$, CH=NR$^9$, —CH=NNR$^{11}$R$^{12}$, —(CH$_2$)$_n$SR$^9$, wherein n is an integer selected from the group consisting of 1–4, —(CH$_2$)$_n$S(O)$_y$R$^9$, —CH$_2$SR$^{15}$ where R$^{15}$ is alkyl of 1–4 carbons; —CH$_2$S(O)$_y$R$^{14}$, —(CH$_2$)$_n$NR$^7$R$^8$, —(CH$_2$)$_n$NHR$^{14}$, alkyl of 1–8 carbons, alkenyl of 2–8 carbons; alkynyl of 2–8 carbons.

11. The fused pyrrolocarbazole of claim 9 wherein $R^3$, $R^4$, $R^5$ and $R^6$ are each independently selected from the group consisting of H, phenyl, naphthyl, heteroaryl; F, Cl, Br, I, —CN, CF$_3$, —NO$_2$, OH, —OR$^9$, —O(CH$_2$)$_n$NR$^7$R$^8$, —OCOR$^9$, —OCONHR$^9$, NH$_2$, —CH$_2$OH, —CH$_2$OR$^{14}$, —NR$^7$R$^8$, —NR$^{10}$COR$^9$, —NR$^{10}$CONR$^7$R$^8$, —SR$^{11}$, —S(O)$_y$R$^{11}$ wherein y is an integer selected from the group consisting of 1 and 2; —CO$_2$R$^9$, —COR$^9$, —CONR$^7$R$^8$, —CHO, —CH=NOR$^{11}$, —CH=NR$^9$, —CH=NNR$^{11}$R$^{12}$, —(CH$_2$)$_n$SR$^9$, wherein n is an integer selected from the group consisting of 1–4, —(CH$_2$)$_n$S(O)$_y$R$^9$, —CH$_2$SR$^{15}$ where R$^{15}$ is alkyl of 1–4 carbons; —CH$_2$S(O)$_y$R$^{14}$, —(CH$_2$)$_n$NR$^7$R$^8$, —(CH$_2$)$_n$NHR$^{14}$, alkyl of 1–8 carbons, alkenyl of 2–8 carbons; and alkynyl of 2–8 carbons.

12. The fused pyrrolocarbazole of claim 1 wherein $R^{12}$ and $R^{13}$ are each independently selected from the group consisting of phenyl and naphthyl.

13. The fused pyrrolocarbazole of claim 1 wherein X is selected from the group consisting of an alkylene of 1–3 carbons substituted by $R^2$ group, —SR$^{10}$, R$^{15}$, where R$^{15}$ is selected from the group consisting of an alkyl of 1–4 carbons; phenyl, naphthyl, and benzyl.

14. The fused pyrrolocarbazole of claim 1 wherein X is an alkylene of 1–3 carbons substituted by OR$^{10}$.

15. The fused pyrrolocarbazole of claim 2 wherein $R^9$ is selected from the group consisting of phenyl and naphthyl.

16. The fused pyrrolocarbazole of claim 2 wherein $R^2$ is selected from the group consisting of H, —SO$_2$R$^9$, —CO$_2$R$^9$, —COR$^9$, alkyl of 1–4 carbons, alkenyl of 2–4 carbons, alkynyl of 2–4 carbons, and a monosaccharide of 5–7 carbons wherein each hydroxyl group of said monosaccharide is independently selected from a group consisting of an unsubstituted hydroxyl group and a replacement moiety replacing said hydroxyl group, said replacement moiety selected from the group consisting of H, alkyl of 1–4 carbons, alkylcarbonyloxy of 2–5 carbons and alkoxy of 1–4 carbons.

17. The fused pyrrolocarbazole of claim 2 wherein $R^2$ is selected from the group consisting of alkyl of 1–8 carbons, alkenyl of 2–8 carbons, and alkynyl of 2–8 carbons is independently substituted with a moiety selected from the group consisting of phenyl and naphthyl.

18. The fused pyrrolocarbazole of claim 2 wherein $R^2$ is selected from the group consisting of alkyl of 1–8 carbons, alkenyl of 2–8 carbons, and alkynyl of 2–8 carbons is independently substituted with a moiety consisting of —S(O)$_y$R$^{11}$, where R$^{11}$ is selected from the group consisting of phenyl and naphthyl.

19. The fused pyrrolocarbazole of claim 2 wherein $R^3$, $R^4$, $R^5$ and $R^6$ are each independently selected from the group consisting of H, aryl, heteroaryl; F, Cl, Br, I, —CN, CF$_3$, —NO$_2$, OH, —OR$^9$, —OCH$_2$)$_n$NR$^7$R$^8$, —OCOR$^9$, —OCONHR$^9$, NH$_2$, —CH$_2$OH, —CH$_2$OR$^{14}$, —NR$^7$R$^8$, —NR$^{10}$COR$^9$, —NR$^{10}$CONR$^7$R$^8$, —SR$^{11}$, —S(O)$_y$R$^{11}$ wherein y is an integer selected from the group consisting of 1 and 2; —CO$_2$R$^9$, —COR$^9$, —CONR$^7$R$^8$, —CHO, —CH=NOR$^{11}$, —CH=NR$^9$, —CH=NNR$^{11}$R$^{12}$, —(CH$_2$)$_n$SR$^9$, wherein n is an integer selected from the group consisting of 1–4, —(CH$_2$)$_n$S(O)$_y$R$^9$, —CH$_2$SR$^{15}$ where R$^{15}$ is alkyl of 1–4 carbons; —CH$_2$S(O)$_y$R$^{14}$, —(CH$_2$)$_n$NR$^7$R$^8$, —(CH$_2$)$_n$NHR$^{14}$, alkyl of 1–4 carbons, alkenyl of 2–4 carbons; and alkynyl of 2–4 carbons.

20. The fused pyrrolocarbazole of claim 19 wherein $R^3$, $R^4$, $R^5$ and $R^6$ are each independently selected from the group consisting of H, aryl of 6–10 carbons, heteroaryl; F, Cl, Br, I, —CN, CF$_3$, —NO$_2$, OH, —OR$^9$, —O(CH$_2$)$_n$NR$^7$R$^8$, —OCOR$^9$, —OCONHR$^9$, NH$_2$, —CH$_2$OH, —CH$_2$OR$^{14}$, —NR$^7$R$^8$, —NR$^{10}$COR$^9$, —NR$^{10}$CONR$^7$R$^8$, —SR$^{11}$, —S(O)$_y$R$^{11}$ wherein y is an integer selected from the group consisting of 1 and 2; —CO$_2$R$^9$, —COR$^9$, —CONR$^7$R$^8$, —CHO, —CH=NOR$^{11}$, —CH=NR$^9$, —CH=NNR$^{11}$R$^{12}$, —(CH$_2$)$_n$SR$^9$, wherein n is an integer selected from the group consisting of 1–4, —(CH$_2$)$_n$S(O)$_y$R$^9$, —CH$_2$SR$^{15}$ where R$^{15}$ is alkyl of 1–4 carbons; —CH$_2$ S(O)$_y$R$^{14}$, —(CH$_2$)$_n$NR$^7$R$^8$, —(CH$_2$)$_n$NHR$^{14}$, alkyl of 2–8 carbons; and alkynyl of 2–8 carbons.

21. The fused pyrrolocarbazole of claim 19 wherein $R^3$, $R^4$, $R^5$ and $R^6$ are each independently selected from the group consisting of H, phenyl, naphthyl, heteroaryl; F, Cl, Br, I, —CN, CF$_3$, —NO$_2$, OH, —OR$^9$, —O(CH$_2$)$_n$NR$^7$R$^8$, —OCOR$^9$, —OCONHR$^9$, NH$_2$, —CH$_2$OH, —CH$_2$OR$^{14}$, —NR$^7$R$^8$, —NR$^{10}$COR$^9$, —NR$^{10}$CONR$^7$R$^8$, —SR$^{11}$, —S(O)$_y$R$^{11}$ wherein y is an integer selected from the group consisting of 1 and 2; —CO$_2$R$^9$, —COR$^9$, —CONR$^7$R$^8$, —CHO, —CH=NOR$^{11}$, —CH=NR$^9$, —CH=NNR$^{11}$R$^{12}$, —(CH$_2$)$_n$SR$^9$, wherein n is an integer selected from the group consisting of 1–4, —(CH$_2$)$_n$S(O)$_y$R$^9$, —CH$_2$SR$^{15}$ where R$^{15}$ is alkyl of 1–4 carbons; —CH$_2$S(O)$_y$R$^{14}$, —(CH$_2$)$_n$NR$^7$R$^8$, —(CH$_2$)$_n$NHR$^{14}$, alkyl of 1–8 carbons, alkenyl of 2–8 carbons; and alkynyl of 2–8 carbons.

22. The fused pyrrolocarbazole of claim 3 wherein R$^{12}$ and R$^{13}$ are each independently selected from the group consisting of phenyl and naphthyl.

23. The fused pyrrolocarbazole of claim 3 wherein X is selected from the group consisting of an alkylene of 1–3 carbons substituted by R$^2$, —SR$^{10}$, and R$^{15}$, where R$^{15}$ is selected from the group consisting of an alkyl of 1–4 carbons; phenyl, naphthyl, and benzyl.

24. The fused pyrrolocarbazole of claim 2 wherein X is an alkylene of 1–3 carbons substituted by OR$^{10}$.

25. The fused pyrrolocarbazole of claim 3 wherein R$^2$ is methyl.

26. The fused pyrrolocarbazole of claim 3 wherein R$^3$, R$^4$, R$^5$ and R$^6$ are each independently selected from the group consisting of H, F, Cl, Br, I, methyl, methoxyl, pyridylyinyl, pyridylethyl, cyanoethyl, cyanovinyl, phenyl, alkynyl, styryl, ethoxycarbonylvinyl and haloalkenyl.

27. The fused pyrrolocarbazole of claim 3 wherein X is an unsubstituted alkylene selected from the group consisting of —CH$_2$ and —CH$_2$CH$_2$.

28. The fused pyrrolocarbazole of claim 3 wherein X is an alkylene selected from the group consisting of substituted —CH$_2$ and —CH$_2$CH$_2$ wherein each alkylene of 1–3 carbons is substituted with one R$^2$ or OR$^{11}$ group.

29. The fused pyrrolocarbazole of claim 28 wherein the substituent is OR$^{11}$.

30. The fused pyrrolocarbazole of claim 3 wherein X is selected from the group consisting of an alkylene of 1–3 carbons substituted by R$^2$, —SR$^{10}$, and R$^{15}$, where R$^{15}$ is selected from the group consisting of an alkyl of 1–4 carbons; phenyl, naphthyl, and benzyl.

31. A method for preparing a D-ring-fused pyrrolocarbazole, the method comprising the steps of:

a) obtaining an indole defined by Formula IV:

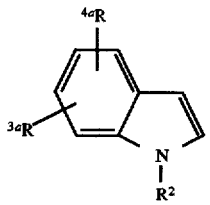

IV wherein:

R$^2$ is selected from the group consisting of H, SO$_2$R$^9$, CO$_2$R$^9$, and alkyl of 1–4 carbons;

R$^{3a}$ and R$^{4a}$ are each independently selected from the group consisting of H, F, Cl, Br, I, —OR$^9$, —O(CH$_2$)$_n$NR$^7$R$^8$, NR$^7$R$^8$, —SR$^{11}$, where R$^{11}$ is selected from the group consisting of H, alkyl of 1–4 carbons, aryl of 6–10 carbons and heteroaryl; alkyl, aryl, heteroaryl, —(CH$_2$)$_n$S, —(CH$_2$)$_n$OR$^9$, and —(CH$_2$)$_n$NR$^7$R$^8$;

b) reacting said indole with a 2-indanone defined by the general formula:

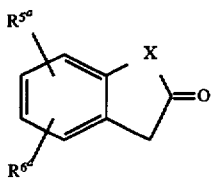

wherein:

R$^{5a}$ and R$^{6a}$ are each independently selected from the group consisting of H, F, Cl, Br, I, alkyl, aryl, heteroaryl, CN, NO$_2$, OR$^9$, —O(CH$_2$)$_n$NR$^7$R$^8$, CO$_2$R$^9$, SO$_2$R$^9$, SR$^{11}$, —(CH$_2$)$_n$S(O)$_y$R$^9$, wherein y is an integer selected from the group consisting of 1 and 2; —(CH$_2$)$_n$SR$^{11}$, NR$^7$R$^8$, and —(CH$_2$)$_n$NR$^7$R$^8$, and X is selected from the group consisting of an alkylene group of 1–3 carbons and —C(R$^{10}$)$_2$—;

under conditions capable of forming a 2-(2-cycloalkenyl) indolo tertiary alcohol defined by Formula V:

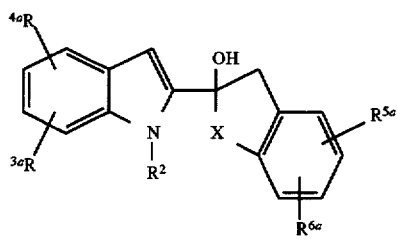

V c) eliminating the hydroxyl group of the alcohol of said Formula V to form a 2-(2-cycloalkenyl)indole defined by Formula VI:

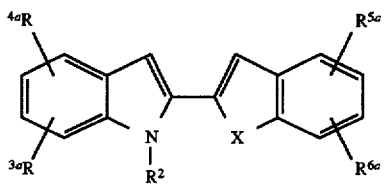

VI d) reacting said Formula VI with an imide defined by the general formula:

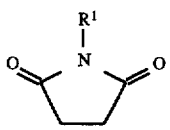

wherein:

R$^1$ is selected from the group consisting of H, alkyl of 1–4 carbons, aryl, arylalkyl, heteroaryl, and heteroarylalkyl; COR$^9$, where R$^9$ is selected from the group consisting of alkyl of 1–4 carbons, and aryl, —OR$^{10}$, where R$^{10}$ is selected from the group consisting of H and alkyl of 1–4 carbons; —CONH$_2$, —NR$^7$R$^8$, —(CH$_2$)$_n$NR$^7$R$^8$, wherein n is an integer of 1–4; and —O(CH$_2$)$_n$NR$^7$R$^8$; wherein either 1) R$^7$ and R$^8$ independently are selected from the group consisting of H and alkyl of 1–4 carbons; or 2) R$^7$ and R$^8$ are combined together to form a linking group of the general formula —(CH$_2$)$_2$—X$^1$—(CH$_2$)$_2$—, where X$^1$ is selected from the group consisting of O, S and CH$_2$;

under conditions which form a tetrahydropyrrolocarbazole defined by Formula VII:

and e) dehydrogenating the tetrahydrocarbazole ring of said Formula VII under conditions which form a fused pyrrolocarbazole defined by Formula VIII.

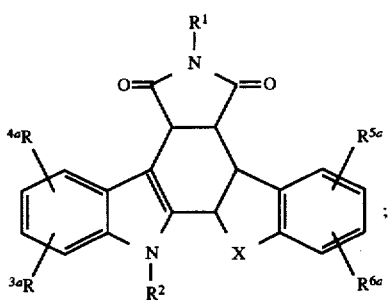

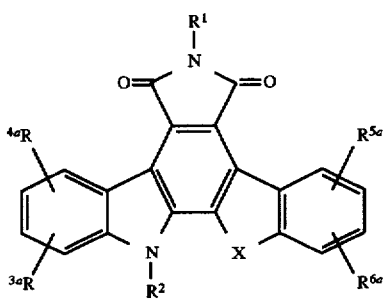

wherein:
R², R³ᵃ and R⁴ᵃ are as defined in (a) above; R⁵ᵃ, R⁶ᵃ and X are as defined in (b) above; and R¹ is defined as in (d) above.

32. A method for making regiospecific D-ring-fused pyrrolocarbazole lactam isomers, said method comprising the steps of:

a) obtaining a fused pyrrolocarbazole defined by Formula VIII:

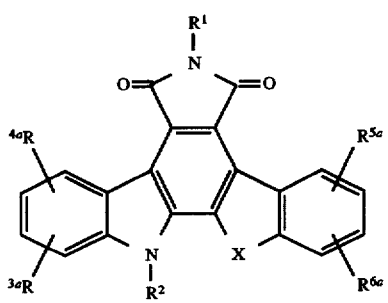

wherein:
R¹ is selected from the group consisting of H, alkyl of 1–4 carbons, aryl, arylalkyl, heteroaryl, and heteroarylalkyl; COR⁹, where R⁹ is selected from the group consisting of alkyl of 1–4 carbons, and aryl, —OR¹⁰, where R¹⁰ is selected from the group consisting of H and alkyl of 1–4 carbons; —CONH₂, —NR⁷R⁸, —(CH₂)ₙNR⁷R⁸, wherein n is an integer of 1–4; and —O(CH₂)ₙNR⁷R⁸; wherein either 1) R⁷ and R⁸ independently are selected from the group consisting of H and alkyl of 1–4 carbons; or 2) R⁷ and R⁸ are combined together to form a linking group of the general formula —(CH₂)₂—X¹—(CH₂)₂—, where X¹ is selected from the group consisting of O, S and CH₂;

R² is selected from the group consisting of H, SO₂R⁹, CO₂R⁹, and alkyl of 1–4 carbons;

R³ᵃ and R⁴ᵃ are each independently selected from the group consisting of H, F, Cl, Br, I, —OR⁹, —O(CH₂)ₙNR⁷R⁸, NR⁷R⁸, —SR¹¹, where R¹¹ is selected from the group consisting of H, alkyl of 1–4 carbons, aryl of 6–10 carbons and heteroaryl; alkyl, aryl, heteroaryl, —(CH₂)ₙSR¹¹, —(CH₂)ₙOR⁹, and —(CH₂)ₙNR⁷R⁸; R⁵ᵃ and R⁶ᵃ are each independently selected from the group consisting of H, F, Cl, Br, I, alkyl, aryl, heteroaryl, CN, NO₂, OR⁹, —O(CH₂)ₙNR⁷R⁸, CO₂R⁹, SO₂R⁹, SR¹¹, —(CH₂)ₙS(O)ᵧR⁹, wherein y is an integer selected from the group consisting of 1 and 2; —(CH₂)ₙSR¹¹, NR⁷R⁸, and —(CH₂)ₙNR⁷R⁸, and X is selected from the group consisting of an alkylene group of 1–3 carbons and —C(R¹⁰)₂—;

b) reducing the imide group of said fused pyrrolocarbazole under conditions which form fused pyrrolocarbazole lactam isomers defined by Formula IX and Formula X:

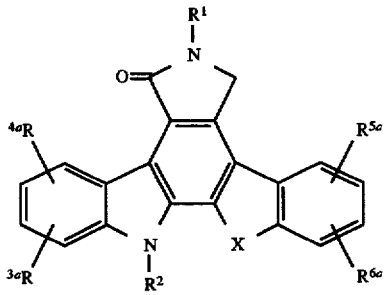

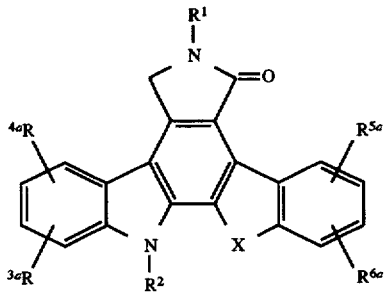

wherein:
R¹ is defined in (a) above; and
R², R³ᵃ, R⁴ᵃ R⁵ᵃ, R⁶ᵃ and X are as defined in (a)(2) above; and c) separating the isomer of Formula IX from the isomer of Formula X under conditions which produce substantially pure regiospecific D-ring-fused pyrrolocarbazole lactam isomers.

33. A method of making regiospecific D-ring fused pyrrolocarbazole lactam isomer, said method comprising the steps of:

a) obtaining a compound defined by Formula XI:

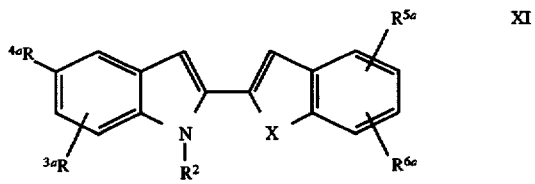

wherein:
R² is selected from the group consisting of H, SO₂R⁹, CO₂R⁹, and alkyl of 1–4 carbons;

$R^{3a}$ and $R^{4a}$ are each independently selected from the group consisting of H, F, Cl, Br, I, —OR$^9$, —O(CH$_2$)$_n$NR$^7$R$^8$, NR$^7$R$^8$, —SR$^{11}$, where R$^{11}$ is selected from the group consisting of H, alkyl of 1–4 carbons, aryl of 6–10 carbons and heteroaryl; alkyl, aryl, heteroaryl, —(CH$_2$)$_n$SR$^{11}$, —(CH$_2$)$_n$OR$^9$, and —(CH$_2$)$_n$NR$^7$R$^8$; R$^{5a}$ and R$^{6a}$ are each independently selected from the group consisting of H, F, Cl, Br, I, alkyl, aryl, heteroaryl, CN, NO$_2$, OR$^9$, —O(CH$_2$)$_n$NR$^7$R$^8$, CO$_2$R$^9$, SO$_2$R$^9$, SR$^{11}$, —(CH$_2$)$_n$S(O)$_y$R$^9$, wherein y is an integer selected from the group consisting of 1 and 2; —(CH$_2$)$_n$SR$^{11}$, NR$^7$R$^8$, and —(CH$_2$)$_n$NR$^7$R$^8$, and X is selected from the group consisting of S, O, CO, alkylene of 1–3 carbons, —C(R$^{10}$)$_2$—, —CH$_2$Z—, where Z is selected from the group consisting of C(R$^{11}$)(OR$^{11}$), O, S, C(=NOR$^{11}$), and NR$^{11}$; —ZCH$_2$—, and —CH$_2$ZCH$_2$—;

b) reacting said Formula XI with a lower alkyl β-cyanoacrylate under conditions which form regiospecific tetrahydrocarbazole cyano-ester isomers defined by Formula XII and Formula XV:

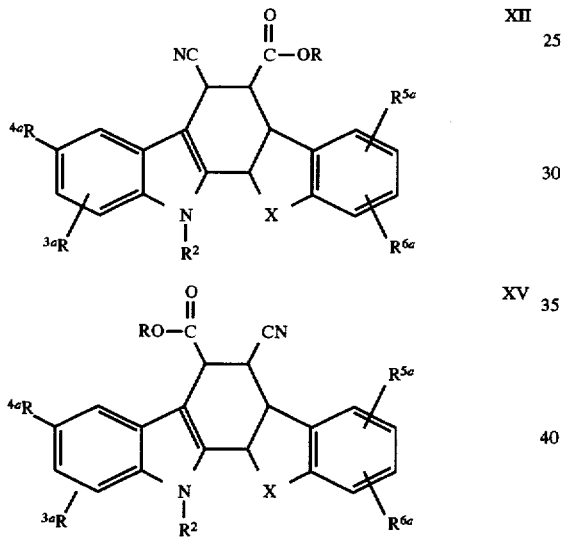

wherein R is a lower alkyl group;

c) separating the isomer of Formula XII from the isomer of Formula XV under conditions which produce substantially pure regiospecific tetrahydrocarbazole cyano-ester isomers;

d) (1) dehydrogenating the tetrahydrocarbazole ring of the isomer of Formula XII sufficient to form a carbazole cyano-ester defined by Formula XIII:

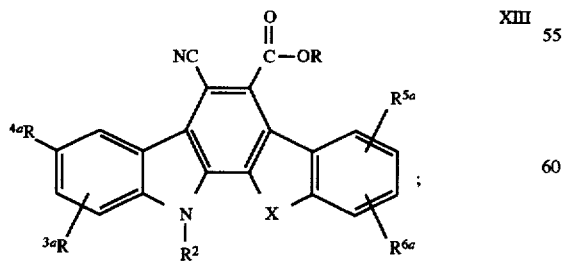

and (2) dehydrogenating the tetrahydrocarbazole ring of the isomer of Formula XV sufficient to form a carbazole cyano-ester defined by Formula XVI:

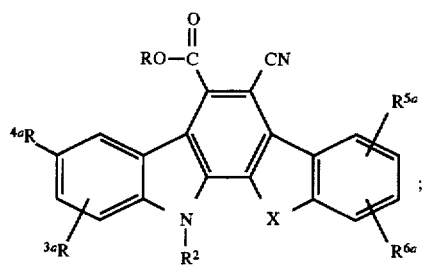

and e) (1) reacting the carbazole cyano-ester of Formula XIII under reductive conditions which produce regiospecific fused pyrrolocarbazoles defined by Formula XIV:

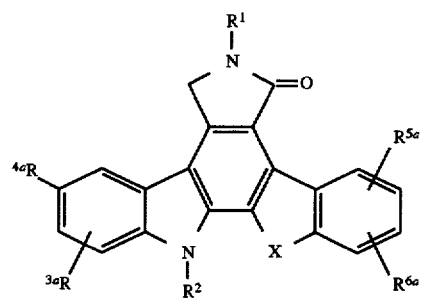

wherein:

R$^1$ is selected from the group consisting of H, alkyl of 1–4 carbons, aryl, arylalkyl, heteroaryl, and heteroarylalkyl; COR$^9$, where R$^9$ is selected from the group consisting of alkyl of 1–4 carbons, and aryl, —OR$^{10}$, where R$^{10}$ is selected from the group consisting of H and alkyl of 1–4 carbons; —CONH$_2$, —NR$^7$R$^8$, —(CH$_2$)$_n$NR$^7$R$^8$, wherein n is an integer of 1–4; and —O(CH$_2$)$_n$NR$^7$R$^8$; wherein either 1) R$^7$ and R$^8$ independently are selected from the group consisting of H and alkyl of 1–4 carbons; or 2) R$^7$ and R$^8$ are combined together to form a linking group of the general formula —(CH$_2$)$_2$—X$^1$—(CH$_2$)$_2$—, where X$^1$ is selected from the group consisting of O, S and CH$_2$;

R$^2$, R$^{3a}$, R$^{4a}$ R$^{5a}$, R$^{6a}$ and X are as defined in (a) above; and (2) reacting the carbazole cyano-ester of Formula XVI under reductive conditions which produce regiospecific fused pyrrolocarbazoles defined by Formula XVII:

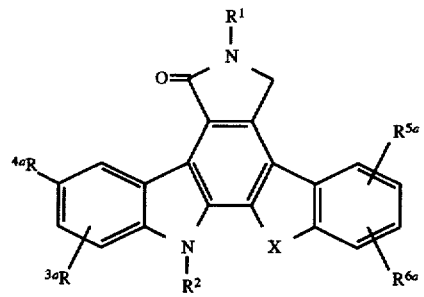

wherein:

R$^1$ is defined as in (e)(1) above; R$^2$, R$^{3a}$, R$^{4a}$ R$^{5a}$, R$^{6a}$ and X are as defined in (a) above.

34. A method of making a D-ring-fused pyrrolocarbazole, said method comprising the steps of:

a) obtaining an indole defined by Formula IV:

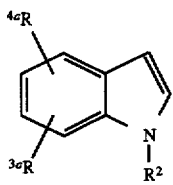
IV wherein:

$R^2$ is selected from the group consisting of H, $SO_2R^9$, $CO_2R^9$, and alkyl of 1–4 carbons;

$R^{3a}$ and $R^{4a}$ are each independently selected from the group consisting of H, F, Cl, Br, I, —$OR^9$, —$O(CH_2)_nNR^7R^8$, $NR^7R^8$, —$SR^{11}$, where $R^{11}$ is selected from the group consisting of H, alkyl of 1–4 carbons, aryl of 6–10 carbons and heteroaryl; alkyl, aryl, heteroaryl, —$(CH_2)_nSR^{11}$, —$(CH_2)_nOR^9$, and —$(CH_2)_nNR^7R^8$;

b) reacting said indole with a 2-benzocycloalkanone defined by the general formula:

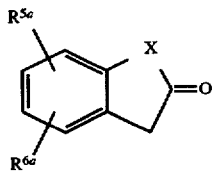

wherein:

$R^{5a}$ and $R^{6a}$ are each independently selected from the group consisting of H, F, Cl, Br, I, alkyl, aryl, heteroaryl, CN, $NO_2$, $OR^9$, —$O(CH_2)_nNR^7R^8$, $CO_2R^9$, $SO_2R^9$, $SR^{11}$, —$(CH_2)_nS(O)_yR^9$, where y is an integer selected from the group consisting of 1 and 2; —$(CH_2)_nSR^{11}$, $NR^7R^8$, and —$(CH_2)_nNR^7R^8$, and X is an alkylene 2–3 carbons;

under conditions which form Formula V:

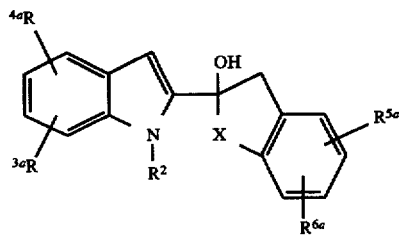
V c) eliminating the hydroxyl group to form the corresponding Formula VI;

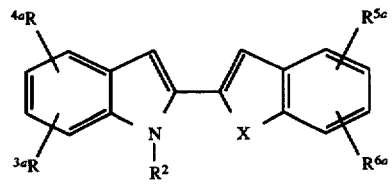
VI d) reacting said Formula VI with an imide defined by the general formula:

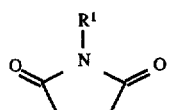

wherein:

$R^1$ is selected from the group consisting of H, alkyl of 1–4 carbons, aryl, arylalkyl, heteroaryl, and heteroarylalkyl; $COR^9$, where $R^9$ is selected from the group consisting of alkyl of 1–4 carbons, and aryl, —$OR^{10}$, where $R^{10}$ is selected from the group consisting of H and alkyl of 1–4 carbons; —$CONH_2$, —$NR^7R^8$, —$(CH_2)_nNR^7R^8$, wherein n is an integer of 1–4; and —$O(CH_2)_nNR^7R^8$; wherein either 1) $R^7$ and $R^8$ independently are selected from the group consisting of H and alkyl of 1–4 carbons; or 2) $R^7$ and $R^8$ are combined together to form a linking group of the general formula —$(CH_2)_2$—$X^1$—$(CH_2)_2$—, where $X^1$ is selected from the group consisting of O, S and $CH_2$;

under conditions which form a tetrahydroarylalkylpyrrolocarbazole defined by Formula XVIII:

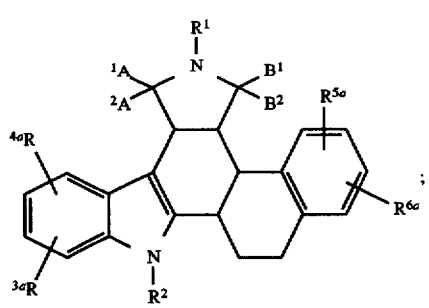
XVIII and e) (1) dehydrogenating the D-ring of said pyrrolocarbazole under conditions which produce a fused pyrrolocarbazole defined by Formula XIX:

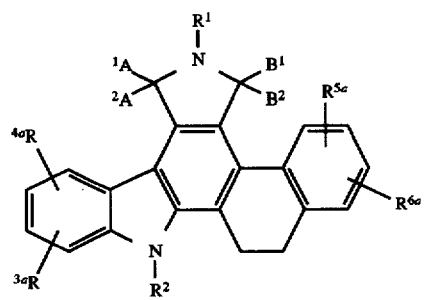
XIX i) wherein $A^1$ and $A^2$ are selected from the group consisting of H, H; H, —$OR^{11}$; H, —$SR^{11}$; H, —$N(R^{11})_2$; and a group wherein $A^1$ and $A^2$ together form a moiety selected from the group consisting of =O; =S; and =$NR^{11}$; and ii) $B^1$ and $B^2$ are selected from the group consisting of: H, H; H, —$OR^{11}$; H, —$SR^{11}$; H, —$N(R^{11})_2$; and a group wherein $B^1$ and $B^2$ are selected from the group consisting of =O, =S; and =$NR^{11}$ with the proviso that at least one of the pairs $A^1$, $A^2$ or $B^1$, $B^2$ is =O; and iii) $R^1$ is defined in (d) above; $R^2$, $R^{3a}$, $R^{4a}$ are as defined in (a) above; $R^{5a}$, $R^{6a}$ and X are as defined in (b) above; and e) (2) dehydrogenating the E-ring of said pyrrolocarbazote under conditions which produce a fused pyrrolocarbazole defined by Formula XX:

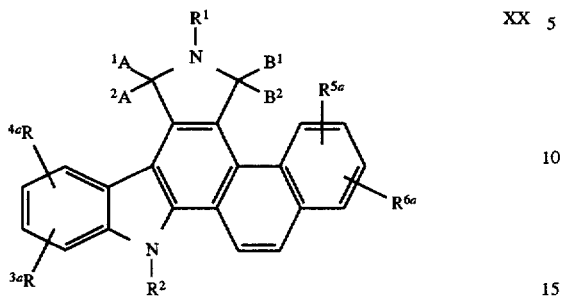

i) wherein $A^1$ and $A^2$ are selected from the group consisting of H, H; H, —$OR^{11}$; H, —$SR^{11}$; H, —$N(R^{11})_2$; and a group wherein $A^1$ and $A^2$ together form a moiety selected from the group consisting of =O; =S; and =$NR^{11}$; and ii) $B^1$ and $B^2$ are selected from the group consisting of: H, H; H, —$OR^{11}$; H, —$SR^1$; H, —$N(R^{11})_2$; and a group wherein $B^1$ and $B^2$ are selected from the group consisting of =O, =S; and =$NR^{11}$ with the proviso that at least one of the pairs $A^1$, $A^2$ or $B^1$, $B^2$ is =O; and iii) $R^1$ is defined in (d) above; $R^2$, $R^{3a}$, $R^{4a}$ are as defined in (a) above; and $R^{5a}$, $R^{6a}$ and X are as defined in (b) above.

35. A method of making a D-ring-fused pyrrolocarbazole, said method comprising the steps of:

a) obtaining a lower alkyl stannylindole defined by Formula XXI:

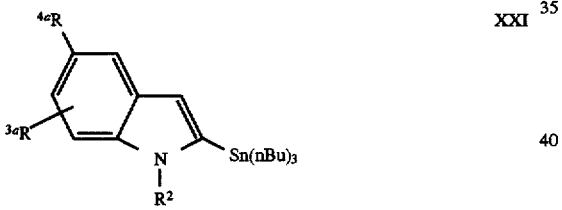

wherein:
$R^2$ is selected from the group consisting of —$CO_2H$, —$SO_2R^9$, —$CO_2R^9$ and alkyl;
$R^{3a}$ and $R^{4a}$ are each independently selected from the group consisting of H, F, Cl, Br, I, —$OR^9$, —$O(CH_2)_nNR^7R^8$, $NR^7R^8$, —$SR^{11}$, where $R^{11}$ is selected from the group consisting of H, alkyl of 1–4 carbons, aryl of 6–10 carbons and heteroaryl; alkyl, aryl, heteroaryl, —$(CH_2)_nSR^{11}$, —$(CH_2)_nOR^9$, and —$(CH_2)_nNR^7R^8$;

b) coupling said Formula XXI with a compound defined by the general formula:

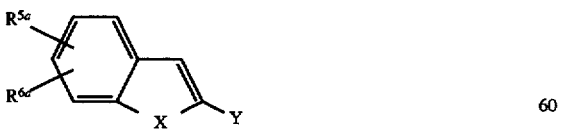

wherein:
$R^{5a}$ and $R^{6a}$ are each independently selected from the group consisting of H, F, Cl, Br, I, alkyl, aryl, heteroaryl, CN, $NO_2$, $OR^9$, —$O(CH_2)_nNR^7R^8$, $CO_2R^9$, $SO_2R^9$, $SR^{11}$, —$(CH_2)_nS(O)_yR^9$, where y is an integer selected from the group consisting of 1 and 2; —$(CH_2)_nSR^{11}$, $NR^7R^8$, and —$(CH_2)_nNR^7R^8$; X is selected from the group consisting of S, O, CO, alkylene of 1–3 carbons, —$C(R^{10})_2$—, —$CH_2Z$—, where Z is selected from the group consisting of $C(R^{11})(OR^{11})$, O, S, $C(=NOR^{11})$, and $NR^{11}$; —$ZCH_2$, and $CH_2ZCH_2$—; and Y is Br, I, or —$OSO_2CF_3$;

under conditions which form an indole defined by Formula XXII:

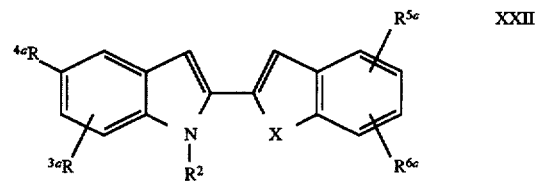

c) separately reacting said Formula XXII with either:
i) an imide defined by the general formula:

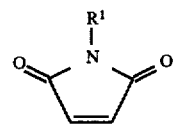

or
ii) a lower alkyl β-cyanoacrylate;
each independently under conditions which form an indoloimide defined by Formula XXIII:

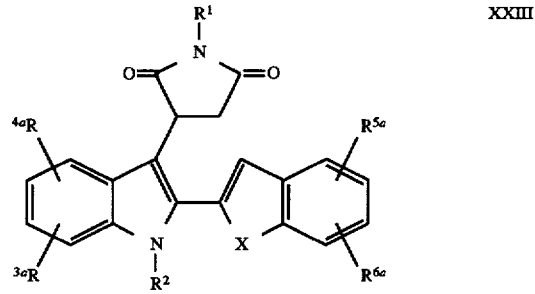

and
d) cyclizing said Formula XXIII under conditions which form a fused pyrrolocarbazole defined by Formula XXIV:

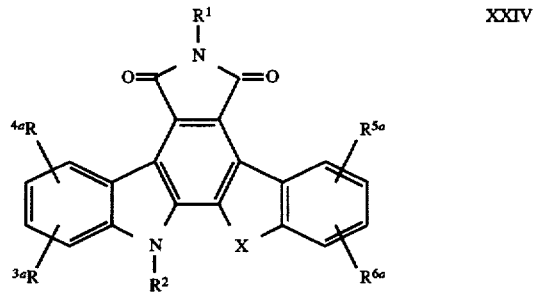

wherein:
$R^1$ is selected from the group consisting of H, alkyl of 1–4 carbons, aryl, arylalkyl, heteroaryl, and heteroarylalkyl; $COR^9$, where $R^9$ is selected from the group consisting of alkyl of 1–4 carbons, and aryl, —$OR^{10}$, where $R^{10}$ is selected from the group consisting of H and alkyl of 1–4 carbons; —CONH$_2$, —NR$^7$R$^8$, —(CH$_2$)$_n$NR$^7$R$^8$, wherein n is an integer selected from the group consisting of 1–4; and —O(CH$_2$)$_n$NR$^7$R$^8$; wherein either 1) R$^7$ and R$^8$ independently are selected from the group consisting of H and alkyl of 1–4 carbons; or
2) R$^7$ and R$^8$ are combined together to form a linking group of the general formula —(CH$_2$)$_2$—X$^1$—(CH$_2$)$_2$—, where X$^1$ is selected from the group consisting of O, S and CH$_2$;

R$^2$, R$^{3a}$, R$^{4a}$ are as defined in (a) above; and R$^{5a}$, R$^{6a}$ and X are as defined in (b) above.

36. The process of claim 31 wherein R$^9$ is selected from the group consisting of phenyl and naphthyl.

37. The process of claim 31 wherein R$^{11}$ is selected from the group consisting of phenyl and naphthyl.

38. The process of claim 32 wherein R$^9$ is selected from the group consisting of phenyl and naphthyl.

39. The process of claim 32 wherein R$^{11}$ is selected from the group consisting of phenyl and naphthyl.

40. The process of claim 33 wherein R$^9$ is selected from the group consisting of phenyl and naphthyl.

41. The process of claim 33 wherein R$^{11}$ is selected from the group consisting of phenyl and naphthyl.

42. The process of claim 33 wherein the lower alkyl β-cyanoacrylate is ethyl-β-cyanoacrylate.

43. The process of claim 34 wherein R$^9$ is selected from the group consisting of phenyl and naphthyl.

44. The process of claim 34 wherein R$^{11}$ is selected from the group consisting of phenyl and naphthyl.

45. The process of claim 35 wherein R$^9$ is selected from the group consisting of phenyl and naphthyl.

46. The process of claim 35 wherein R$^{11}$ is selected from the group consisting of phenyl and naphthyl.

47. A method for effecting the function and/or survival of a trophic factor responsive cell comprising the step of contacting said cell with at least one fused pyrrolocarbazole of claim 1.

48. A method for effecting the function and/or survival of a trophic factor responsive cell comprising the step of contacting said cell with at least one fused pyrrolocarbazole of claim 2.

49. A method for effecting the function and/or survival of a trophic factor responsive cell comprising the step of contacting said cell with at least one fused pyrrolocarbazole of claim 3.

50. A method for effecting the function and/or survival of a trophic factor responsive cell comprising the step of contacting said cell with at least one fused pyrrolocarbazole of claim 4.

51. The method of claim 47 wherein said effecting is in the form of enhancement.

52. The method of claim 47 wherein said effecting is in the form of inhibition.

53. The method of claim 47 wherein said trophic factor responsive cell is a neuron.

54. The method of claim 53 wherein said neuron is selected from the group comprising cholinergic neurons and sensory neurons.

55. A method for inhibiting the kinase activity of a protein kinase, said method comprising contacting said protein kinase with at least one fused pyrrolocarbazole of claim 1.

56. A method for inhibiting the kinase activity of a protein kinase, said method comprising contacting said protein kinase with at least one fused pyrrolocarbazole of claim 2.

57. A method for inhibiting the kinase activity of a protein kinase, said method comprising contacting said protein kinase with at least one fused pyrrolocarbazole of claim 3.

58. A method for inhibiting the kinase activity of a protein kinase, said method comprising contacting said protein kinase with at least one fused pyrrolocarbazole of claim 4.

59. The method of claim 55 wherein said protein kinase is selected from the group consisting of protein kinase C and trk tyrosine kinase.

60. A method for inhibiting the induction by interferon-γ of indoleamine 2,3-dioxygenase comprising the step of contacting cells which transcribe interferon-γ specific genes with at least one fused pyrrolocarbazole of claim 1.

61. A method for inhibiting the induction by interferon-γ of indoleamine 2,3-dioxygenase comprising the step of contacting cells which transcribe interferon-γ specific genes with at least one fused pyrrolocarbazole of claim 2.

62. A method for inhibiting the induction by interferon-γ of indoleamine 2,3-dioxygenase comprising the step of contacting cells which transcribe interferon-γ specific genes with at least one fused pyrrolocarbazole of claim 3.

63. A method for inhibiting the induction by interferon-γ of indoleamine 2,3-dioxygenase comprising the step of contacting cells which transcribe interferon-γ specific genes with at least one fused pyrrolocarbazole of claim 4.

64. A method for enhancing the survival of a cell at risk of dying comprising the step of contacting said cell with at least one fused pyrrolocarbazole of claim 1.

65. A method for enhancing the survival of a cell at risk of dying comprising the step of contacting said cell with at least one fused pyrrolocarbazole of claim 2.

66. A method for enhancing the survival of a cell at risk of dying comprising the step of contacting said cell with at least one fused pyrrolocarbazole of claim 3.

67. A method for enhancing the survival of a cell at risk of dying comprising the step of contacting said cell with at least one fused pyrrolocarbazole of claim 4.

68. The method of claim 64 wherein said cell is at risk of dying due to a process selected from the group consisting of aging, trauma, and disease.

69. The method of claim 68 wherein said cell is a neuron.

* * * * *